US011906512B2

(12) United States Patent
Guirguis

(10) Patent No.: US 11,906,512 B2
(45) Date of Patent: Feb. 20, 2024

(54) INTEGRATED DEVICE FOR ANALYTE TESTING, CONFIRMATION, AND DONOR IDENTITY VERIFICATION

(71) Applicant: Zeus Diagnostics, LLC, Wilmington, DE (US)

(72) Inventor: Raouf A. Guirguis, Fond Du Lac, WI (US)

(73) Assignee: ZEUS DIAGNOSTICS, LLC, Wilmington, DE (US)

( * ) Notice: Subject to any disclaimer, the term of this patent is extended or adjusted under 35 U.S.C. 154(b) by 1298 days.

(21) Appl. No.: 16/024,033

(22) Filed: Jun. 29, 2018

(65) Prior Publication Data

US 2019/0049442 A1 Feb. 14, 2019

Related U.S. Application Data

(63) Continuation-in-part of application No. 15/418,044, filed on Jan. 27, 2017, now abandoned, which is a
(Continued)

(51) Int. Cl.
*G01N 33/558* (2006.01)
*G01N 33/543* (2006.01)
(Continued)

(52) U.S. Cl.
CPC ....... *G01N 33/54388* (2021.08); *A61B 5/157* (2013.01); *A61B 5/150022* (2013.01);
(Continued)

(58) Field of Classification Search
CPC ................. G01N 33/558; G01N 33/94; G01N 33/54387; G01N 33/54388;
(Continued)

(56) References Cited

U.S. PATENT DOCUMENTS 3,784,358 A 1/1974 Drake, Jr.
4,375,815 A 3/1983 Burns
(Continued)

FOREIGN PATENT DOCUMENTS

EP 0200381 B1 11/1986
EP 0203238 A1 12/1986
(Continued)

OTHER PUBLICATIONS

Amazon.com, "self triggered lancets", accessed Mar. 6, 2023, 6 pages, https://www.amazon.com/s?k=self+triggered+lancets&i=industrial&crid=2WR0II69AP7VW&sprefix=self+triggered+lancets%2Cindustrial%2C54&ref=nb_sb_noss.
(Continued)

*Primary Examiner* — Christopher L Chin
(74) *Attorney, Agent, or Firm* — CANTOR COLBURN LLP

(57) ABSTRACT

An apparatus for testing a fluid sample including a sample receiving member having an opening for receiving a fluid sample, wherein the sample receiving member comprises a sample collection chamber; a fluid collector to collect the fluid sample and transfer the fluid sample into the sample receiving member, the fluid collector comprising a lancet and an absorbent material to absorb the fluid sample; and a test cartridge member in fluid communication with the sample collection chamber.

17 Claims, 37 Drawing Sheets

Related U.S. Application Data continuation-in-part of application No. 14/595,206, filed on Jan. 12, 2015, now abandoned, which is a continuation of application No. 12/975,471, filed on Dec. 22, 2010, now Pat. No. 8,940,527, which is a continuation of application No. 12/029,418, filed on Feb. 11, 2008, now Pat. No. 7,879,623, which is a continuation-in-part of application No. 11/394,189, filed on Mar. 31, 2006, now Pat. No. 7,741,103.

(51) Int. Cl.
| | | |
|---|---|---|
| *A61B 5/157* | (2006.01) | |
| *A61B 10/00* | (2006.01) | |
| *G01N 33/94* | (2006.01) | |
| *A61B 5/15* | (2006.01) | |
| *G06V 40/13* | (2022.01) | |
| *A61B 90/90* | (2016.01) | |
| *A61B 90/98* | (2016.01) | |

(52) U.S. Cl.
CPC .. *A61B 5/150305* (2013.01); *A61B 5/150343* (2013.01); *A61B 10/007* (2013.01); *A61B 10/0038* (2013.01); *A61B 10/0051* (2013.01); *G01N 33/94* (2013.01); *G06V 40/1306* (2022.01); *A61B 90/90* (2016.02); *A61B 90/98* (2016.02); *A61B 2010/0006* (2013.01); *A61B 2010/0009* (2013.01); *Y10S 435/81* (2013.01); *Y10S 435/97* (2013.01); *Y10S 435/973* (2013.01); *Y10S 436/81* (2013.01)

(58) Field of Classification Search
CPC .... G01N 2035/00108; A61B 5/150022; A61B 5/150305; A61B 5/150343; A61B 5/157; A61B 10/0038; A61B 10/0051; A61B 10/007; A61B 90/90; A61B 90/98; A61B 2010/0006; A61B 2010/0009; A61B 5/1411; A61B 5/150053; A61B 5/150167; A61B 5/150412; A61B 5/151; A61B 5/15186; A61B 5/15192; G06V 40/13; G06V 40/1306; Y10S 435/81; Y10S 435/97; Y10S 435/973; Y10S 436/81; B01L 2300/0825; B01L 2300/0672
USPC ....... 422/400, 401, 410, 419, 420, 421, 425, 422/426, 430, 554; 435/287.7, 287.9, 435/288.5, 970, 805, 810; 436/169, 170, 436/514, 518, 530, 810; 606/181, 182
See application file for complete search history.

(56) References Cited

U.S. PATENT DOCUMENTS

| | | | |
|---|---|---|---|
| 4,632,901 A | 12/1986 | Valkirs et al. | |
| 4,637,403 A * | 1/1987 | Garcia | A61B 5/15117 600/583 |
| 4,717,656 A | 1/1988 | Swanljung | |
| 4,774,192 A | 9/1988 | Terminiello et al. | |
| 4,775,636 A | 10/1988 | Moeremans et al. | |
| 4,810,630 A | 3/1989 | Craig et al. | |
| 4,817,632 A | 4/1989 | Schramm | |
| 4,826,759 A | 5/1989 | Guire et al. | |
| 4,853,335 A | 8/1989 | Olsen et al. | |
| 4,883,764 A | 11/1989 | Kloepfer | |
| 4,943,522 A | 7/1990 | Eisinger et al. | |
| 4,959,324 A | 9/1990 | Ramel et al. | |
| 4,963,325 A | 10/1990 | Lennon et al. | |
| 5,006,464 A | 4/1991 | Chu et al. | |
| 5,028,535 A | 7/1991 | Buechler et al. | |
| 5,071,746 A | 12/1991 | Wilk et al. | |
| 5,079,029 A | 1/1992 | Saunders | |
| 5,079,172 A | 1/1992 | Hari et al. | |
| 5,104,619 A | 4/1992 | De Castro et al. | |
| 5,221,627 A | 6/1993 | Grigg et al. | |
| 5,244,815 A | 9/1993 | Guirgulis | |
| 5,260,031 A | 11/1993 | Seymour | |
| 5,268,148 A | 12/1993 | Seymour | |
| 5,270,167 A | 12/1993 | Francoeur | |
| 5,283,038 A | 2/1994 | Seymour | |
| 5,308,580 A | 5/1994 | Clark | |
| 5,342,645 A | 8/1994 | Eisele et al. | |
| 5,376,337 A | 12/1994 | Seymour | |
| 5,378,492 A | 1/1995 | Mashiko | |
| 5,380,492 A | 1/1995 | Seymour | |
| 5,393,496 A | 2/1995 | Seymour | |
| 5,415,994 A | 5/1995 | Imrich et al. | |
| 5,416,000 A | 5/1995 | Allen et al. | |
| 5,441,698 A | 8/1995 | Norell | |
| 5,468,648 A | 11/1995 | Chandler | |
| 5,494,646 A | 2/1996 | Seymour | |
| 5,629,164 A | 5/1997 | Rivers | |
| 5,869,345 A | 2/1999 | Chandler | |
| 5,876,926 A | 3/1999 | Beecham | |
| 5,935,864 A | 8/1999 | Schramm et al. | |
| 5,951,492 A * | 9/1999 | Douglas | A61B 5/150343 600/583 |
| 6,009,484 A * | 12/1999 | Miller | G06F 9/4881 710/39 |
| 6,352,514 B1 * | 3/2002 | Douglas | A61B 5/150068 600/583 |
| 6,352,863 B1 | 3/2002 | Guirguis | |
| 6,365,417 B1 | 4/2002 | Fleming et al. | |
| 6,766,817 B2 | 7/2004 | Da Silva | |
| 7,060,505 B2 | 6/2006 | Guirguis | |
| 7,090,803 B1 | 8/2006 | Gould et al. | |
| 7,695,442 B2 * | 4/2010 | Wong | A61B 5/150213 600/583 |
| 7,741,103 B2 | 6/2010 | Guirguis | |
| 7,879,623 B2 | 2/2011 | Guirguis | |
| 7,927,562 B2 | 4/2011 | Wan et al. | |
| 8,328,737 B2 * | 12/2012 | Wong | A61B 5/150412 600/583 |
| 8,747,335 B2 * | 6/2014 | Wong | A61B 5/150412 600/583 |
| 8,852,124 B2 * | 10/2014 | Roe | A61B 5/150503 600/584 |
| 8,940,527 B2 | 1/2015 | Guirguis | |
| 9,198,641 B2 | 12/2015 | Slowey et al. | |
| 2002/0002344 A1 * | 1/2002 | Douglas | A61B 5/1519 600/583 |
| 2002/0160538 A1 | 10/2002 | Guirguis | |
| 2004/0029261 A1 | 2/2004 | Oldfield | |
| 2004/0138688 A1 * | 7/2004 | Giraud | A61B 5/14546 606/181 |
| 2004/0235192 A1 | 11/2004 | Guirguis | |
| 2006/0000894 A1 | 1/2006 | Bonalle | |
| 2007/0179436 A1 | 8/2007 | Braig et al. | |
| 2007/0239069 A1 | 10/2007 | Guirguis | |
| 2008/0194041 A1 | 8/2008 | Guirguis | |
| 2009/0215159 A1 | 8/2009 | Kirby | |
| 2019/0320960 A1 * | 10/2019 | Olson | A61B 5/150419 |

FOREIGN PATENT DOCUMENTS

| | | |
|---|---|---|
| EP | 0440350 A2 | 8/1991 |
| WO | 9216842 A1 | 10/1992 |
| WO | 9306486 | 4/1993 |

OTHER PUBLICATIONS

Chin, Non-Final Office Action in U.S. Appl. No. 11/394,189, dated Jan. 2008.
Cone et al. Stability of Cocaine In Saliva Clinical Chemistry vol. 34(7) p. 1508 (1988).
Craig Medical Distribution, Inc., http://www.craigmedical.com/products.htm, printed Feb. 17, 2017.
International Search Report for application No. PCT/US07/07956, dated Apr. 9, 2008.

(56) References Cited

OTHER PUBLICATIONS

International Search Report for application No. PCT/US09/00829, dated Apr. 2, 2009.
Raouf Guirgius, "Blood Fingerprick device with built in Screening Test Strips and Confirmation Vial.", accessed Mar. 7, 2023, https://www.youtube.com/watch?v=ZpJ_NCgkj3E.
Schramm et al. An Ultrafiltrate of Saliva Collected In Situ As A Biological Sample For Diagnostic Evaluation Clinical Chemistry vol. 37(1) pp. 114-115 (1991).
Wolff et al. Methadone In Saliva Clinical Chemistry vol. 37(7) pp. 1297-1298 (1991).

* cited by examiner

Front View

Top View

Back View

Front View

Front View

Back View

Back View

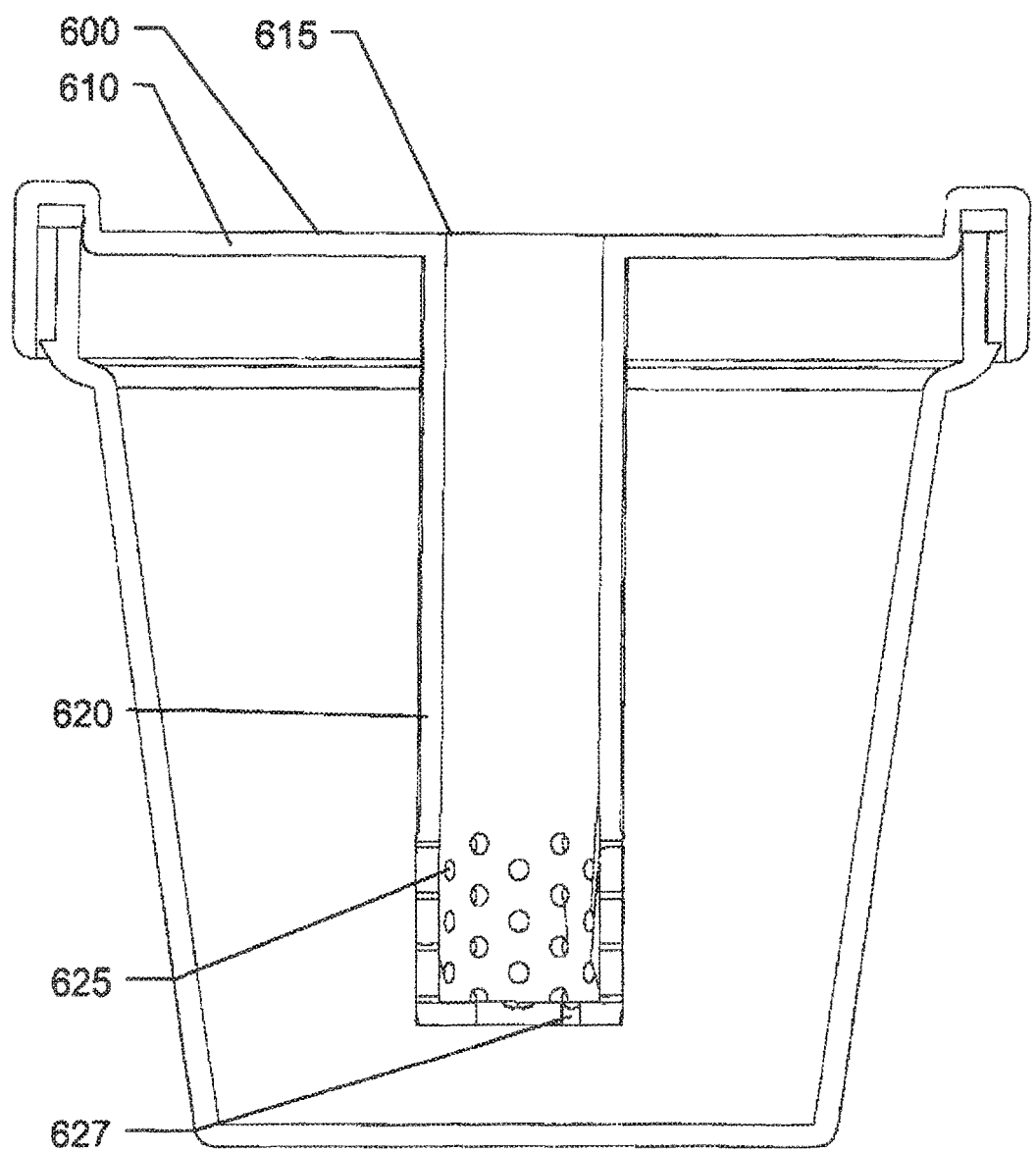

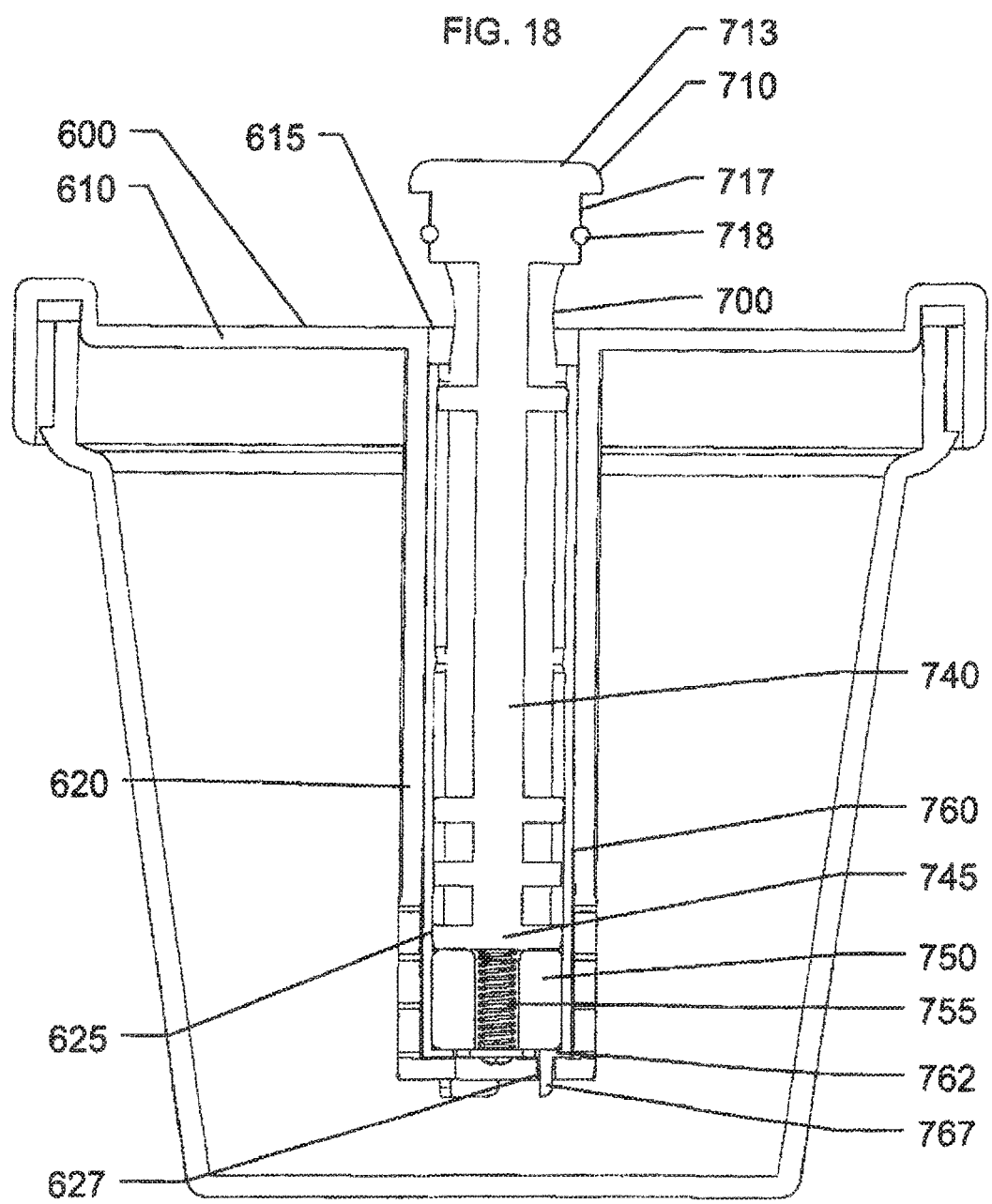

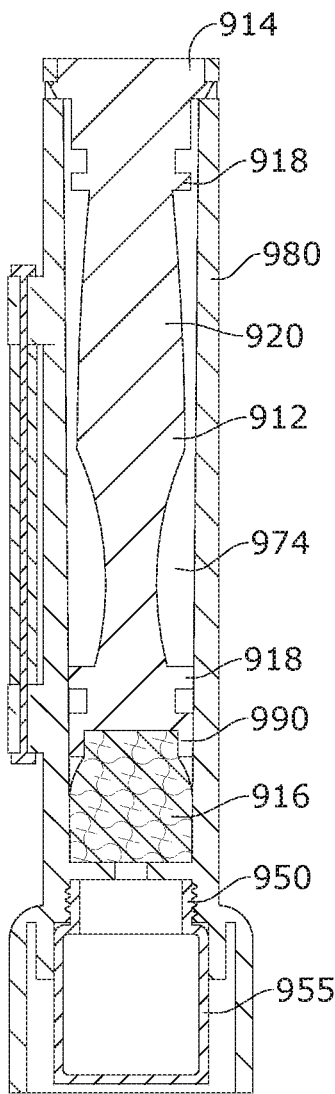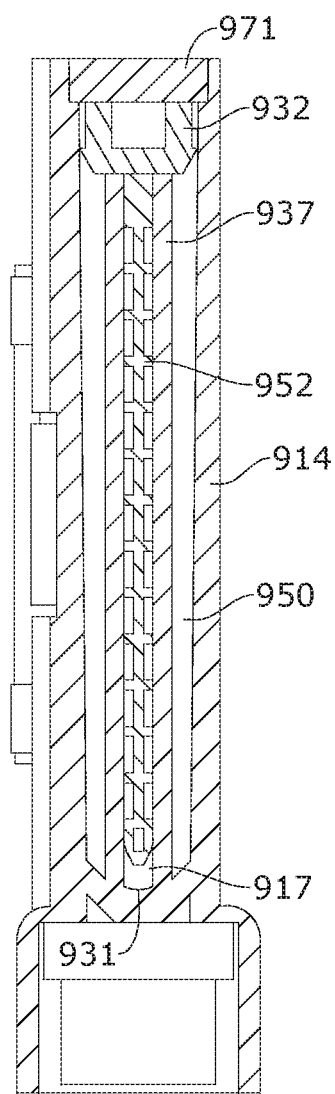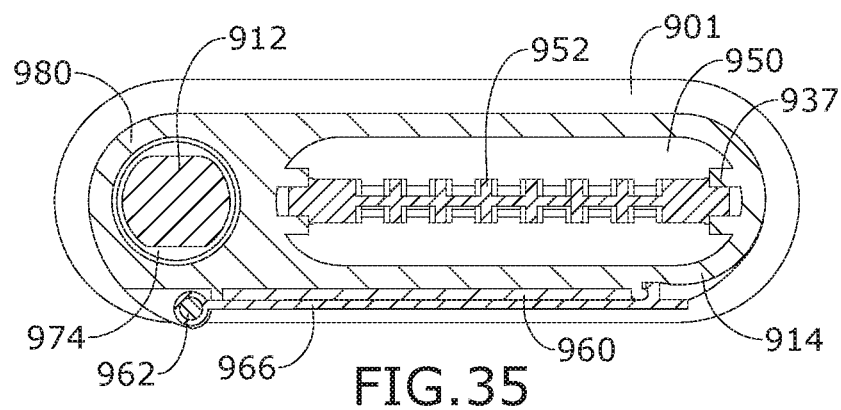

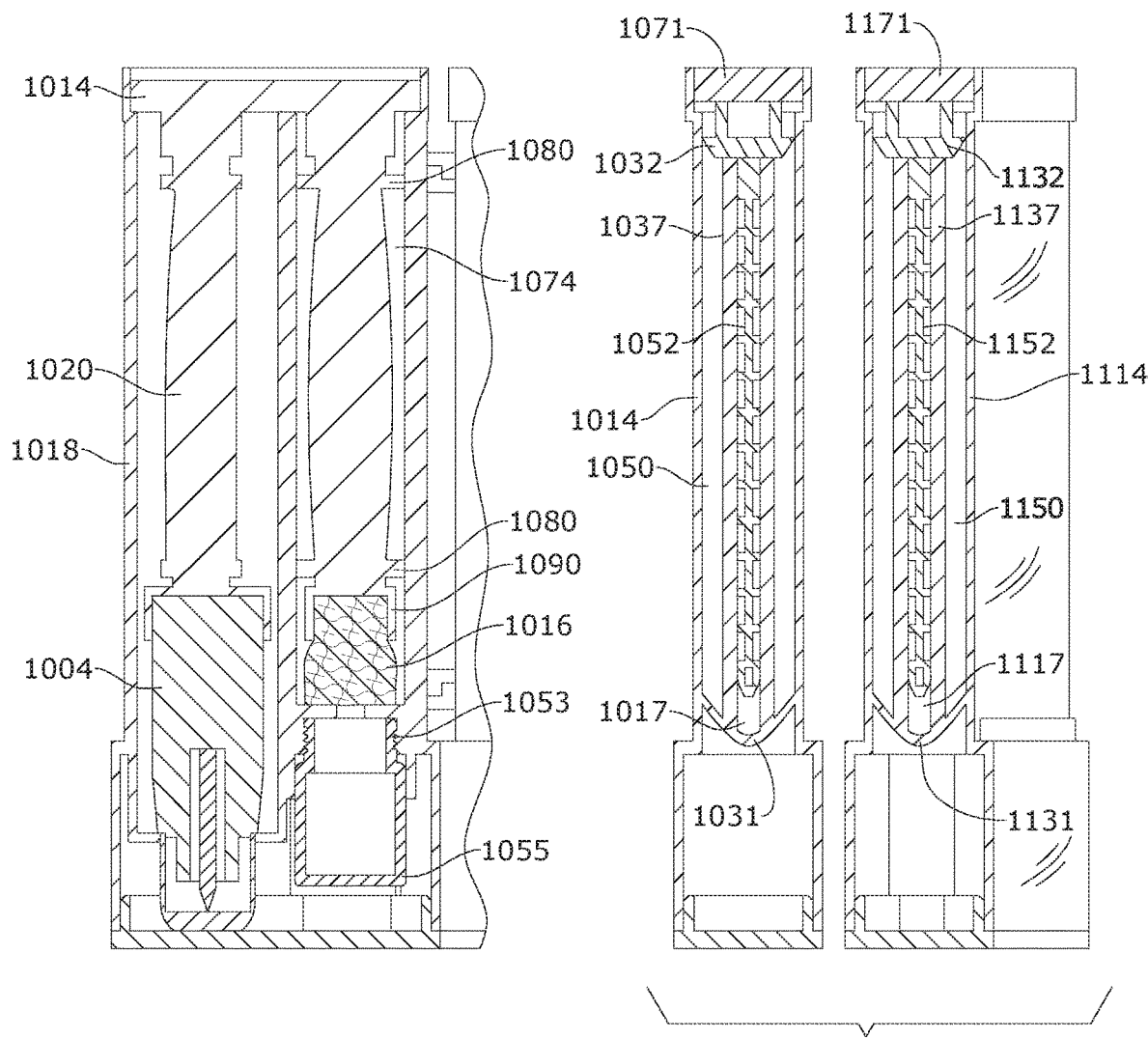

INTEGRATED DEVICE FOR ANALYTE TESTING, CONFIRMATION, AND DONOR IDENTITY VERIFICATION

CROSS-REFERENCE TO RELATED APPLICATIONS

This application is a Continuation-in-Part of U.S. application Ser. No. 15/418,044, filed Jan. 27, 2017, which is a Continuation-in-Part of U.S. application Ser. No. 14/595,206, filed Jan. 12, 2015, which is a continuation of U.S. patent application Ser. No. 12/975,471, filed Dec. 22, 2010, now granted as U.S. Pat. No. 8,940,527 on Jan. 27, 2015, which is a continuation of U.S. patent application Ser. No. 12/029,418, filed Feb. 11, 2008, now granted as U.S. Pat. No. 7,879,623 on Feb. 1, 2011, which is a Continuation-in-Part of U.S. patent application Ser. No. 11/394,189, filed Mar. 31, 2006, now granted as U.S. Pat. No. 7,741,103 on Jun. 22, 2010, all of which are hereby incorporated by reference, in their entireties, herein.

BACKGROUND OF THE INVENTION

1. Field of the Invention

The present invention relates to substance collection and testing. More particularly, the present invention relates to a device that tests a fluid sample for the presence or absence of at least one analyte, secures a separate fluid sample for later confirmation, and provides positive identification of an individual associated with the sample. In another aspect, the present invention relates to a device for collecting a fluid sample.

2. Background

Drug and other analyte testing has become ubiquitous in modern society. In homes, doctors' offices, law enforcement vehicles and offices, athletic facilities, and the workplace, effective, inexpensive and reliable testing devices have been sought. There is also a growing need for devices to test bodily fluids for substances that may assist in the diagnosis or management of diseases and other medical conditions.

The marketplace responded and is now replete with many devices directed to the testing of blood, urine or saliva. However, these devices may require a series of tests involving the shifting of the fluid sample being tested to different containers and/or the removal of the fluid sample to distant locations. These devices may also require the test administrator to handle the test subject's bodily fluids, incurring a danger of disease exposure.

Once an initial test result has been obtained, further testing of the fluid sample to confirm or refine the initial test result is often required. For a membrane test strip device, the fluid sample may not even be retained once the initial result is obtained, necessitating retention of a split sample. The need to retain a split sample incurs the risk that a sample could be lost, mislabeled, or contaminated.

Oftentimes, the chain of custody associated with a test sample imbues the results with doubt, as the fluid sample may become contaminated, misplaced or a different fluid sample may be substituted entirety. In many instances, identification of the test subject associated with the fluid sample is critically dispositive.

There is also a growing need for devices directed to testing for contaminants that may be found in food or water, such as pollutants, allergens, and harmful microbes. In some instances, it may be desirable to retain a fluid sample for confirmation testing or further analysis, retain a split fluid sample of the original sample for confirmation testing, or further analysis or to provide positive identification of the test administrator.

The Department of Transportation's (DOT) rule, 49 C.F.R. Part 40, describes required procedures for conducting workplace drug and alcohol testing for the Federally regulated transportation industry. Within this rule, definitions for split sample and split sample collection are provided. Split specimen is defined as, in drug testing, a part of the urine specimen that is sent to a first laboratory and retained unopened, and which is transported to a second laboratory in the event that the employee requests that it be tested following a verified positive test of the primary specimen or a verified adulterated or substituted test result. Split specimen collection is defined as a collection in which the urine collected is divided into two separate specimen bottles, the primary specimen (Bottle A) and the split specimen (Bottle B).

Thus, a need exists in the industry to combine the simplicity of current membrane test strip technology with the ability to positively identify the test subject and/or the test administrator, as well as the capability to secure a split portion of the fluid sample with a single device for later confirmation, within a single device.

BRIEF SUMMARY OF THE INVENTION

According to an embodiment, the invention provides an apparatus for testing a fluid sample including: a sample receiving member having an opening for receiving a fluid sample, wherein the sample receiving member comprises a sample collection chamber; a fluid collector to collect the fluid sample and transfer the fluid sample into the sample receiving member, the fluid collector comprising a lancet and an absorbent material to absorb the fluid sample; and a test cartridge member in fluid communication with the sample collection chamber.

According to another embodiment, the invention provides an apparatus for testing a fluid sample including: a sample receiving member having an opening for receiving a fluid sample, wherein the sample receiving member comprises a sample collection chamber; a fluid collector to collect the fluid sample and transfer the fluid sample into the sample receiving member, the fluid collector comprising a lancet and an absorbent material to absorb the fluid sample; a sample retention member, in fluid communication with the sample collection chamber, to retain a portion of the fluid sample; and at least one test strip, in fluid communication with the sample collection chamber, to indicate the presence or absence of at least one analyte in the fluid sample.

BRIEF DESCRIPTION OF THE DRAWINGS

The above and other advantages of this invention will become more apparent by the following description of invention and the accompanying drawings.

FIG. 17 depicts a cross-sectional front view of a urine cup in accordance with an embodiment of the present invention.

FIG. 18 depicts a cross-sectional front view of a urine cup with a fluid collector inserted therein in accordance with an embodiment of the present invention.

FIG. 33 depicts a cross-sectional view of the device taken along line 33-33 of FIG. 32.

FIG. 34 depicts a cross-sectional view of the device taken along line 34-34 of FIG. 32.

FIG. 35 depicts a cross-sectional view of a fluid collection and analyte testing device in accordance with an embodiment of the present invention.

FIG. 42 depicts a cross-sectional view of the device taken along line 42-42 of FIG. 41.

FIG. 43 depicts a cross-sectional view of the device taken along line 43-43 of FIG. 39.

DETAILED DESCRIPTION OF THE INVENTION

Analyte Screening

Figure 1:
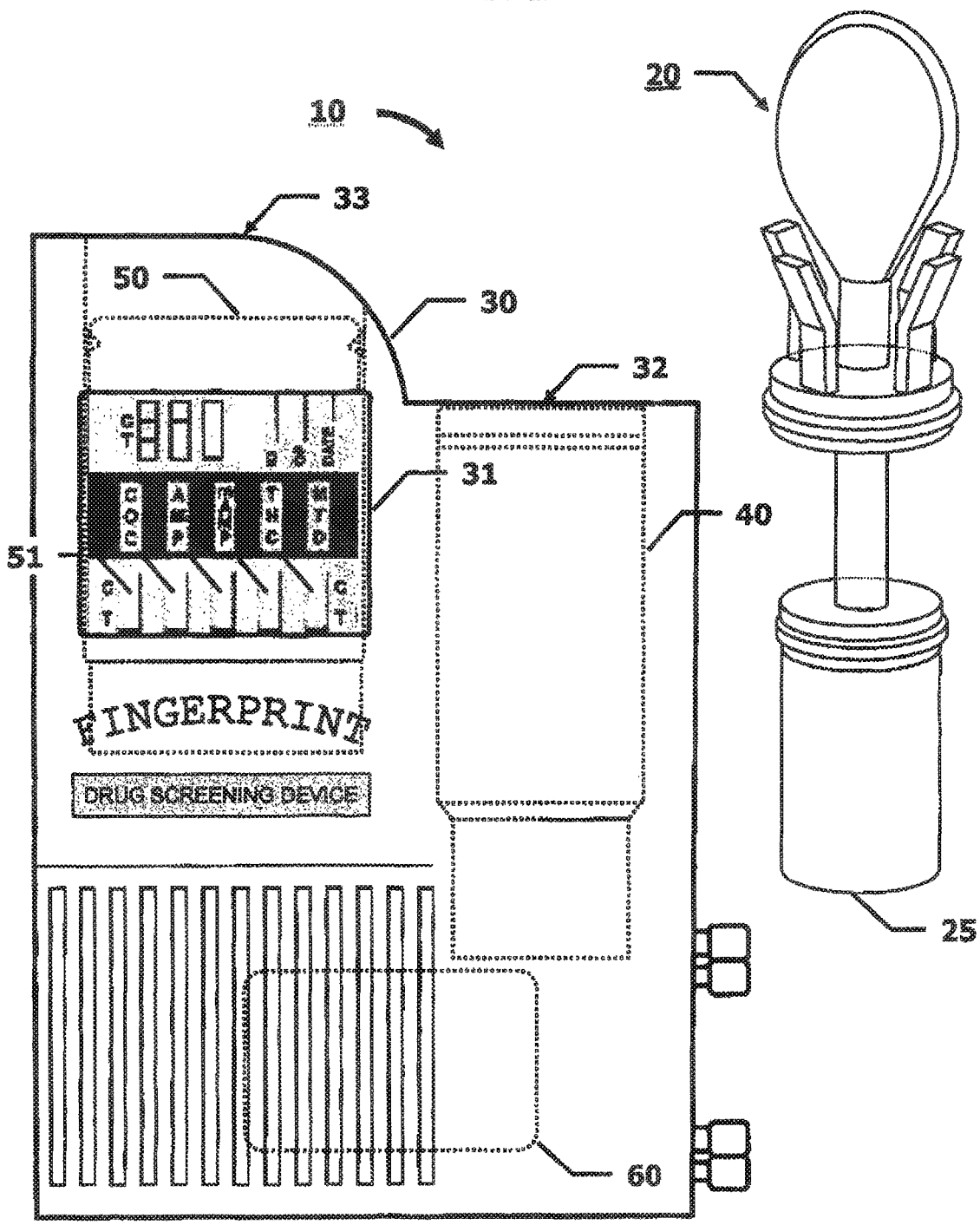
FIG. 1 depicts a front view of a fluid collection and analyte testing device in accordance with an embodiment of the present invention.
Figure 2:
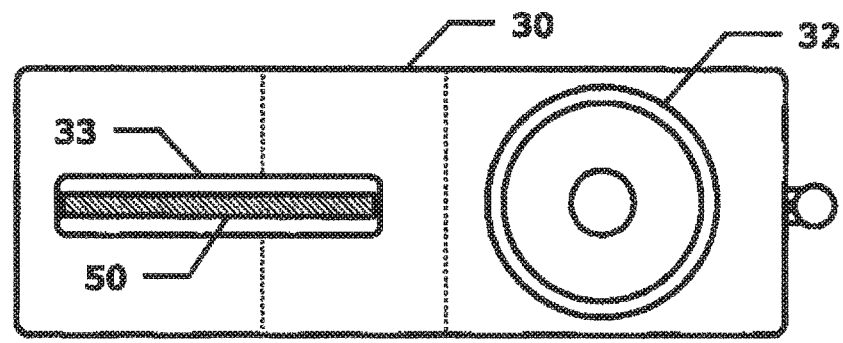
FIG. 2 depicts a top view of a fluid collection and analyte testing device in accordance with an embodiment of the present invention.
Figure 3:
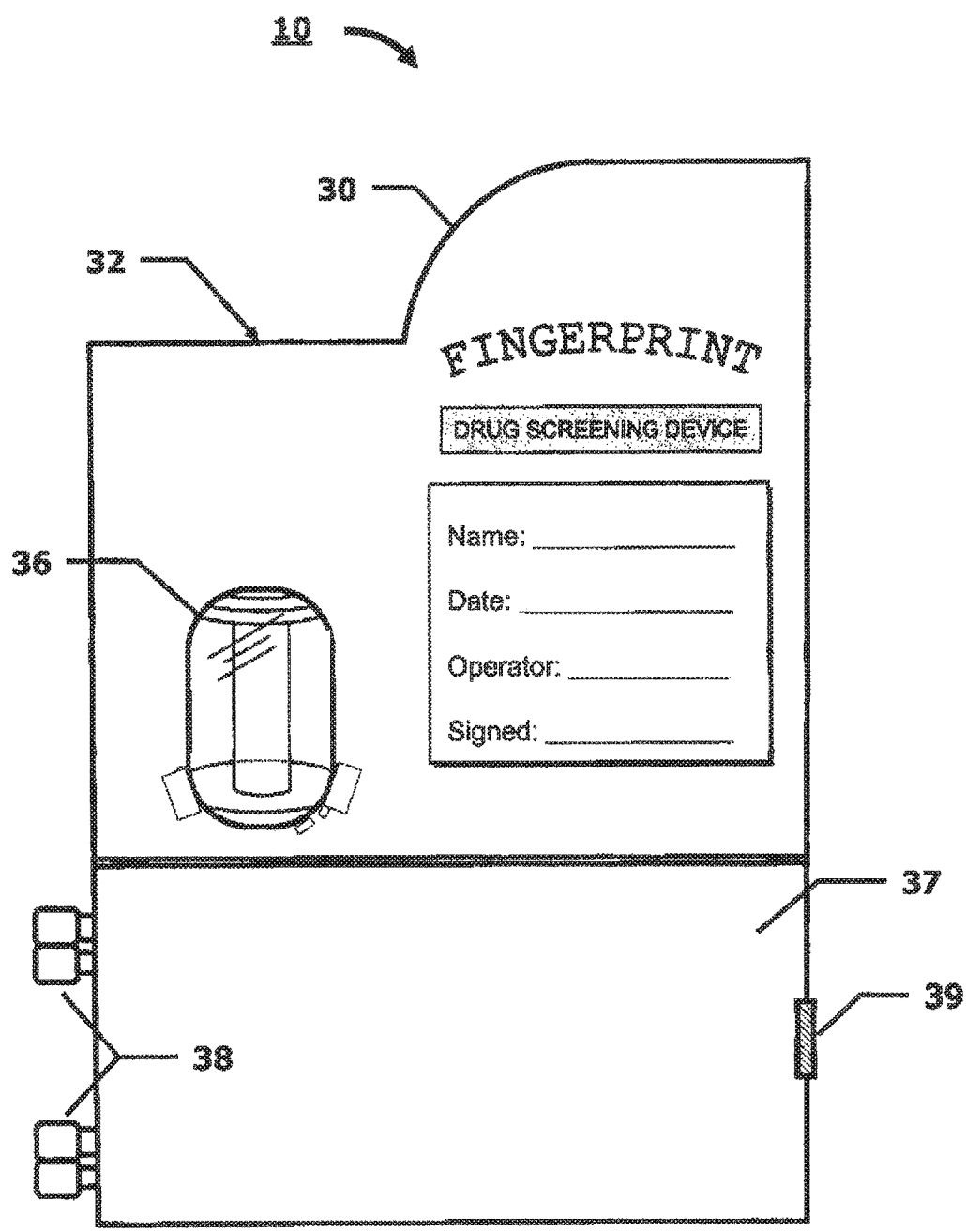
FIG. 3 depicts a back view of a fluid collection and analyte testing device in accordance with an embodiment of the present invention.
Figure 4:
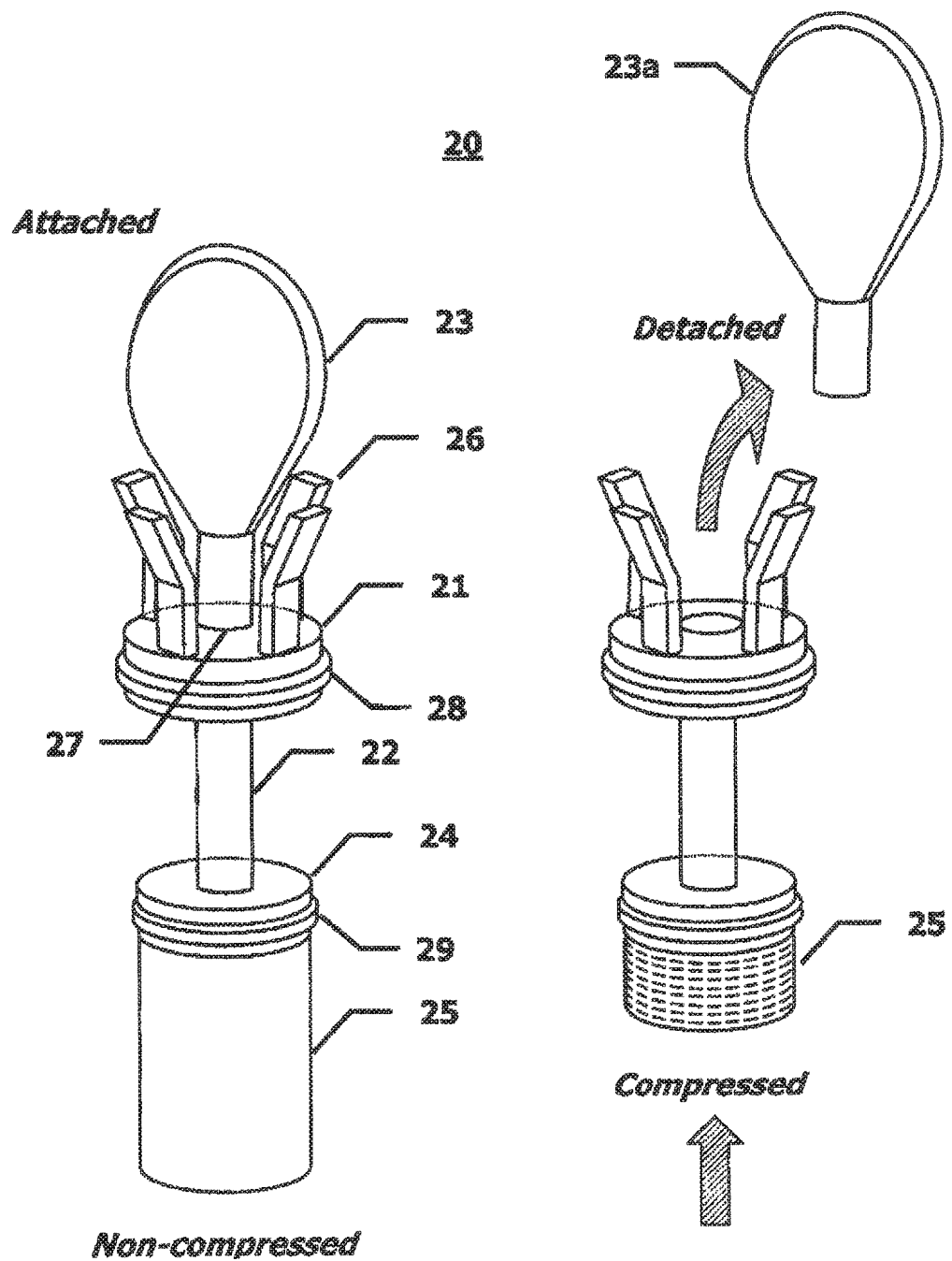
FIGS. 4A and 4B depict two perspective views of a fluid collector in accordance with an embodiment of the present invention.
Figure 5:
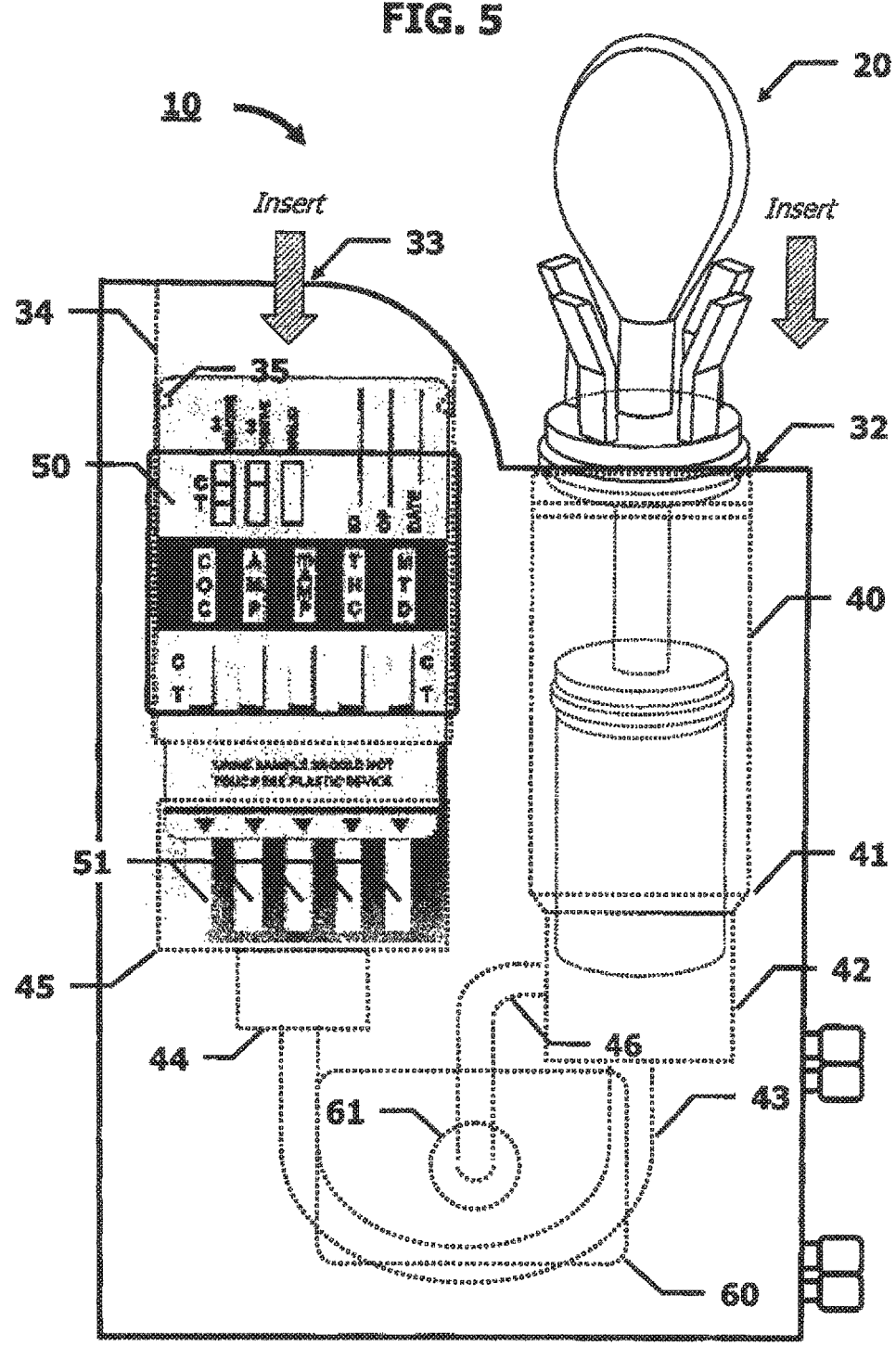
FIG. 5 depicts a front view of a fluid collection and analyte testing device in accordance with an embodiment of the present invention.

An embodiment of the present invention provides an analyte screening device which includes a rapid screening, lateral flow chromatographic immunoassay for the simultaneous, qualitative or quantitative detection of analytes in a fluid sample. For example, without limitation, the fluid sample may be saliva, urine, blood, mucus, water, or fluid extract of a solid or a semi-solid, for example stool or mucus or liquid biopsy. The fluid sample may also be an environmental sample, for example, without limitation, soil, dust, water, plant matter, insect, animal matter, or a fluid extract of any of the foregoing. The fluid sample may also be a food or beverage, for example, without limitation, a liquid beverage, a liquid-containing food, or a fluid extract of a solid, semi-solid or powdered food or beverage. The fluid sample may also contain genomic or proteomic material for testing and analysis.

An embodiment of the invention includes at least one membrane test strip, in fluid communication with a sample receiving member, able to indicate the presence or absence of at least one analyte above or below a threshold concentration in the fluid sample using a lateral flow chromatographic assay.

In an embodiment of the invention, the lateral flow chromatographic assay is a competitive assay, in which an analyte in the fluid sample competes with a competitor for binding with an anti-analyte antibody. For example, the anti-analyte antibody may be labeled, and the competitor may be immobilized in the test region of the membrane test strip. After the fluid sample reaches the dye region, it encounters the labeled anti-analyte antibody. If the analyte is present in the fluid sample above a predetermined threshold concentration, the analyte will saturate the binding sites of the labeled anti-analyte antibody; otherwise, some or the entire labeled anti-analyte antibody remains free to bind the competitor. As the fluid sample migrates along the membrane test strip by capillary action, it carries the labeled anti-analyte antibody along until it reaches the test region. The test region contains the immobilized competitor, which may be the analyte, fragments of the analyte, epitopes of the analyte, molecular mimics of the analyte, anti-idiotypic antibodies, or any other molecule able to compete with the analyte for binding to the anti-analyte antibody. If the analyte is present above the predetermined threshold concentration, the labeled anti-analyte antibody is saturated and does not bind the immobilized competitor, resulting in no signal in the test region; otherwise, the anti-analyte antibody is unsaturated and can bind to the competitor, resulting in a signal in the test region.

Thus, according to an embodiment of the invention employing a competitive assay, an analyte-negative fluid sample (containing lower than the predetermined concentration of the analyte) will generate a line in the test region due to capture of the labeled anti-analyte antibody, whereas an analyte-positive fluid specimen will not generate a colored line in the test region because the analyte in the fluid sample will saturate the labeled antibody and thus prevent its capture in the test region.

In an embodiment of the invention, the lateral flow chromatographic assay is a sandwich assay, in which the analyte must be present for the labeled anti-analyte antibodies to be captured in the test region. For example, the analyte antibody may be a labeled antibody, and a second anti-analyte antibody may be immobilized in the test region. For example, after the fluid sample reaches the dye region, it encounters the labeled anti-analyte antibody. If the analyte is present in the fluid sample, it will bind at least a fraction of the labeled anti-analyte antibody. As the fluid sample migrates along the membrane test strip by capillary action, it carries the labeled anti-analyte antibody along until it reaches the test region. The test region contains an immobilized anti-analyte antibody, which may be reactive against a different epitope of the analyte than the labeled anti-analyte antibody. If the analyte is present in the fluid sample, it forms a scaffold through which the labeled antibodies are immobilized in the test region. The fraction of the labeled antibodies captured in the test region is thus determined by the concentration of analyte in the fluid sample. If the analyte of interest is present above a predetermined threshold concentration, a sufficient fraction of the labeled antibodies are captured, resulting in a visible signal in the test region; otherwise, an insufficient fraction of the antibodies are captured and no signal is visible in the test region.

Thus, according to an embodiment of the invention employing a sandwich assay, an analyte-positive fluid specimen will generate a colored line in the test region of the membrane test strip due to the capture of the labeled antibody in the test region, whereas an analyte-negative fluid sample will not generate a fine in the test region due to failure to capture the labeled antibody.

Embodiments of the invention include a positive control to indicate that the assay has functioned properly and is complete. For example, the dye region may include a labeled control protein, including without limitation a labeled control antibody, and the control region of the membrane test strip may contain an immobilized control agent able to capture the labeled control protein, such as an antibody or a control analyte. The control region may be located distal to each test region on the membrane test strip, such that the fluid sample will encounter each test region before encountering the control region. The reaction of the labeled control protein with the immobilized control agent produces a colored line in the control region, indicating that a proper volume of the fluid sample has been added and membrane wicking has occurred, and the assay has worked properly.

An embodiment of the invention concurrently tests for multiple analytes, for example by employing membrane test strips capable of testing multiple analytes concurrently (for example, by containing multiple anti-analyte antibodies in the dye region and having multiple compatible test region), and/or by employing multiple membrane test strips within the same apparatus. An embodiment of the invention includes both membrane test strips that employ a competitive assay and a sandwich assay, for example on different membrane test strips within the device and/or on the same membrane test strip within the device.

Embodiments of the invention may provide quantitative determination of the concentration of an analyte that is present in the fluid sample. For example, the apparatus may include multiple membrane test strips having varying amounts of an anti-analyte antibody, resulting in varying analyte sensitivity, such that the concentration of the analyte is indicated by which of the membrane test strips show or fail to show a colored line in the test region.

Antibodies

An embodiment of the invention employs antibodies for the detection of analytes. The term "antibody" (Ab) as used herein includes monoclonal antibodies, polyclonal antibodies, multispecific antibodies (for example bispecific antibodies), and antibody fragments, so long as they exhibit the desired activity. The term "monoclonal antibody" as used herein refers to an antibody obtained from a population of substantially homogeneous antibodies, that is, the individual antibodies comprising the population are identical except for possible naturally occurring mutations that may be present in minor amounts.

The terms "labeled antibody" and "labeled control protein" refer to an antibody or protein that is conjugated directly or indirectly to a label. The label is a detectable compound or composition that may be detectable by itself, Including without limitation a dye, colloidal metal (including without limitation colloidal gold), radioisotope, or fluorescent compound, or, in the case of an enzymatic label, may catalyze chemical alteration of a substrate compound or composition which is detectable, or any combination of the foregoing.

Analytes

According to an embodiment of the invention, the apparatus includes a device for testing a fluid sample for the presence of analytes. The present invention contemplates testing for any analyte. Without limitation, analytes that may be tested for include drugs of abuse or their metabolites, analytes indicating the presence of an infectious agent or product of an infectious agent, allergen, pollutant, toxin, contaminant, analyte with diagnostic or medical value, antibody against any of the foregoing, and any combination thereof.

According to an embodiment of the invention, analytes that may be tested for include drugs of abuse and their metabolites, including without limitation 7-acetaminoclonazepam, alkyl nitrites, alpha-hydroxyalprazolam, alprazolam, 2-amino-2'-chloro-5-nitrobenzophenone, 7-aminoclonazepam, 7-aminonitrazepam, amitriptyline, amobarbital, amoxapine, amphetamine, anabolid steroids, androgen, androstadienone, aprobarbital, atropine, barbiturates, benzodiazepines, benzoylecgonine, benzylpiperazine, boldenone undecylenate, 4-bromo-2,5-dimethoxyphenethylamine, bovine growth hormone, buprenorphine, butabarbital, butalbital, butripryline, 4-chlordehydromethyltestosterone, chloroform, clomipramine, clonazepam, clostebol, cocaethylene, cocaine, codeine, codeine-6-glucuronide, cotinine, dehydroepiandrosterone, desipramine, desmethyldiazepam, desoxymethyltestosterone, dexmethylphenidate, dextroamphetamine, dextromethorphan, dextropropoxyphene, dextrorphan, 2,5-diamino-2'-chlorobenzophenone, diamorphine, diazepam, dibenzepin, dihydrotestosterone, dimenhydrinate, 2,5-dimethoxy-4-(n)-propylthiophenethylamine, 2,5-dimethoxy-4-ethylphenethylamine, 2,5-dimethoxy-4-iodophenethylamine, dimethyl ether, dimethyltryptamine, dimethyltryptamine, diphenhydramine hydrochloride, dosulepin hydrochloride, dothiepin hydrochloride, doxepin, drostanolone, ecgonine, ecgonine methyl ester, ephedrine, ergine, estren, 5-estrogen, ethyl-5-(1'-methyl-3'-carboxypropyl)-2-thiobarbituric acid, 5-ethyl-5-(1-'-methyl-3'-hydroxybutyl)-2-thiobarbituric acid, ethylestrenol, ethylphenidate, fentanyl, flunitrazepam, fluoxymesterone, furazabol, gamma-hydroxybutyrate, 1-(beta-D-glucopyranosyl) amobarbital, growth hormone, heroine, hexabarbital, human chorionic gonadotropin, human growth hormone, hydrocodone, hydromorphone, (+)-3-hydroxy-N-methylmorphinan, 3-hydroxy clonazepam, 11-hydroxy-tetrahydrocannabinol (11-hydroxy-THC), 3'-hydroxyamobarbital, p-hydroxyamphetamine, p-hydroxynorephedrine, imipramine, iprindole, kava, ketamine, levomethylphenidate, lofepramine, lorazepam, lorazepam-glucuronide, lysergic acid diethylamide, meperidine, mescaline, mestanolone, mesterolone, metachlorophenylpiperazine, methadone, methamphetamine, methandrostenolone, methcathinone, 3,4-methylenedioxyamphetamine, methenolone, methenolone enanthate, methylenedioxymethamphetamine (ecstasy), methylphenidate, methylphenobarbital, methyl testosterone, mibolerone, (+)-3-morphinan, morphine, nandrolone, nicotine, nitrazepam, N-methyl-diethanciamine, norbolethone, norcodeine, norethandrolone, norketamine, nortriptyline, opiates, opipramol, opium, oxabolone opionate, oxandrolone, oxazepam, oxycodone, oxymetholone, oxymorphone, pentobarbital, phencyclidine, phenethylamines, phenobarbital, 4-phenyl-4-(1-piperidinyl)-cyclohexanol, 1-phenyl-1-cyclohexene, phenylacetone, 5-[N-(1-phenylcyclohexyl)]-aminopentanoic acid, 1-(1-phenylcyclohexyl)-4-hydroxypiperidine, piperidine, protriptyline, psilocin, psilocybin, quinolone, salvinorin A, scopolamine, secobarbital, sodium thiopental, stanozolol, telbutal, temazepam, testosterone, testosterone proprionate, tetrahydrocannabinol (THC), THC-COOH, tetrahydrogestrinone, toluene, trenbolone, tricyclic antidepressant, 3-trifluoromethylphenylpiperazine, trimipramine, tryptamines, or any combination thereof. The minimum concentration level at which the presence of any particular drug or metabolite is detached may be determined by various industry minimum standards, such as, for example, the National Institute on Drug Abuse (NIDA), the Substance Abuse & Mental Health Services Administration (SAMHSA), and the World Health Organization (WHO).

According to an embodiment of the invention, analytes that may be tested for include infectious agent or the products of an infectious agent, including without limitation *Acanthamoeba*, Adenovirus, aflatoxin, alimentary mycotoxlcoses, altertoxin, amoeba, *Anisakis, Ascaris lumbricoides*, Avian Influenza, *Bacillus anthracis, Bacillus cereus* or its toxin, bacteria, bovine spongiform encephalopathy prioris, *Brucella*, Caliciviridae, *Calymmatobacterium granulomatis, Campylobacter, Campylobacter jejuni, Candida, Candida albicans, Cephalosporium*, Chagas, Chikungunya, *Chlamydia trachomatis*, chronic wasting disease prions, Citrinin, *Chlamydia, Clostridium difficile* GDH or its toxin, *Clostridium botulinum* or its toxin, *Clostridium perfringens, Corynebacterium ulcerans, Coxiella burnetii*, Creutzieldt-Jakob disease prions, Crimean-Congo Fever, *Cryptococcus neoformans, Cryptosporidium, Cryptosporidium parvum* Cycloplazonic acid, *Cyclospora cayetanensis*, Cytochaiasin, Cytomegalovirus, Dengue, Diphyilobothrium, Dysentery, *Escherichia coli*, Ebola, endotoxin, *Entamoeba histolytica*, Enterovirus, Ergopeptine alkaloid, Ergot alkaloid, Ergotamine, *Escherichia coli* O157, *Eustrongylides, Fasciola hepatica*, fatal familial insomnia prions, flatworm, *Francisella tularensis*, Fumitremorgin B.sub.1 Fumonisin, *Fusarium*, Fusarochromanone, genital warts, Gerstmann-Straussler-Scheinker syndrome prions, *Giardia, Giardia lamblia*, Granuloma inguinale, *H Pylori*, H7 enterohemorrhagic, *Haemophilus ducreyi*, HCV, *Helicobacter pylori*, Hepatitis, Hepatitis A, Hepatitis B, Hepatitis C, Hepatitis D, Hepatitis E, Hepatitis E, herpes simplex virus, *Histoplasma capsulatum*, HIV, HIV-1, HIV-2, human papillomavirus, influenza, influenza A, influence B, Kaposi's sarcoma-associated herpesvirus, Kojic acid, kuru prions, Lassa Fever, *Legionella, Listeria monocytogenes*, Lolitrem alkaloids, lower respiratory infections, Lyme IgG, Lyme IgM, Malaria, Marburg Hemorrhagic Fever, Measles, Methicillin-resistant *Staphylococcus aureus* or its toxin, Meningococcal, molluscum, Moniliformin, mononucleosis, mycobacteria, *Mycobacterium tuberculosis, Mycoplasma, Mycoplasma hominis*, Mycotoxins, *Myrothecium, Nanophyetus, Neisseria gonor-* rhoea, nematode, Nivalenol, Norovirus, Oohratoxins, Oosporeine, parasite, Patulin, Paxilline, Penitrem A, Phomopsins, Plague, *Plasmodium*, Platyhelminthes, *Plesiomonas shigelloides*, Pneumococcus, *Pneumocystis jirovecii*, prions, protozoa, R.S.V., Rift Valley Fever, rhinovirus, Rotavirus, Rota-adenovirus, *Salmonella, Sarcocystis hominis, Sarcocystis sulhominis*, scrapple prions, sexually transmitted disease, *Shigella, Shigella*, Sporidesmin A, Stachybotrys, *Staphylococcus aureus* or its toxin, Sterigmatocystin, *Streptococcus, Streptococcus agalactiae, Streptococcus pneumoniae, Streptococcus pyogenes*, Syphilis, *Taenia saginata, Taenia solium*, tapeworm, *Tenia solium*, Tetanus, Tinea, *Toxoplasma gondii, Tremorgenic mycotoxins, Treponema pallidum, Trichinella spiralis, Trichoderma, Trichomonas vaginalis*, Trichothecene, *Trichuris trichlura*, Tuberculosis, *Trypanosoma cruzi*, Typhoid, *Ureaplasma urealyticum*, Verrucosidin, Varruculogen, *Vibrio cholerae* non-O1, *Vibrio cholerae* O1, *Vibrio-parahaemolyticus, Vibrio vulnificus*, viruses, yeast infections, Yellow fever, *Yersinia enterocolitica, Yersinia pseudotuberculosis*, Zearalenois, Zearalenone, antibodies against any of the foregoing, or any combination thereof.

According to an embodiment of the invention, the analytes to be tested for include allergens, including without limitation *aesculus*, aider, almonds, animal products, arternisia vulgaris, beans, bet sting venom, birch, calyx, cat dander, celeriac, celery, *Chenopodium album*, cockroach, corn, dander, dong dander, drugs, dust mite excretion, egg albumen, eggs, Fei d 1 protein, fruit, fur, grass, hazel, hornbeam, insect stings, latex, legumes, local anaesthetics, maize, metal, milk, mold spores, mosquito saliva, mouse dander, nettle, *olea*, peanuts, peas, pecans, penicillin, Plant pollens, *plantago, platanus*, poplar, pumpkin, ragweed, rat dander, ryegrass, salicylates, seafood, sesame, sorrel, soy, soybeans, sulfonamides, *tilia*, timothy-grass, tree nuts, trees, wasp sting venom, weeds, wheat, willow, antibodies against any of the foregoing, or any combination thereof.

According to an embodiment of the invention, the analytes to be tested for include pollutants, toxins, and contaminants, including without limitation 1,2-Dibromoethane, acrylamide, aldehydes, arsenic, artificial growth hormone, asbestos, benzene, benzopyrene, carcinogens, dichloro-diphenyl-trichloroethane, formaldehyde, kepone, lead, mercury, methylmercury, nitrosamines, N-nitroso-N-methylurea, organochlorine insecticides, pesticides, polychlorinated biphenyls, polychlorinated dibenzofurans, polychlorinated dibenzo-p-dioxins, recombinant bovine growth hormone, recombinant bovine somatotropin, toluene, vinyl chloride, antibodies against any of the foregoing, or any combination thereof.

According to an embodiment of the invention, the analytes to be tested for include analytes with diagnostic or medical value, including without limitation acid phosphatase, active-B12, AFP, Alanine Aminotransferase, Alanine Aminotransferase, Albumin, Albumin BCG, Albumin BCP, ALT, Alkaline Phosphatase, Alpha-1 Antitrypsin, Alpha-1 Glycoprotein, Amikacin, Ammonia, Amylase, Anti-CCP, Anti-Tg, Anti-TPO, Apolipoprotein A1, Apolipoprotein B, ASO, Asparate Aminotransferase, Aspartate Aminotransferase, AST, B12, Beta2 Microglubulin, Beta2 Microglobulin, BNP, CA 125, CA 125 II, CA 15-3, CA 19-9 XR, Calcium, Calprotectin, Carbamazepine, Carbon Dioxide, CEA, Ceruloplasmin, Cholesterol, CK-MB, Complement C3, Complement C4, Cortisol, C-Peptide, C-Reactive Protein, Creatine Kinase, Creatinine, CRP Vario, Cyclosporine, Cyclosporine and Metabolite-Whole Blood, Cyclosporine Monoclonal-Whole Blood, D-Dimer, DHEA-S, Digitoxin, Digoxin, Digoxin, Digoxin II, Digoxin III, Direct Bilirubin, Direct LDL, Estradiol, Fatty acid-binding protein, Ferritin, FLM II, Folate, Free Carbamazepine, Free Phenytoin, Free PSA, Free T3, Free T4, Free Valproic acid, FSH, Gamma-Glutamyl Transferase, Gentamicin, Glucose, Glycated Hemoglobin, Haptoglobin, hCG, Hemoglobin, Homocysteine, HS CRP, ICT CI-, IGFBP-1, Immunoglobulin, Immunoglobulin A, Immunoglobulin E, immunoglobulin G, Immunoglobulin M, Insulin, Intact PTH, Iron, Ischemic heart disease (Cardiac Markers), K+, Kappa Light Chain, Lactate Dehydrogenase, Lactic acid, Lambda Light Chain, LH, Lidocaine, Lipase, Lithium, Lp, LS Ferritin, magnesium, metabolites, Methotrexate II, Microalbumin, MPO, Myoglobin, Na+, N-Acetyl-procainamide, neonatal Bilirubin, NGAL, P-Amylase, Pepsinogen I, Pepsinogen II, Phenobarbital, Phenytoin, Phosphorus, Prealbumin Procainamide, Progesterone, Prolactin, Protein-Energy Malnutrition, Quinidine, Rheumatoid Factor, SHBG, Sirolimus, STAT CK-MB, T4, Tacrolimus, Tacrolimus II, Testosterone, Tg, Theophylline, Theophylline II, TIBC, TIMP-1, Tobramycin, Total Bilirubin, Total Estriol, Total Protein, Total PSA, Total T3, Total T4, Transferrin, Triglycerides, Troponin-1, Troponin-I ADV, TSH, T-Uptake, UIBC, Ultra HDL, Urea Nitrogen, Uric Acid, Urine/CSF Protein, Valproic Acid, Vancomycin, Vancomycin II, Vitamin D, antibodies against any of the foregoing, or any combination thereof.

Receiving Member

According to an embodiment or the invention, the apparatus includes a receiving member, having an opening to receive a fluid sample, For example, the receiving member may be dimensioned to receive a fluid collector. In an embodiment of the invention, the receiving member may be in fluid communication with other components of the apparatus, for example at least one membrane test strip, sample retention member, and/or an Immunoassay-based fingerprint acquisition pad, through channels, for example tubes, piping, channels molded or carved into the apparatus, or any other suitable structure, made of any suitable material, for example plastic, ceramic, metal, glass, wood, rubber, polymer, fiber-reinforced polymer, or any combination thereof.

According to an embodiment of the invention, the channel or channels providing fluid communication between the components may have differing flow resistance, for example having channels, channel segments, or openings, that are narrower, wider, longer, or shorter than others, and/or having fluid paths with varying amounts of vertical rise or drop, such that the fluid channels within the device have varying degrees of flow resistance. For example, the channel that provides the fluid communication of the sample receiving member with the at least one membrane test strip may have greater flow resistance than the at least one channel that provides the fluid communication of the sample receiving member with the sample retention member, to ensure that a portion of the fluid sample is collected in the sample retention member.

In an embodiment of the invention, a single channel having multiple openings may connect the receiving member to each of the components of the apparatus with which it is in fluid communication, for example the at least one membrane test strip, sample retention member, and/or immunoassay-based fingerprint acquisition pad.

In an embodiment of the invention, the receiving member may include two or more chambers for receipt of a multi-pronged fluid collector, including but not limited to a dual-swab fluid collector. Components of the apparatus may be solely connected to one of the multiple chambers. For example, in a two chamber embodiment, one chamber may be solely connected to a sample retention member to ensure that a portion of the fluid sample is collected and stored without interaction of the other components of the apparatus.

An embodiment of the invention may accommodate fluids of varying viscosity, for example water, saliva, urine, blood, and liquids associated with genomics and proteomics. Generally, this is accomplished by varying the diameter of the channel or channels that provide the fluid communication of the sample receiving member with the other components of the apparatus, for example providing a wider channel diameter to accommodate a more viscous fluid.

In an embodiment of the invention, a channel dimensioned to be compatible with a fluid having the viscosity of water provides the fluid communication of the sample receiving member with the at least one membrane test strip and at least one channel dimensioned to be compatible with a fluid having the viscosity of water provides the fluid communication of the sample receiving member with the sample retention member.

In an embodiment of the invention, a channel dimensioned to be compatible with a fluid having the viscosity of urine provides the fluid communication of the sample receiving member with the at least one membrane test strip and at least one channel dimensioned to be compatible with a fluid having the viscosity of urine provides the fluid communication of the sample receiving member with the sample retention member.

In an embodiment of the invention, a channel dimensioned to be compatible with a fluid having the viscosity of saliva provides the fluid communication of the sample receiving member with the at least one membrane test strip and at least one channel dimensioned to be compatible with a fluid having the viscosity of saliva provides the fluid communication of the sample receiving member with the sample retention member.

In an embodiment of the invention, a channel dimensioned to be compatible with a fluid having the viscosity of blood provides the fluid communication of the sample receiving member with the at least one membrane test strip and at least one channel dimensioned to be compatible with a fluid having the viscosity of blood provides the fluid communication of the sample receiving member with the sample retention member.

In an embodiment of the invention, a channel dimensioned to be compatible with a fluid having the viscosity of mucus provides the fluid communication of the sample receiving member with the at least one membrane test strip and at least one channel dimensioned to be compatible with a fluid having the viscosity of mucus provides the fluid communication of the sample receiving member with the sample retention member.

In an embodiment of the invention, a channel dimensioned to be compatible with a fluid having the viscosity of liquid associated with cell separation provides the fluid communication of the sample receiving member with the at least one membrane test strip and at least one channel dimensioned to be compatible with a fluid having the viscosity of liquid associated with cell separation provides the fluid communication of the sample receiving member with the sample retention member.

In an embodiment of the invention, a channel dimensioned to be compatible with a fluid having the viscosity of liquid biopsy, such as proteomics or genomics, provides the fluid communication of the sample receiving member with the at least one membrane test strip and at least one channel dimensioned to be compatible with a fluid having the viscosity of liquid biopsy provides the fluid communication of the sample receiving member with the sample retention member. Proteomics is the study of proteins. Genomics is a branch of molecular biology concerned with the structure, function, evolution, and mapping of genomes.

In an embodiment of the invention, the receiving member may have an inner surface, for example a lower surface, that an absorbent material, such as an absorbent material present in a fluid collector, may be compressed against, thereby expelling the fluid sample from the absorbent material. For example, the absorbent material may be compressed directly between a compression member present on the fluid collector and the lower surface of the receiving member or the receiving member may provide structural support to facilitate compression of the absorbent material between a compression member and the housing that at least partially surrounds the absorbent material.

Sample Retention Member

According to an embodiment of the invention, the apparatus includes a sample retention member. The sample retention member may be used to securely contain a portion of the fluid sample, such as a split sample. The retained portion of the fluid sample may be used for further testing, for example for confirmation of a test result obtained using a membrane test strip, or to test for the presence or absence of other analytes in the fluid sample. The retained portion of the fluid sample may also be used for confirmation of the test subject's identity through analysis of a distinguishing feature thereof, including without limitation DNA, cells, proteomics, metals, and liquid biopsy.

According to one embodiment of the invention, the sample retention member includes an absorbent material, for example a pad or sponge, or made of woven or non-woven fibrous or fabric-like material, for example cellulose or a cellulose derivative, cotton, hydrophilic foam, wood pulp, polyvinyl alcohol fibers, or any combination thereof. The sample retention member may include an absorbent material that is part of the sample collection apparatus. The absorbent material may be surrounded by a barrier, such as a liquid-impermeable material, including without limitation plastic, ceramic, metal, glass, wood, rubber, polymer, fiber-reinforced polymer, or any combination thereof, to prevent the retained sample from leaking or evaporating. In an embodiment of the invention, the absorbent material may be removably attached to the apparatus to facilitate retrieval of the retained fluid sample. In an embodiment of the invention, the absorbent material may be accessed using a needle, for example by piercing a barrier surrounding the absorbent material. The retained sample may then be removed, for example, into a syringe attached to a needle, by means of withdrawal of the syringe to create suction.

According to an embodiment of the invention, the sample retention member includes a storage container defining a volume for storage of the fluid sample. In one embodiment of the invention, the sample retention member may be a vial made from a breakable or nearly unbreakable material, including without limitation glass, plastic, ceramic, metal, metal foil, wood, rubber, polymer, fiber-reinforced polymer, or any combination thereof. In an embodiment of the invention, the storage container may be accessed using a needle to pierce the wall of the storage container. For example, the storage container may include a pierceable member, such as a region of decreased wall thickness, and/or made of a soft, pierceable, or breakable material, including without limitation plastic, ceramic, metal, glass, metal foil, wood, rubber, polymer, fiber-reinforced polymer, or any combination thereof, that may be pierced. The retained sample may then be removed, for example, into a syringe attached to a needle, by means of withdrawal of the syringe to create suction. In an embodiment of the invention, the storage container may be removably attached to the apparatus, including without limitation, through a line of weakness that may allow the storage container to be broken free form the apparatus, through a threaded connection mechanism between the sample retention member and the fluid sample testing device, or through a twisting lock connection mechanism between the sample retention member and the fluid sample testing device.

According to an embodiment of the invention, the removable sample retention member may be linked to or coded consistently with the fluid sample testing device, including but not limited to, identical or related identification or serial numbers on both the sample retention member and the fluid sample testing device, identical or related bar code information on both the sample retention member and the fluid sample testing device, and the inclusion of radio frequency identification devices (RFID) on the sample retention member or the sample retention member and the fluid sample testing device. RFID incorporates the use of electromagnetic or electrostatic coupling in the radio frequency (RF) portion of the electromagnetic spectrum uniquely identify an object; such unique identification information may be information specific to the sample provider or information unique to the fluid sample testing device.

According to an embodiment of the invention, the sample retention member contains substances that facilitate a further use of the sample, including without limitation preservatives of stabilizers able to preserve sample integrity, for example substances able to inhibit microbial growth, kill microbes, prevent sample leakage, prevent sample evaporation, inhibit chemical or enzymatic degradation of substances in the sample, support survival of cells or other microbes in the sample, or any combination thereof.

According to an embodiment of the invention, the sample retention member may be bonded to a fingerprint acquisition pad. For example, such a bond may provide a safeguard against dissociation of the retained sample from the fingerprint.

According to an embodiment of the invention, the sample retention member may be in fluid contact solely with the sample receiving member and may not have any fluid contact with any other component of the apparatus.

The retained fluid sample may be used for further confirmation testing, including without limitation gas chromatography, liquid chromatography, mass spectrometry, liquid or gas chromatography with tandem mass spectrometry, polymerase chain reaction, DNA sequencing, Enzyme-Linked ImmunoSorbent Assay, Western Blotting, culturing for growth, or any combination thereof, using the retained fluid sample.

Fluid Collector

An embodiment of the apparatus comprises a fluid collector for collecting a fluid sample. The present invention contemplates collecting a sample from a specific subject, such as a human subject, or testing environmental samples, such as testing air, water, soil, or some other substance, or a food or beverage, or a liquid extract of any of the foregoing for example, without limitation. The fluid collector is operative associated with the apparatus. The fluid collector may be removably associated with the apparatus/affixed to the apparatus, or comprise multiple units of which one or more is affixed or removably associated with the apparatus.

In an embodiment of the invention, the fluid collector includes an absorbent material capable of absorbing a desired quantity of a fluid sample. The absorbent material may be made of any suitable material known to a person in the art, for example, without limitation, a pad or sponge, or woven or non-woven fibrous or fabric-like material, including without limitation cellulose or a cellulose derivative, cotton, hydrophilic foam, wood pulp, polyvinyl alcohol fibers, or any combination thereof. In an embodiment of the invention, the fluid collector includes a compression member, able to compress the absorbent material, that may be used to expel air from the absorbent material prior to collection of the fluid sample and/or encourage the fluid sample to flow into the absorbent material by creating suction as the compressed absorbent material returns to the uncompressed state. A compression member may also be used, for example, to compress the absorbent material and expel a fluid sample contained therein.

In one embodiment of the invention, the fluid collector includes multiple collection swabs. For example, a two-prong fluid collector with dual swabs may be implemented to collect the sample. In one embodiment, each swab of a multi-swab fluid collector may be selected based upon the specific swab collection characteristics. For example, in a dual-swab fluid collector, each swab may contain a material to assist in the collection of different samples such as the collection of different cell material A sufficiency indicator on the collector is contemplated. For example without limitation, a color indicator may either appear or disappear when a sufficient sample has been collected, for example when a sufficient volume has been absorbed to reach the location in the absorbent material where the sufficiency indicator is disposed. According to an embodiment of the invention, the sufficiency indicator may be operatively associated with the absorbent material and may protected from direct contact with the source of the fluid sample by a barrier, such as a transparent barrier, for example plastic or glass, such that the fluid sample will only reach the sufficiency indicator by passing into the absorbent material.

The sufficiency indicator color may be in the shape of a word or symbol that appears or disappears when a sufficient sample has been collected. For example, the sufficiency indicator may a diffusible dye, wherein dilution of the dye by the fluid sample causes a color to disappear, indicating that a sample of sufficient volume has been collected. In an embodiment of the invention, a combination of a non-diffusible and diffusible dye may be used together, such that the non-diffusible dye remains and provides an informative message when the diffusible dye disappears, for example the diffusible dye may form the letters "in" in the word "insufficient" such that the non-diffusible dye remains and forms the word "sufficient" when a sufficient sample has been collected.

The sufficiency indicator may be a pH-sensitive substance that changes color when the sample is encountered. For example, multiple pH sensitive indicators responding to different pH values may be preset, such that a color change is observed whether the sample is acidic, basic, or neutral. According to an embodiment of the invention, a pH-changing substance, such as an acid or base, may be disposed within the absorbent material, such that the sample will be of the correct pH to elicit the desired color change in the sufficiency indicator.

A closure member may be used. The closure member is capable of sealing the open end of a sample receiving member when the fluid collector is inserted into the open end of a sample receiving member. For example, the closure member may be dimensioned to fit closely in the opening in the open end of the receiving member, and the closure member or the open end of the receiving member may include a compressible material, including without limitation natural rubber such as vulcanized rubber, synthetic rubber such as neoprene or nitrite rubber, plastic, ceramic, or any combination thereof, disposed at the interface between the closure member and the opening in the open end of the sample receiving member, capable of creating a seal, such as an airtight or a watertight seal, when the sample receiving member receives the fluid collector.

After the fluid collector has been inserted into the sample receiving member, a device for securing the fluid collector within the sample receiving member is contemplated. The means for securing may prevent removal of the fluid collector from the sample receiving member after it has been inserted therein. The means for securing the fluid collector within the sample receiving member may include at least one projection extending from the fluid collector that cooperates with the at least one projection located on the inner surface of the sample receiving member, where such projections may include for example at least one locking tab and/or at least one annular ring. According to an embodiment of the invention, a closure member on the fluid collector may form a sufficiently secure closure as to constitute means for securing the fluid collector within the sample receiving member.

The sample receiving member may also include a tamper-evident seal, such that attempting to tamper with the contents of the apparatus will result in a visual indicator, for example by tears or breakage visible in an imprinted seal, for example tape or adhesive-backed foil having characters, symbols or a signature on a surface. Such a tamper-evident seal may be placed on the apparatus before its use, to create a visual confirmation that the intents of the apparatus have not been altered via the open end of the receiving member prior to testing, or after its use, to create a visual confirmation that the contents of the apparatus have not been altered via the open end of the receiving member subsequent to testing. According to an embodiment of the invention, the means for securing the fluid collector within the sample receiving member may constitute a tamper evident seal, in that attempted removal of the fluid collector from the sample receiving member after it has been inserted therein may result in visible damage to the apparatus.

According to an embodiment of the invention, the fluid collector includes a handle, for example made of wood, plastic, ceramic, or metal, and disposed, for example, at the end distal to the absorbent material. The handle may be removably attached, for example through an interference fit, adhesive, glue, or epoxy, that breaks or separates when the handle is twisted and/or pulled, or by a structure that allows the handle to be broken away, for example, a line of weakness.

The fluid collector may include a housing that at least partially surrounds the absorbent material. The housing may have multiple openings to allow the fluid sample to be absorbed by and expressed from the absorbent material. The openings in the housing may contain filtration members able to strain particulates from the fluid sample, resulting in reduction of the number of particulates that enter the absorbent material. The fluid collector may include a compression member able to compress the absorbent material against the housing. For example, the housing may be slideably coupled to a compression member with the absorbent material disposed between the compression member and an inner surface of the housing, such that the absorbent material may be compressed by movement of the compression member towards an inner surface of the housing. An embodiment of the invention includes means for securing the absorbent material in the compressed state, including without limitation cooperating threads, projections, and/or grooves operatively associated with the compression member and the housing. The absorbent material may be released from the compressed state before, concurrently with, or after encounter with the fluid sample, facilitating entry of the fluid sample into the absorbent material as the absorbent material returns to the relaxed state, creating suction. For example, the absorbent material may be operatively associated with a spring, such that compression of the absorbent material results in compression of the spring, and when compression is released the spring assists return of the absorbent material to the uncompressed state.

In an embodiment of the invention, the fluid collector is operatively associated with the lid of a fluid container including without limitation a urine cup. For example, the absorbent material may be disposed on the inner side of the lid, such that attachment of the lid to the fluid container results in contact between the absorbent material and a fluid sample. In certain embodiments of the invention, a portion of the fluid collector including the lid may be removably associated with a portion of the fluid collector including the absorbent material, allowing the absorbent material to be separated from the lid. The operative association of the fluid collector with the lid may include means for arresting the rotation of part of the fluid collector relative to the lid, including without limitation cooperating projections present on one member and grooves or slots present on the other member, for example to facilitate release of means by which the absorbent material is fixed in the compressed state.

Saliva Producing Substances

Use of a saliva producing substance is contemplated by the present invention. Saliva producing substances elicit or increase saliva production in the test subject. For example, without limitation, the saliva producing substance may sugars, salts, acids, or any combination thereof. In an embodiment of the invention, the saliva producing substance may be associated with a fluid collector, for example located on or in the absorbent material or the housing. In an embodiment of the invention, the saliva producing substance may be separated from the fluid collector, for example in the form of a gum, candy, or powder, for administration to the test subject before, during or after the fluid collector is inserted into the test subject's mouth.

For example, without limitation, the sugar may be a monosaccharide, a disaccharide, a trisaccharide, an oligosaccharide, a polysaccharide, acarbose, allose, altrose, amylose, arabinose, calibiose, cyclodextrin, alpha-cyclodextrin, beta-cyclodextrin, gamma-cyclodextrin, deoxyglucose, dextrin, dihydroxyacetone, erythrose, erythrulose, ficoli, fructo-oligosaccharides, fructose, galacto-oligosaccharides, galactose, gentiobiose, glucosamine, glucose, glyceraldehyde, glycogen, gulose, idose, inositol, inulin, isomaltose, lactose, lyxose, maltose, maltosyl-cyclodextrin, malt-trifose, mannan-oligosaccharides, mannoheptulose, marinose, melexltose, mannitol, psiccae, raffinose, ribitol, ribose, ribulose, sedoheptulose, sorbitol, sorbose, sucrose, tagatose, talose, threose, trehalose, xylose, xylulose, or any combination thereof.

For example, without limitation, the salt may an inorganic salt, organic salt, acid salt, alkali salt, neutral salt, or amino acid salt, or any combination thereof. The salt may include a cation and an anion, for example without limitation thereto, the cation may be aluminum, ammonium, barium, beryllium, calcium, cesium, chromium(II), chromium(III), chromium(IV), cobalt(II), cobalt(III), copper(I), copper(II), copper(III), gallium, helium, hydrogen, hydronium, iron(II), iron(III), lead(II), lead(IV), lithium, magnesium, manganese (II), manganese(III), manganese(IV), manganese(VII), nickel(II), nickel(III), nitronium, potassium, pyridinium, silver, sodium, strontium, tin(II), tin(IV), zinc, or any combination thereof, and an anion may be acetate, amide, tartrate, borate, bromate, bromide, carbonate, chlorate, chloride, chlorile, chromate, citrate, cyanate, dichromate, dihydrogen phosphate, fluide, formate, glutamate, hydride, hydrogen carbonate, hydrogen oxalate, hydrogen phosphate, hydrogen sulfate, hydrogen sulfite, hydroxide, hypobromite, hypochlorite, iodate, iodide, nitrate, nitride, nitrite, oxalate, oxide, perchlorate, permanganate, peroxide, phosphate, phosphide, phosphite, pyrophosphate, sulfate, sulfide, sulfite, telluride, thiocyanate, thiosulfate, or any combination thereof. For example, according to an embodiment of the invention, the salt may be sodium chloride or potassium chloride.

The acid may be any suitable acid known to a person skilled in the art, for example acetic acid, acrylic acid, adipic acid, alginic acid, alkanesulfonic acid, amino acid, ascorbic acid, benzoic acid, boric acid, butyric acid, carbonic acid, carboxylic acid, citric acid, fattys acid, folic acid, formic acid, fumaric acid, gluconic acid, hydriodic acid, hydrobromic acid, hydrochloric acid, hydroquinosulfonic acid, isoascorbic acid, lactic acid, maleic acid, malic acid, malonic acid, methanesulfonic acid, nitric acid, oxalic acid, p-toluenesulfonic acid, para-bromophenylsulfonic acid, phosphoric acid, propionic acid, salicyclic acid, stearic acid, succinic acid, sulfuric acid, tannic acid, tartaric acid, thioglycolic acid, toluenesulfonic acid, uric acid, or any combination thereof.

Fingerprint Identification

An embodiment of the present invention includes a fingerprint pad to provide identification of an individual associated with the test, such as the test subject, test administrator, and/or one or more witnesses. The fingerprint pad may employ any suitable fingerprinting methodology, for example, without limitation, ink-based, immunoassay-based, electronic, semi-inkless, or inkless. In an embodiment of the invention, the fingerprint pad may be able to collect multiple fingerprints, for example having multiple fingerprint pads, having one fingerprint pad of sufficient size to accommodate multiple fingerprints, or having an electronic fingerprint pad.

The fingerprint pad may be an ink-based fingerprint pad. An embodiment of the invention includes a dispenser able to dispense an ink that can elicit a signal in the ink-based fingerprint pad. The fingerprint pad may also be inkless or semi-inkless, for example requiring no ink or compatible with an activator that appears transparent on the subject's skin, is readily cleaned off the subject's skin, or readily disappears, for example, when the subject's hands are rubbed together. According to an embodiment of the invention, the inkless fingerprint pad may be immunoassay-based, for example as described within U.S. Pat. No. 6,352,663 to Raouf A. Guirguis, issued Mar. 5, 2002 (the "'863 patent"), and U.S. Pat. No. 5,244,815 to Raouf A. Guirguis, issued Sep. 14, 1993 (the "'815 patent"), which are incorporated herein by reference in their entirety. The immunoassay-based fingerprint pad may or may not be in fluid communication with a sample receiving member. Other embodiments of the invention may incorporate various features of the embodiments disclosed within the '863 and '815 patents. In embodiment of the invention having an inkless or semi-inkless fingerprint pad that requires an activator to elicit a signal, the apparatus may also include a dispenser to dispense the activator. According to an embodiment of the invention, the fingerprint pad may have a surface, such as an absorbent or adhesive surface, able to gather sweat, oils, and/or skin cells when a finger is pressed against it, that may require further processing to permit clear visualization of the fingerprint.

According to an embodiment of the invention, an inkless fingerprint pad may be an electronic fingerprint pad, including without limitation an optical scan fingerprint reader or a solid-state fingerprint reader. An embodiment of the invention includes a memory element, including without limitation volatile or non-volatile memory, for example a hard disk, floppy disk, magnetic tape, optical disk, flash memory, holographic memory, EEPROM, RAM, DRAM, SDRAM, or SRAM coupled to the fingerprint pad for storage of one or more fingerprints. According to an embodiment of the invention, the electronic fingerprint pads may have electrically charged surface elements, wherein portions of the surface are electrically discharged upon contact with the finger surface, such as the ridges of the finger surface, such that the fingerprint is recorded in the pattern of discharged elements, whereby the fingerprint pattern may be stably stored within the surface for a time after it is created until it is read, for example through connection of the apparatus with an external device, including without limitation a base station. An embodiment of the invention include means of transmission of the captured fingerprint, for example to an external device or network, including without limitation through a hard-wired connection, for example employing wires, cables, or a docking station or docking connector, for employing a connection including without limitation USB, IEEE 1394, serial, parallel, or SCSI, or a wireless connection, for example employing infrared, RF, IEEE 802.11, Bluetooth, IEEE 802.15, or Wi-Fi.

In an embodiment of the invention, a cover encloses the fingerprint acquisition pad. The cover may be secured using various mechanisms, for example, without limitation, a tab-and-slot connector, latch, spring latch, adhesive tape, or security tape. The cover may be secured prior to fingerprint acquisition and/or after fingerprint acquisition.

FIGS. 1-5 depict a fluid collection and analyte testing device in accordance with an embodiment of the present invention. Analyte screening device 10 includes a fluid collector 20, to collect a fluid sample from a test subject, and a housing 30 to test and retain the fluid sample. The housing 30 contains a collection chamber 40, to receive the fluid collector 20 through an opening 32, at least one membrane test strip 51, to indicate the presence or absence of at least one analyte, and an immunoassay-based fingerprint acquisition pad 60 to positively identify an individual associated with the test. The collection chamber 40 is in fluid communication, with the membrane test strips 51 and the immunoassay-based fingerprint acquisition pad 60.

Referring still to FIGS. 1-5, the fluid collector 20 receives a fluid sample from a test subject and temporarily stores the fluid sample until it is transferred to the housing 30. Generally, any material capable of acquiring and storing a fluid sample may be used. A sponge 25 is attached to one end of the fluid collector 20 to absorb, and temporarily store, the fluid sample. The sponge 25 may be saturated with a saliva-producing substance. After the fluid sample has been collected, the fluid collector 20 is inserted into the collection chamber 40 through the opening 32, and the fluid sample is expelled by compressing the sponge 25 against the bottom surface of the lower portion 42 of the collection chamber 40, thereby releasing the entrapped fluid into the apparatus.

Referring still to FIGS. 1-5, the fluid collector 20 includes a central shaft 22, a disk 21, disposed at the upper end of the central shaft 22, a disk 24, disposed at the lower end of central shaft 22, and a handle 23 attached to the upper surface of the disk 21. The diameter of disk 21 is slightly larger than the diameter of disk 24. Additionally, sealing rings 28 and 29 may be attached to the outer circumference of disks 21 and 24, respectively. Generally, the dimensions of disks 21 and 24, and sealing rings 28 and 29, comport with the interior dimension of collection chamber 40 in order to prevent fluid from escaping through the opening 32. Sponge 25 is attached to the lower surface of disk 24 and is dimensioned to be slightly smaller in diameter than disk 24 to allow for radial expansion within the lower portion 42 of the collection chamber 40 when the sponge 25 is under compression.

Referring still to FIGS. 1-5, as is discussed in more detail below, the fluid collector 20 becomes secured within the collection chamber 40 after the fluid collector 20 is inserted into the collection chamber 40 to a predetermined depth. If desired, handle 23*a* may then be broken away from the upper surface of disk 21. The analyte screening device 10 also includes a window 36 through which the secured fluid collector 20 may be viewed. The cover 37 encloses immunoassay-based fingerprint acquisition pad 60, and is attached to the housing 30 by the hinges 38. The cover 37 may be secured after the fingerprint of the test subject has been acquired, using various locking mechanisms, including without limitation a tab-and-slot arrangement, or security tape. Further confirmation testing may be performed, using the secured fluid sample. Access to the fluid sample may be obtained, for example, by simply removing the immunoassay-based fingerprint acquisition pad 60 to expose adapter 61 and tube 46, by puncturing the immunoassay-based fingerprint acquisition pad 60 with a needle to access adapter 61 and tube 48.

Referring still to FIGS. 1-5, the test cartridge 50, containing the membrane test strips 51, may be inserted into a test cartridge chamber 34 through an opening 33. Advantageously, different versions of the test cartridge 50 may be developed to test different combinations of analytes, thereby allowing the test administrator to select the appropriate analyte test suite at the test site. The test cartridge chamber 34 includes a locking mechanism 35 to secure the test cartridge 50 within the test cartridge chamber 34, thereby preventing the removal of the test cartridge 50 from housing 30. The locking mechanism 35 cooperates with corresponding structure located on the test cartridge 50. An opening or window 31 in the housing 30 allows a portion of the test cartridge 50 to be viewed, including, of course, the test and control regions of the membrane test strips 51.

Referring still to FIGS. 1-5, each membrane test strip 51 generally indicates the presence or absence of at least one analyte. A single drug, or class of drugs, is indicated by each membrane test strip 51, including without limitation, for example, cocaine (COC), amphetamine (AMP), methamphetamine (mAMP), marijuana (THC), methadone (MTD), phencyclidine (PCP), morphine, barbiturates, benzodiazepines, or alcohol.

Referring still to FIGS. 1-5, immunoassay-based fingerprint acquisition pad 60 includes a compressible, porous reaction medium, having a control zone and a plurality of reaction zones, arranged on a porous support. The control zone includes a control reagent to identify the fluid sample donor, and each reaction zone includes a reaction reagent to determine the presence of a specific analyte in the fluid sample. The control reagent includes a member of a predetermined ligand/receptor binding pair. Similarly, each reaction reagent includes a member of a predetermined ligand/receptor binding pair. Various ligand/receptor binding pairs for use within the control and reaction zones are discussed within the '863 and '815 patents.

Referring still to FIGS. 1-5, immunoassay-based fingerprint acquisition pad 60 is fluidicly coupled to the collection chamber 40. A signal-producing agent, located on upper surface of the porous support or the lower surface of the reaction medium, mixes with the fluid sample provided to the immunoassay-based fingerprint acquisition pad 60. The production of an image or pattern which identifies the person providing the sample is accomplished by applying a fingertip to the upper surface of the reaction medium and compressing the reaction medium so that the fluid sample/signal-producing agent mixture permeates the reaction medium, and allowing the control zone ligand/receptor reaction to take place so that the members of this immunological pair bond with the signal-producing agent and produce the fingerprint image. Similarly, the presence or absence of a specific analyte in the fluid sample is indicated within each reaction zone by the reaction of each specific reaction reagent with the fluid sample/signal-producing agent mixture.

Referring still to FIGS. 1-5, a piping system fluidicly couples the collection chamber 40 to the membrane test strips 31 and the immunoassay-based fingerprint acquisition pad 60. Tube 43 fluidicly couples the lower portion 42 of the collection chamber 40 to adapter 44 and test cartridge fluid reservoir 45. Similarly, tube 46 fluidicly couples the lower portion 42 of collection chamber 40 to adapter 61, located just beneath immunoassay-based fingerprint acquisition pad 60. Although tubes 43 and 46 are shown to be individually connected to the lower portion 42 of collection chamber 40, other configurations are also possible. For example, tube 43 may be the only connection to the lower portion 42 of collection chamber 40. In this example, a "T" connection may be incorporated into tube 43 to fluidicly couple tube 46 to immunoassay-based fingerprint acquisition pad 60. Alternatively, the required fluid connections may be molded directly within the housing 30.

Figure 6:
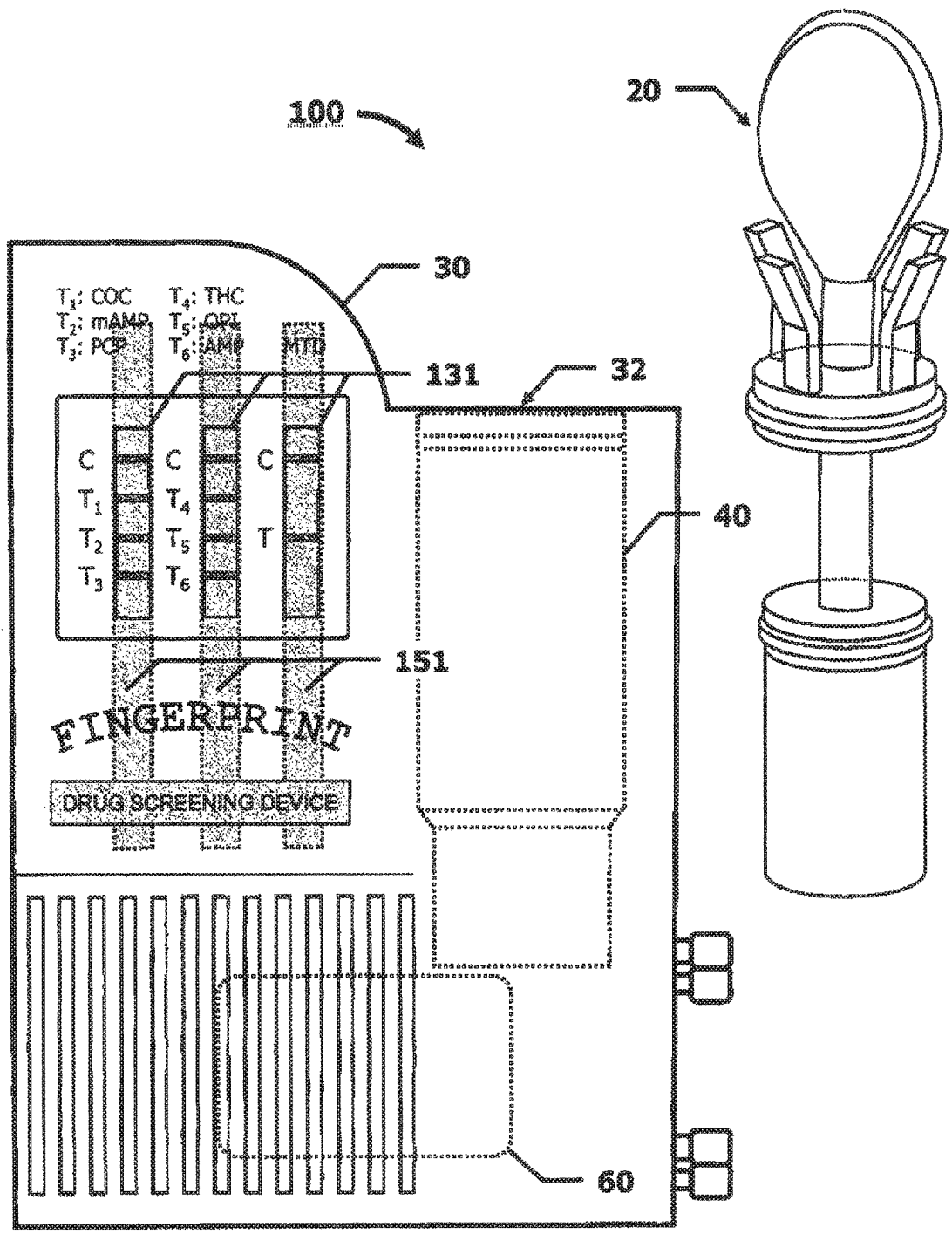
FIG. 6 depicts a front view of a fluid collection and analyte testing device in accordance with an embodiment of the present invention.
Figure 7:
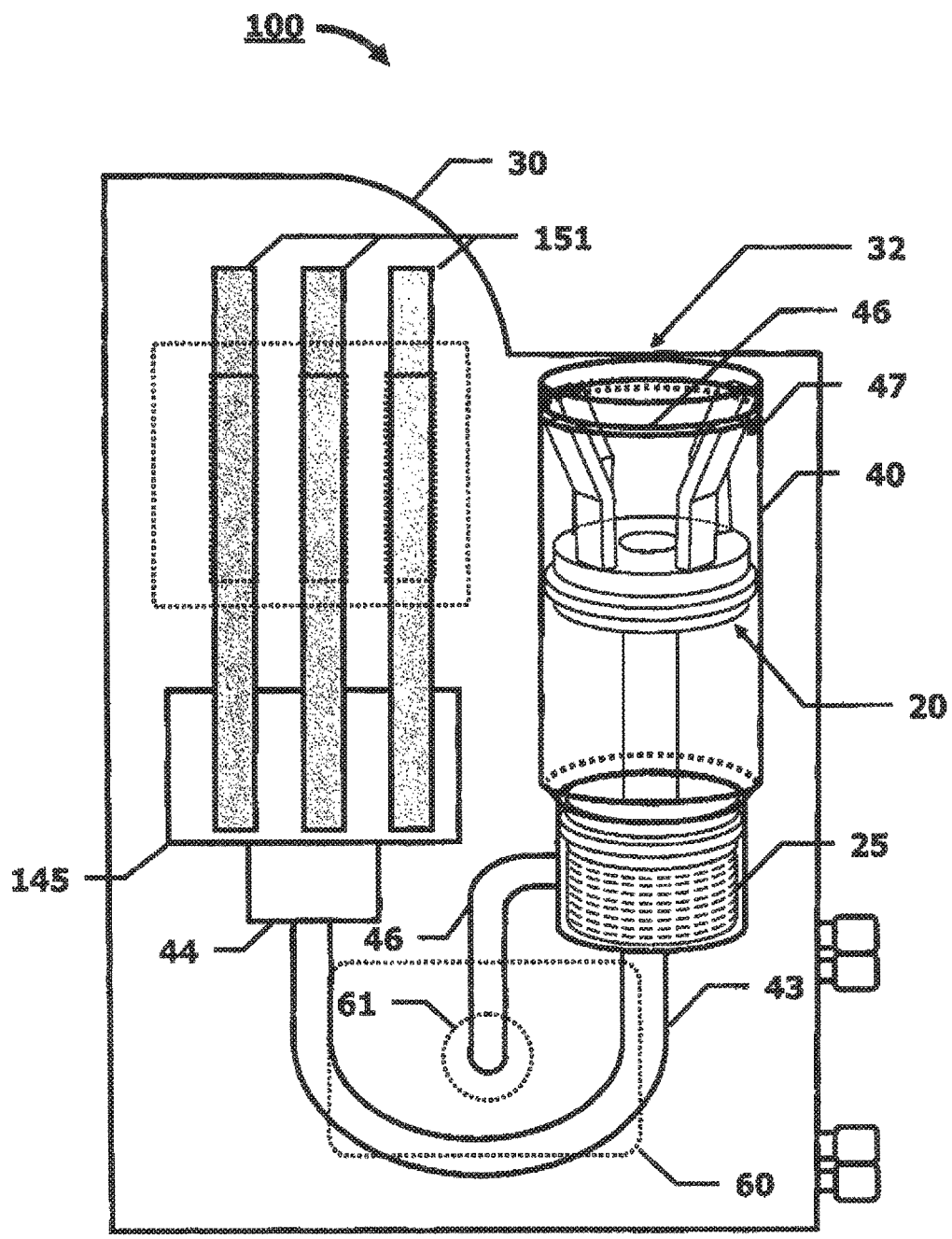
FIG. 7 depicts a front cutaway view of a fluid collection and analyte testing device in accordance with an embodiment of the present invention.
Figure 8:
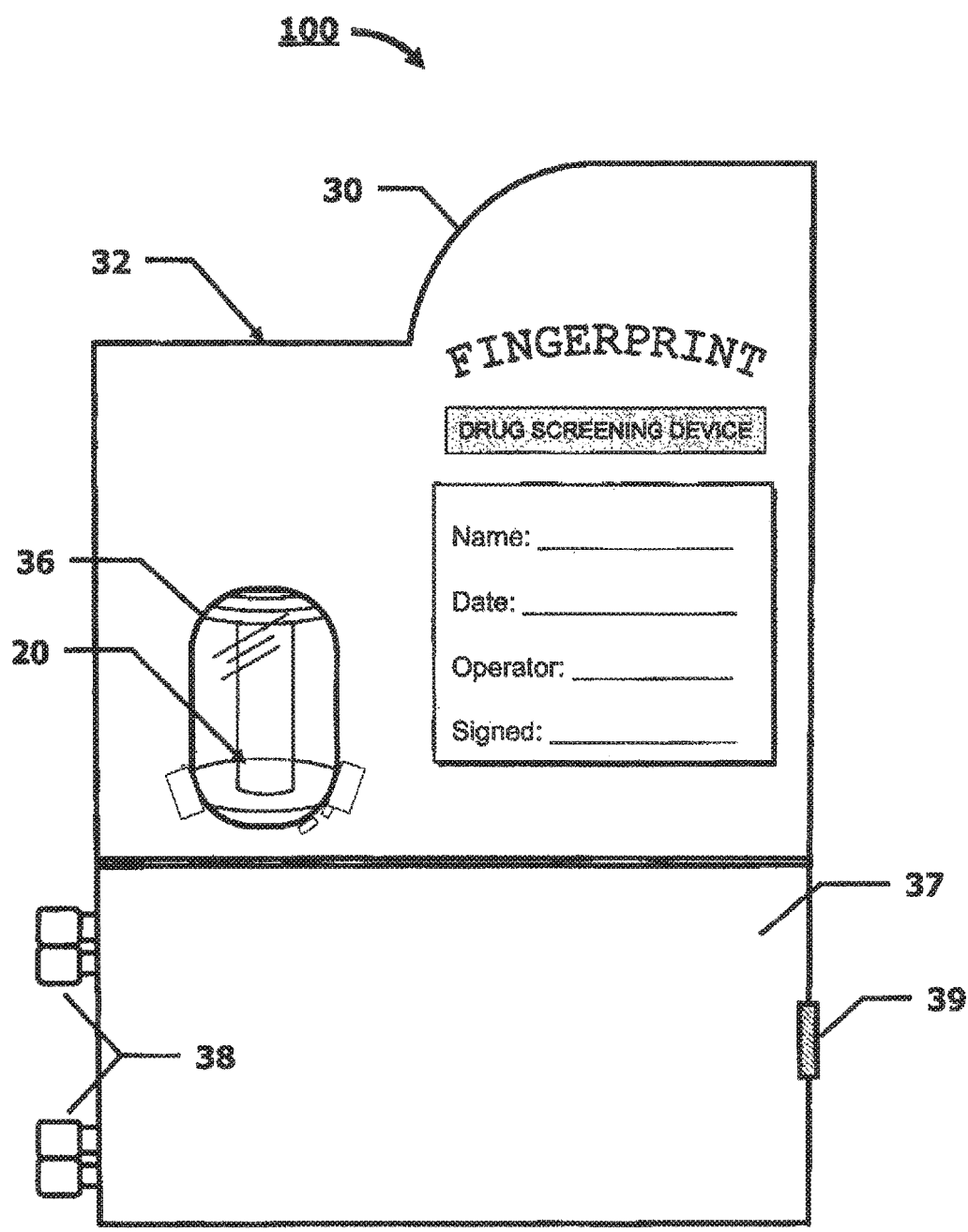
FIG. 8 depicts a back view of a fluid collection and analyte testing device in accordance with an embodiment of the present invention.

FIGS. 6-8 depict a fluid collection and analyte testing device in accordance with an embodiment of the present invention. Analyte screening device 100 includes membrane test strips 151 attached directly to housing 30. The membrane test strips are coupled to a fluid reservoir 145. Several analytes are indicated by each membrane test strip 151, including without limitation, for example, cocaine (COC), methamphetamine (mAMP) and phencyclidine (PCP) (leftmost strip), marijuana (THC), opiates and amphetamine (AMP) (middle strip) and methadone (MTD) (rightmost strip). In additional to recognized standards, minimum concentration levels at which a positive reaction is produced, that is, no visible line in the test region of the membrane test strip, may include, for example, amphetamine (50 ng/ml), methamphetamine (50 g/ml), a cocaine metabolite including benzoylecgonine and ecgonine methyl ester (20 ng/ml), an opiate including morphine, codeine and heroine (40 ng/ml), marijuana (THC COOH) (12 ng/mL) and phencyclidine (10 ng/ml). Several openings or windows 131 in the housing 30 allow the test and control regions of the membrane test strips 151 to be viewed.

Referring still to FIGS. 6-8, the fluid collector 20 receives a fluid sample from a test subject and temporarily stores the fluid sample until it is transferred to the housing 30. The fluid collector 20 is then inserted into the collection chamber 40 through the opening 32, and the fluid sample is extracted therefrom by compressing the sponge 25 against the bottom surface of the lower portion 42 of the collection chamber 40, thereby releasing the entrapped fluid into the tubes 43 and 46. Projections 26 extend from the upper surface of disk 21 and cooperate with an annular projection 53, located on the inner surface of the collection chamber 40, to secure the fluid collector 20 within the collection chamber 40.

Referring to FIGS. 7-8, after the fluid collector 20 is inserted a predetermined distance, the projections 26 engage the annular projection 53 to prevent the fluid collector 20 from being extracted from the collection chamber 40. Although four projections are depicted, at least two should be used to effectively secure the fluid collector 20 within the collection chamber 40. Alternatively, the annular projection 53 may cooperate with a projecting circumferential ring (not show), located above the sealing ring 28 of disk 21, to secure the fluid collector 20 within the collection chamber 40. As an additional measure of security, handle 23*a* may be detached from the fluid collector 20 along a line of weakness 27 after the fluid collector 20 has engaged the annular projection 53. If a twisting motion is desired to detach the handle 23 from the fluid collector 20, then one (or more) stop(s) 47 may be located just below the annular projection 53 to prevent the fluid collector 20 from rotating by engaging one (or more) of the projections 26.

Figure 9:
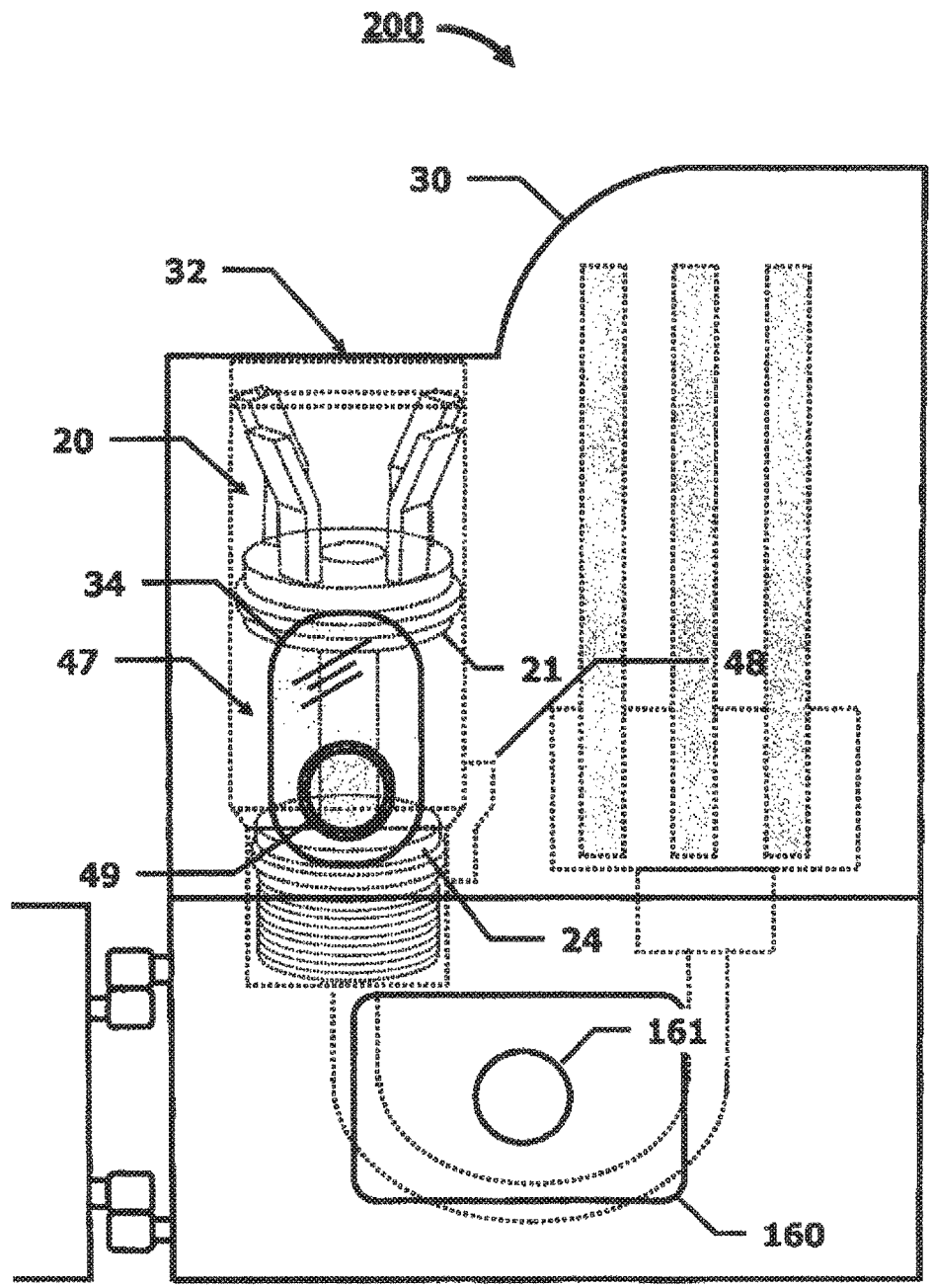
FIG. 9 depicts a back view of a fluid collection and analyte testing device in accordance with an embodiment of the present invention.

Referring to FIG. 9, analyte screening device 200 includes a window 37 incorporating a sealable opening 49 that allows access to the collection chamber 40. When the fluid collector 20 is secured within the collection chamber 40, sealable opening 49 allows access to a confirmation chamber 47 formed between the disks 21 and 24. A passage 48 fluidically couples the lower portion 42 of the collection chamber 40 to the confirmation chamber 47 to allow a portion of the fluid sample to flow into the confirmation chamber 47 as the fluid collector 20 is inserted into the collection chamber 40. Once the fluid collector 20 is secured with the collection chamber 40, a portion of the fluid sample is available for confirmation sampling through the sealable opening 49.

Referring still to FIG. 9, immunoassay-based fingerprint acquisition pad 60 is not fluidicly coupled to the collection chamber 40. Instead, a portion of the fluid sample is extracted through the sealable opening 49, using, for example, a pipette, and applied to the upper surface of immunoassay-based fingerprint acquisition pad 60. A signal-producing agent is applied to the person's fingertip, or, alternatively, the signal-producing agent may be located on the upper surface of the porous support or the lower surface of the reaction medium. The signal-producing agent then mixes with the fluid sample provided to the immunoassay-based fingerprint acquisition pad 60. The production of an image or pattern which identifies the person providing the sample is accomplished by applying a fingertip to the upper surface of the reaction medium and compressing the reaction medium so that the fluid sample permeates the reaction medium, and allowing the predetermined ligand/receptor reaction to take place so that the members of the immunological pair bond with the signal-producing agent and produce the fingerprint image. Similarly, the presence or absence of a specific analyte in the fluid sample is indicated within each reaction zone by the reaction of each specific reaction reagent with the fluid sample/signal-producing agent mixture.

Figure 10:
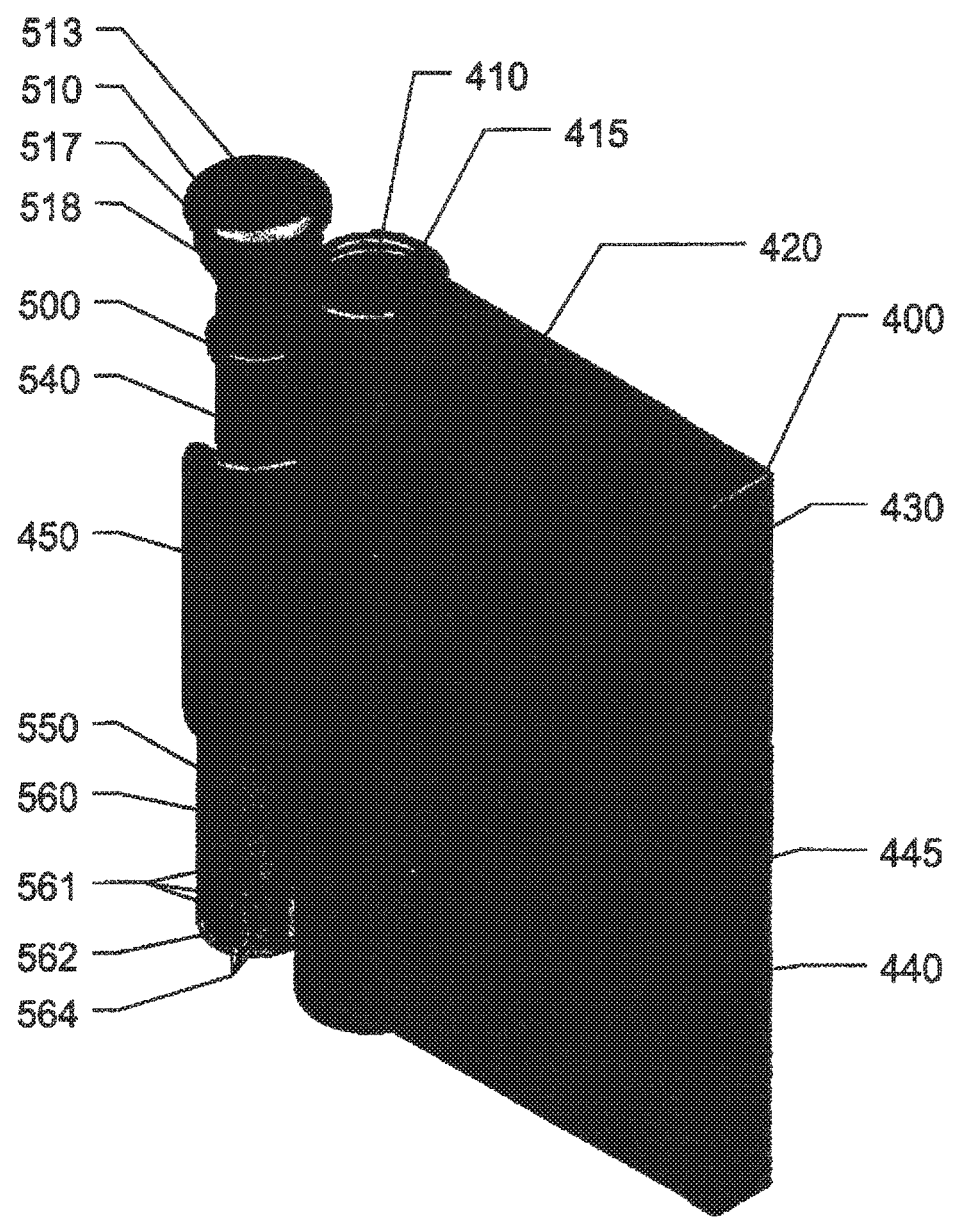
FIG. 10 depicts an isometric view of a fluid collection and analyte testing device in accordance with an embodiment of the present invention, in which a fluid collector rests in its holder in an analyte testing device.

Referring to FIG. 10, a fluid collector 500 rests in a fluid collector holder 450 attached to analyte testing device 400. The fluid collector 500 includes an upper segment 510 having an upper surface 513, a closure member 517, and a sealing member 518; a shaft 540; a housing 560 having several lateral openings 561, lower openings 564, and lower surface 562 and containing absorbent material 550. The analyte testing device 400 includes a receiving member 410 having an open end 415; a membrane test strip 420; a window 430 for viewing of the membrane test strip; a lower fluid channel 440; and an upper fluid channel 445.

Figure 11:
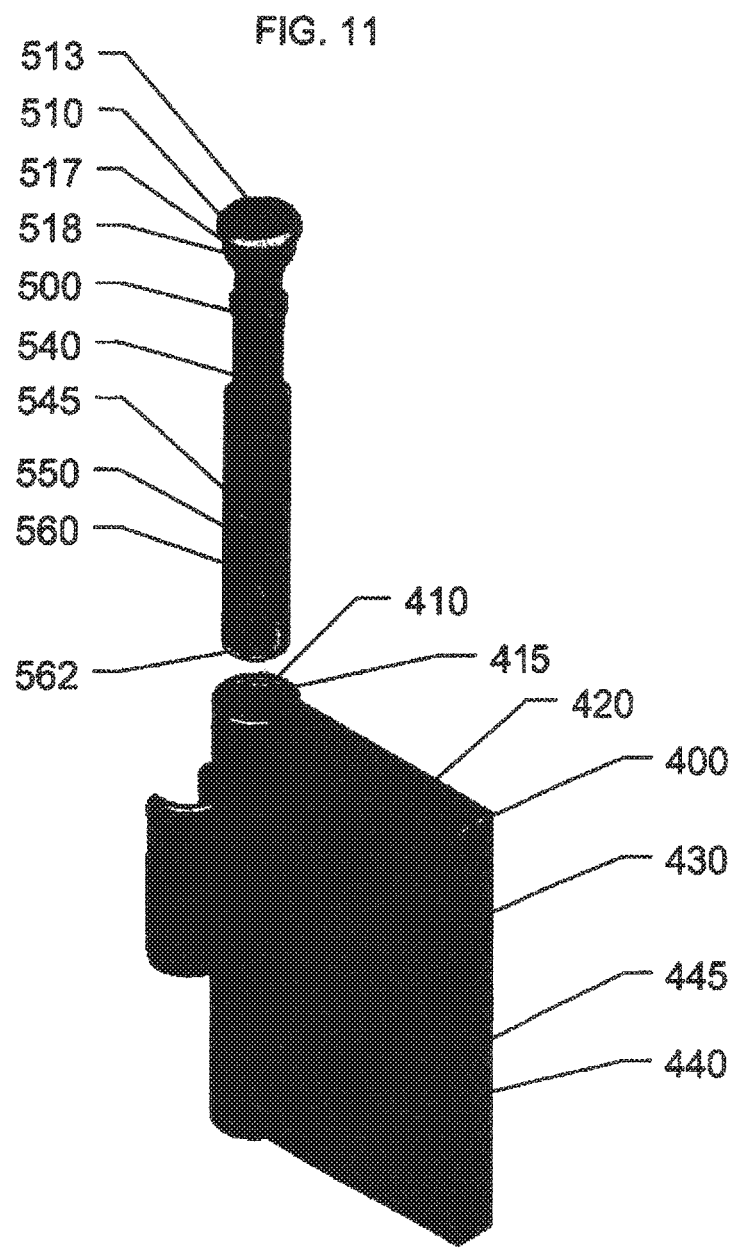
FIG. 11 depicts an isometric view of a fluid collection and analyte testing device in accordance with an embodiment of the present invention, in which a fluid collector is being inserted into an analyte testing device.

Referring to FIG. 11, after a fluid sample has been absorbed by absorbent material 550 the fluid collector 500 is inserted into the open and 415 of the receiving member 410.

Figure 12:
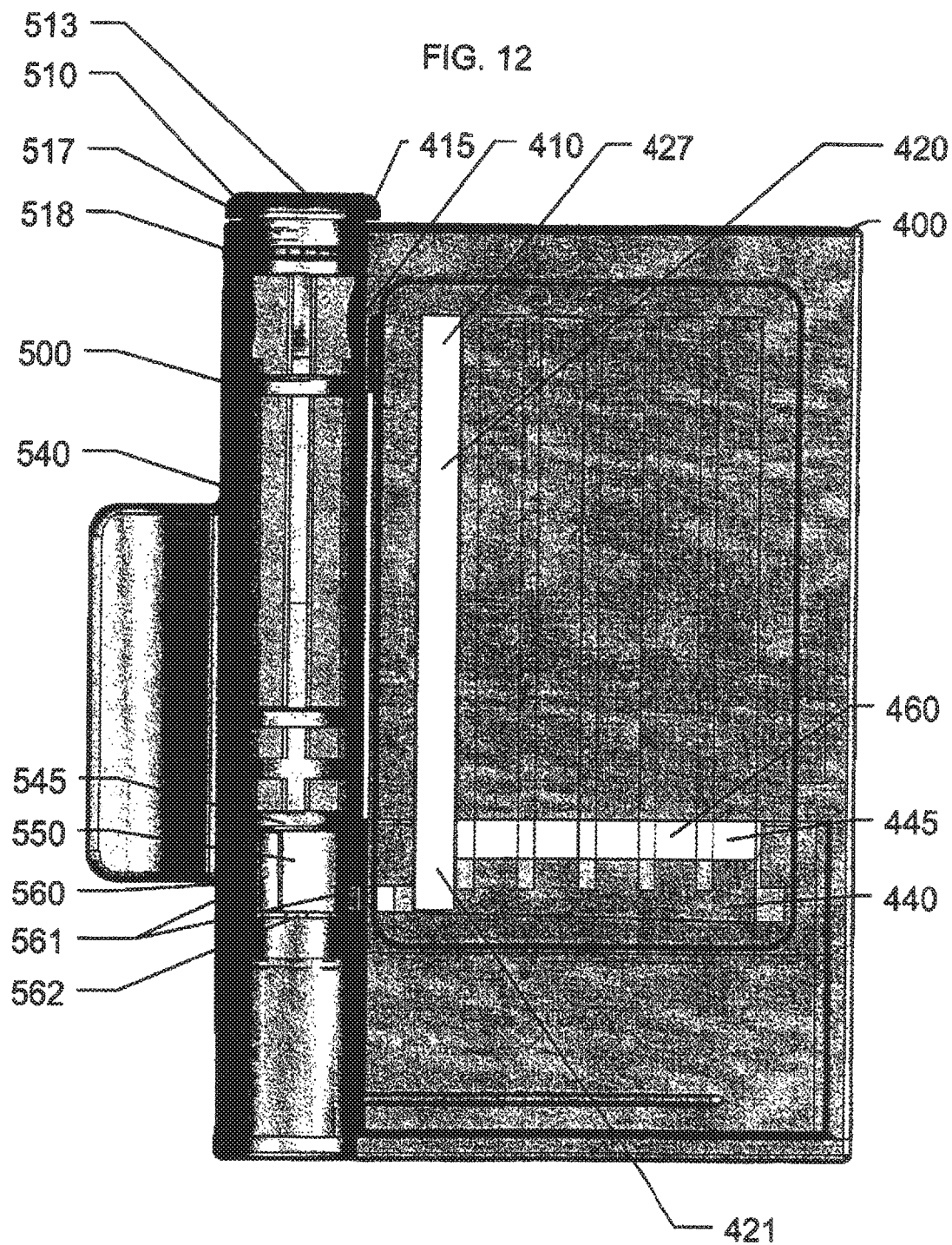
FIG. 12 depicts a front cross-sectional view of a fluid collection and analyte testing device in accordance with an embodiment of the present invention.

Referring to FIG. 12, compression of the upper surface 513 of the fluid collector 500 has caused closure element 517 to seat in the open end 415 of the receiving member 410, where sealing member 518 forms a seal. The fluid collector 500 has been fully inserted into the testing device 400, and the absorbent material 550 has been compressed between the compression element 545 and the lower surface 562 of the housing 560, causing the fluid sample to be expelled through openings 561. The fluid sample flows through lower channel 440 and encounters the proximal end 421 of the membrane test strip 420 and begins to upward towards the upper end 427 of the membrane test strip 420 by capillary action. Once a sufficient volume of the fluid sample has entered the lower channel 440, the fluid level rises until excess fluid flows through upper channel 445 and enters an absorbent pad, sample retention member 460.

Figure 13:
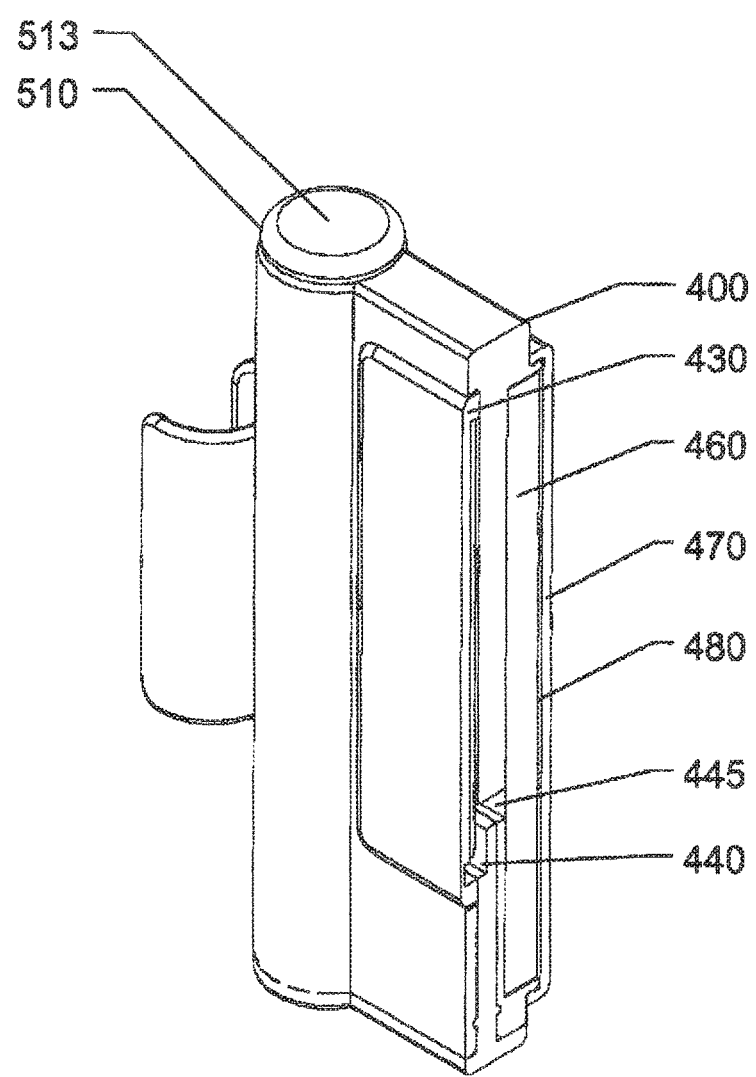
FIG. 13 depicts an isometric cross-sectional view of a fluid collection and analyte testing device in accordance with an embodiment of the present invention.

Referring to FIG. 13, the fluid sample fills the lower channel 440 before flowing into the upper channel 445 to enter the sample retention member 450. The sample retention member 460 is bonded to fingerprint acquisition pad 480, which is covered by the rear door 470.

Figure 14:
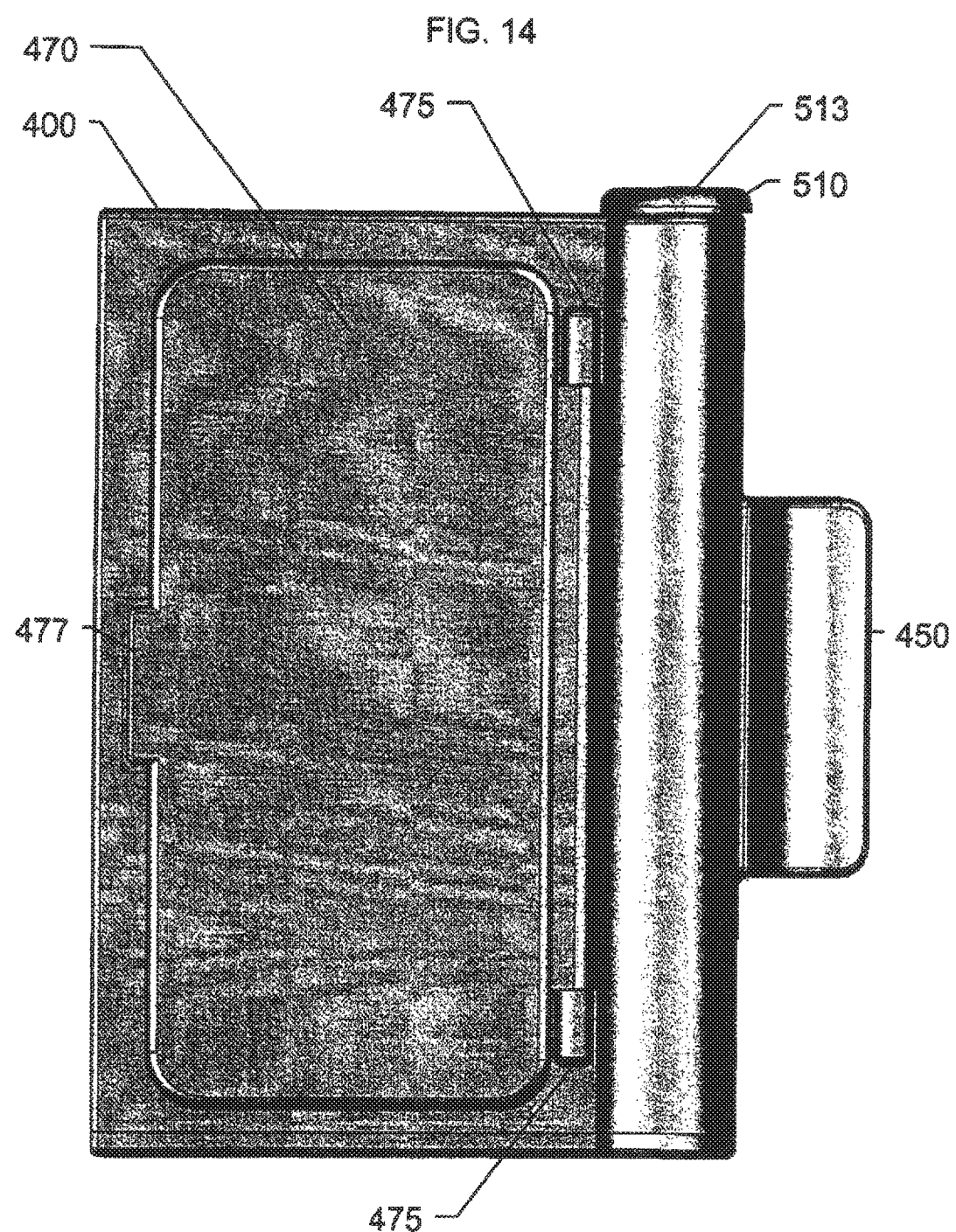
FIG. 14 depicts a rear view of a fluid collection and analyte testing device in accordance with an embodiment of the present invention.

Referring to FIG. 14, the fingerprint acquisition pad is covered by the rear door 470, which is held closed by closure member 477 and pivots into the opened position on the axis defined by the hinges 475.

Figure 15:
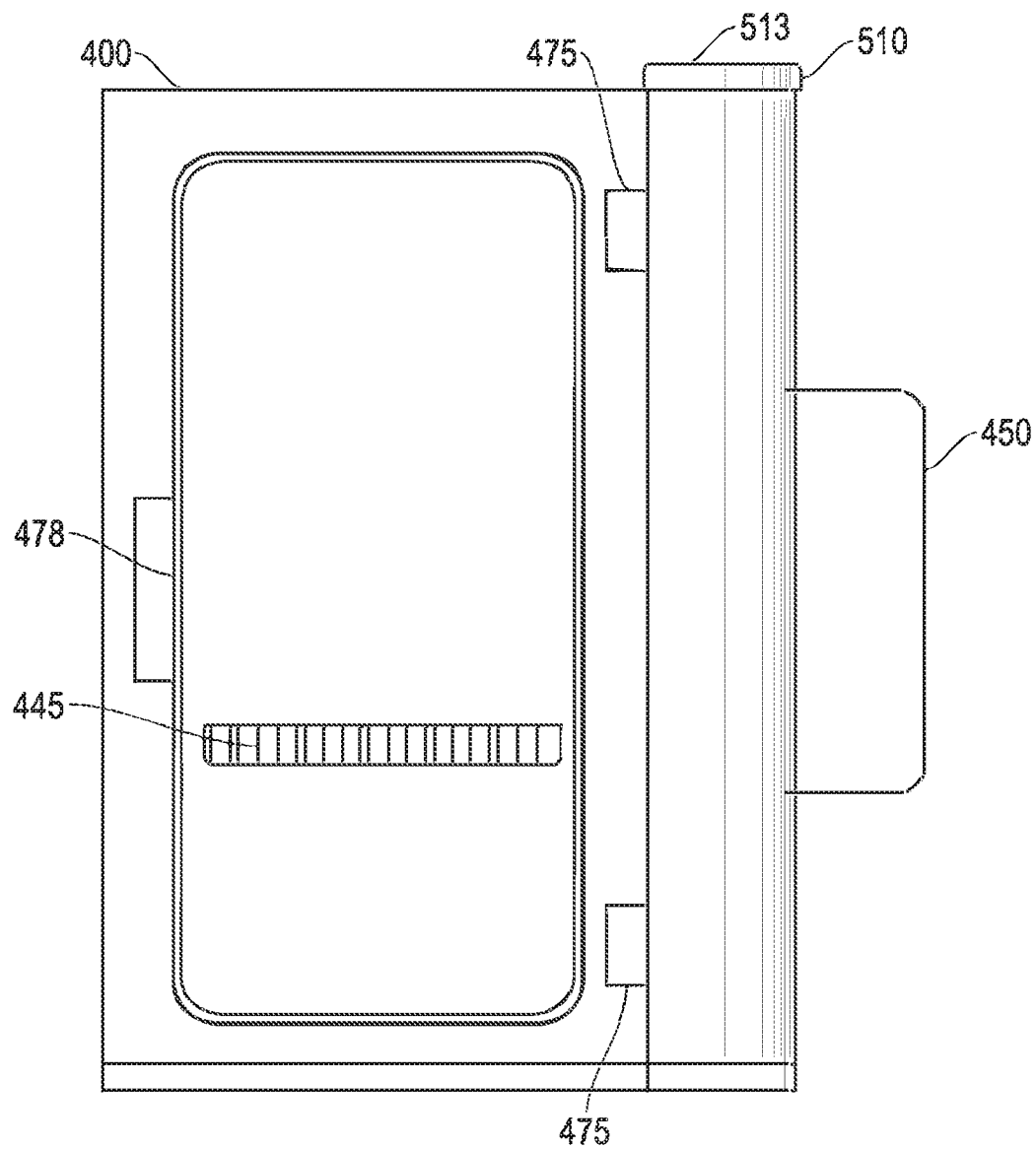
FIG. 15 depicts a rear view of a fluid collection and analyte testing device in accordance with an embodiment of the present invention having the rear door and fingerprint removed to show a fluid channel beneath.

Referring to FIG. 15, the rear door, fingerprint acquisition pad, and sample retention member are hidden to show a rear view of the upper channel 445 through which the fluid sample flows to enter the sample retention member. The closure member of the rear door cooperates with latch member 478 to secure the door in the closed position.

Figure 16A:
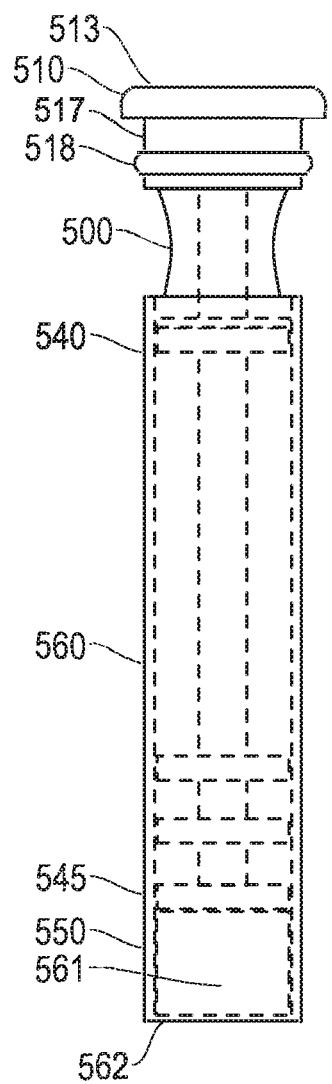
FIG. 16A depicts a side view of a fluid collection device in accordance with an embodiment of the present invention.
Figure 16B:
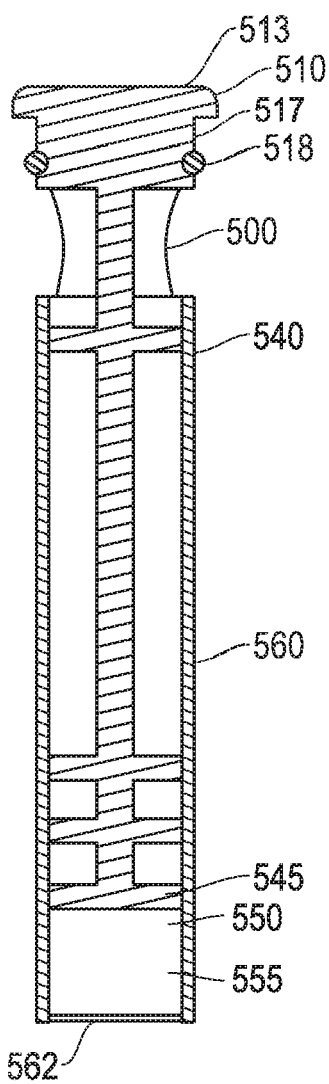
FIG. 16B depicts a cross-sectional front view of a fluid collection device in accordance with an embodiment of the present invention.
Figure 19:
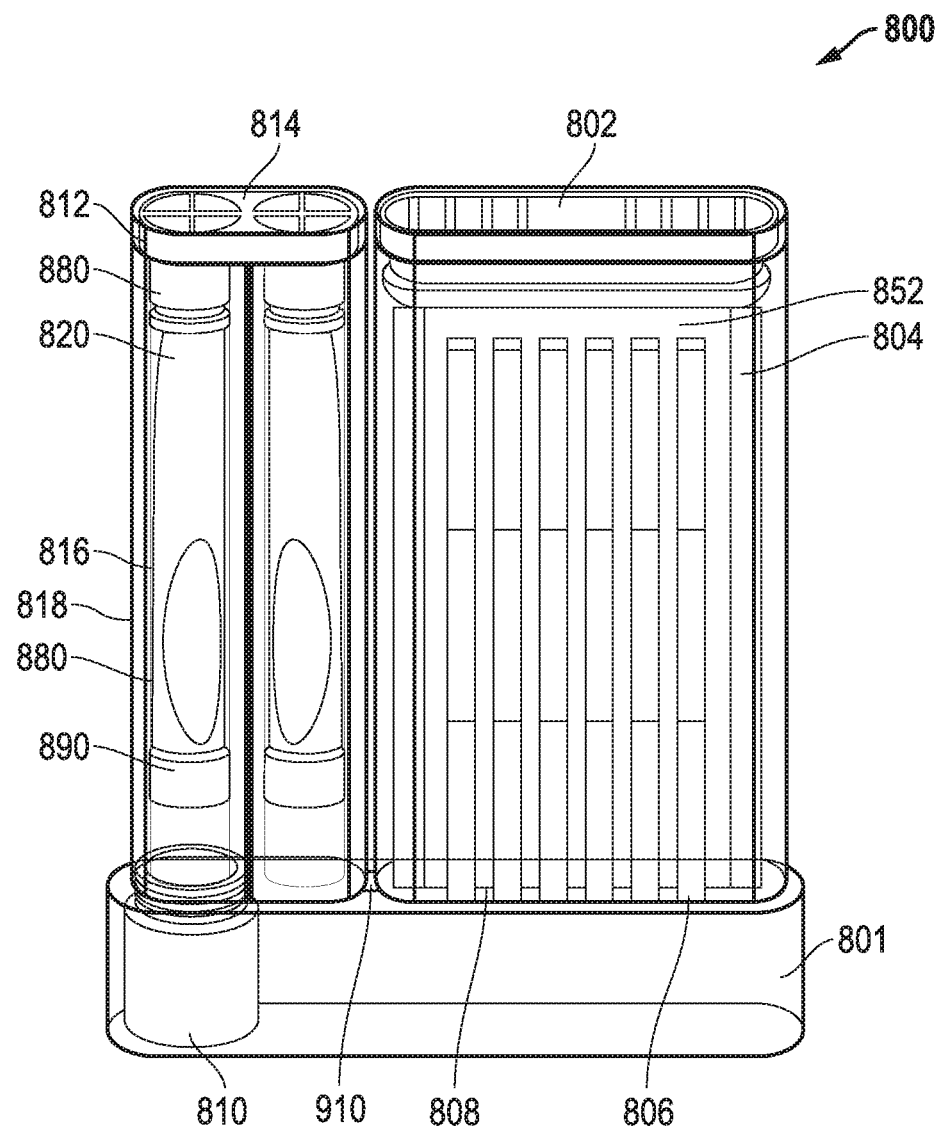
FIG. 19 depicts a perspective view of a fluid collection and analyte testing device in accordance with an embodiment of the present invention.
Figure 20:
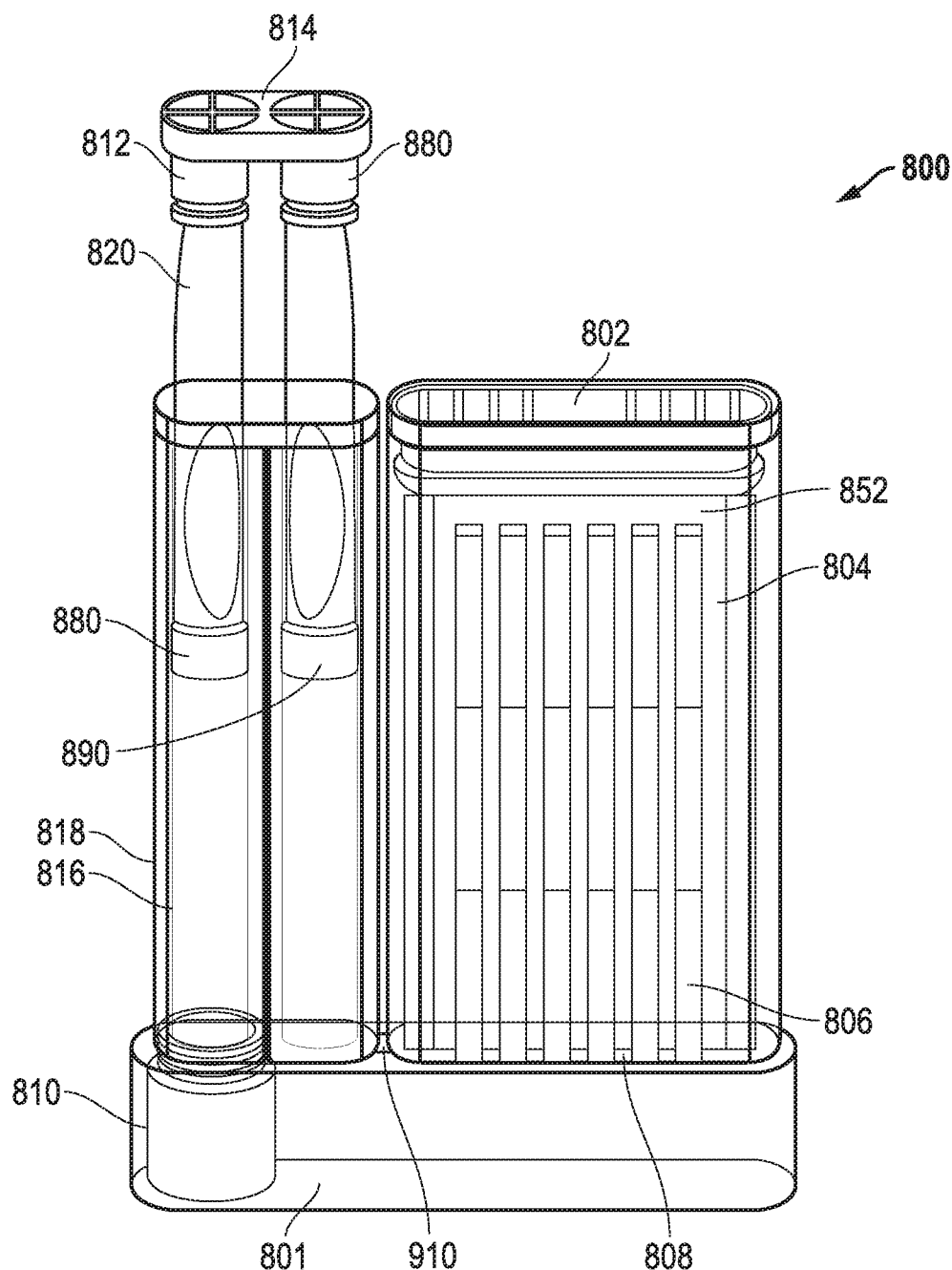
FIG. 20 depicts a perspective view of a fluid collection and analyte testing device in accordance with an embodiment of the present invention.
Figure 21:
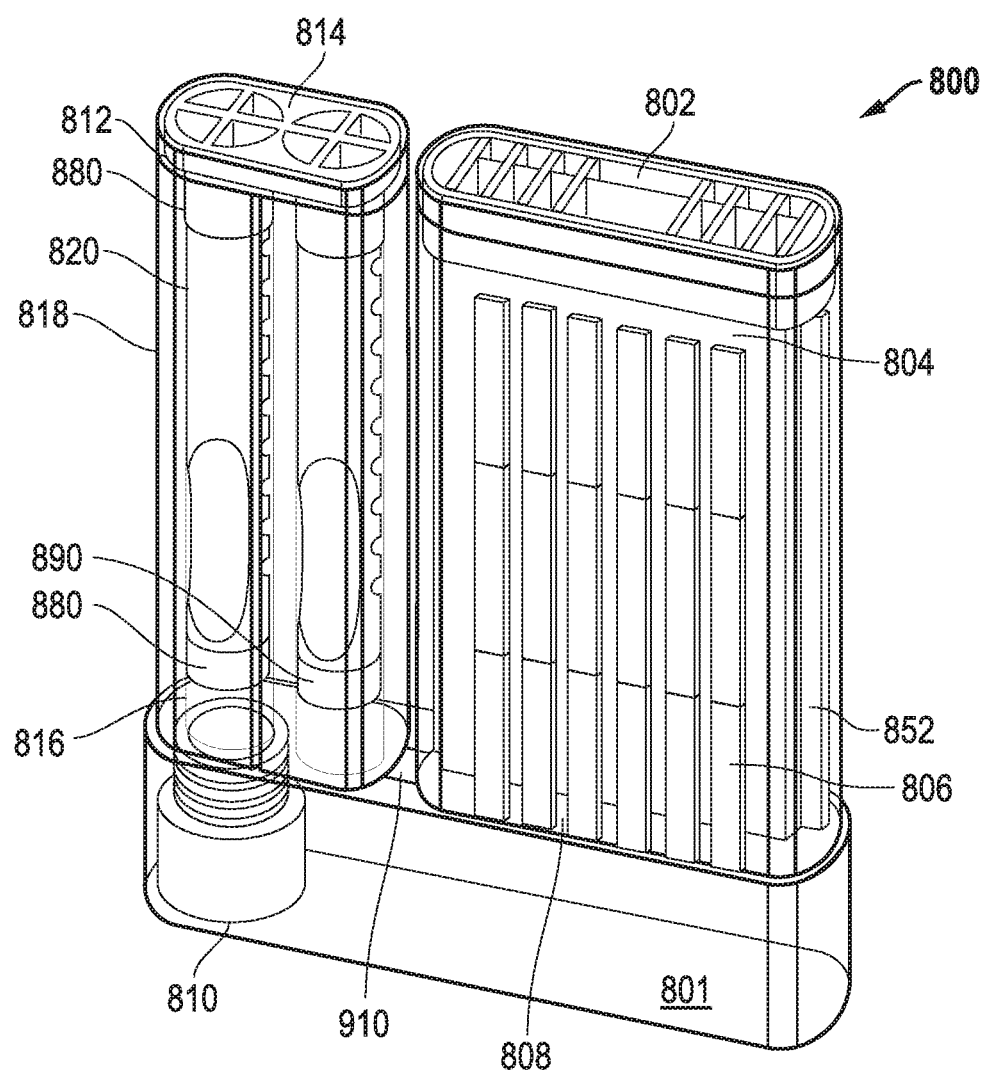
FIG. 21 depicts a perspective view of a fluid collection and analyte testing device in accordance with an embodiment of the present invention.
Figure 22:
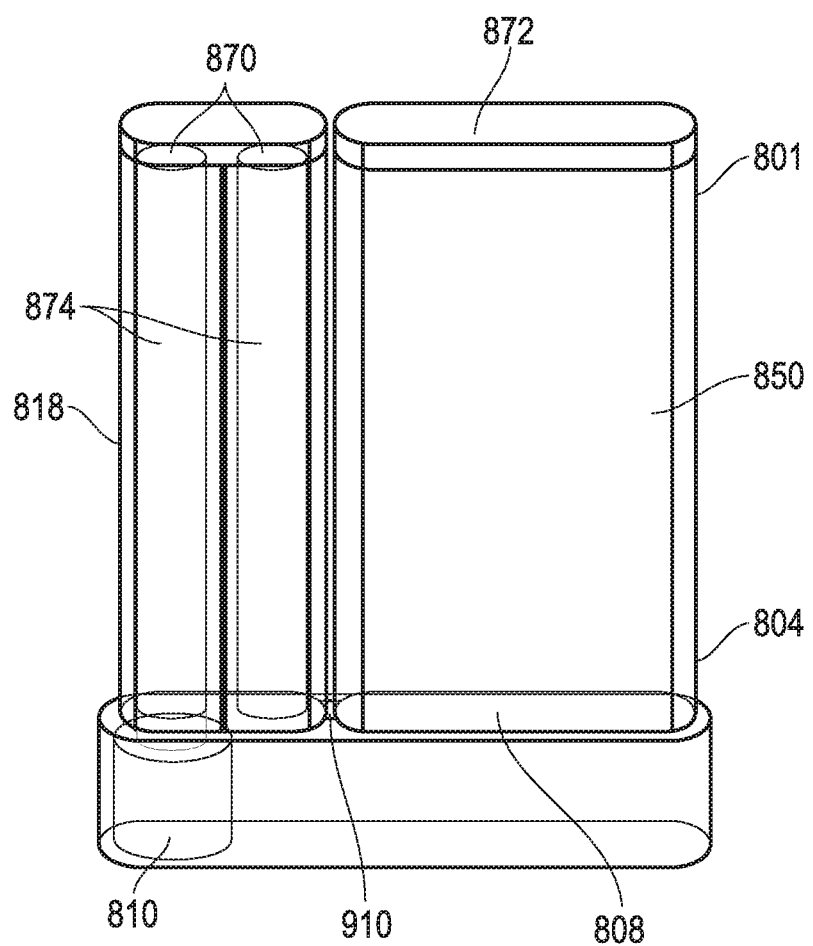
FIG. 22 depicts a perspective view of a housing of a fluid collection and analyte testing device in accordance with an embodiment of the present invention.
Figure 23:
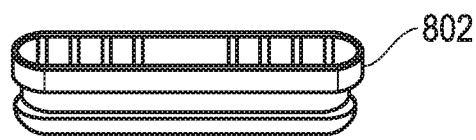
FIG. 23 depicts a perspective view of a test cartridge cap of a fluid collection and analyte testing device in accordance with an embodiment of the present invention.
Figure 24:
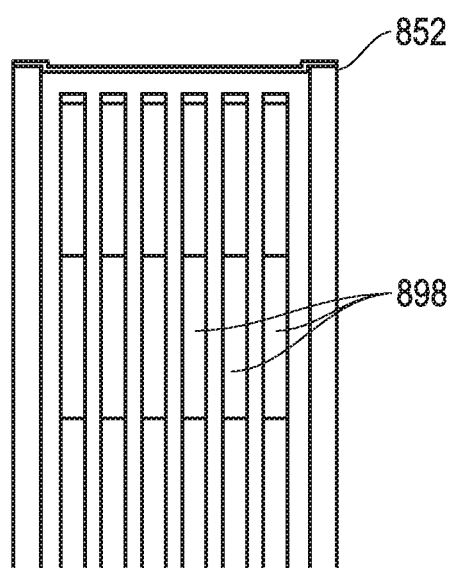
FIG. 24 depicts a front view of a dual surface test cartridge with test strip holders back-to-back of a fluid collection and analyte testing device in accordance with an embodiment of the present invention.
Figure 25:
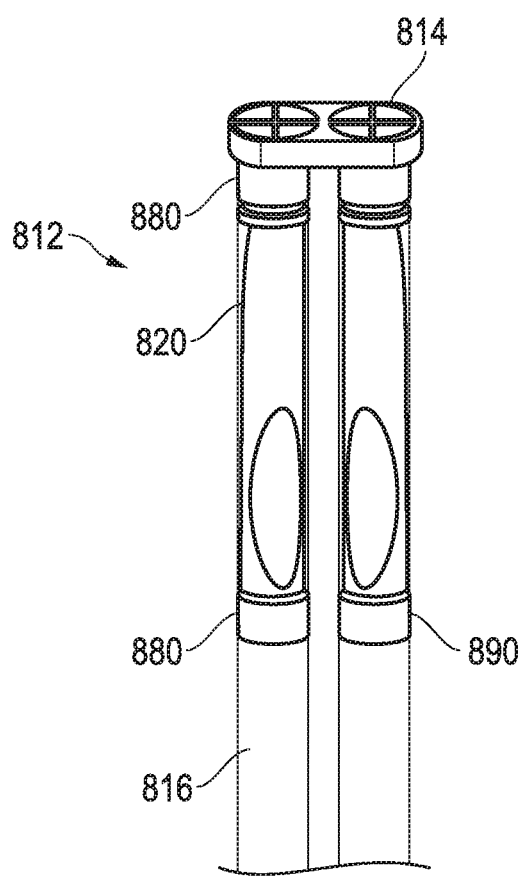
FIG. 25 depicts a perspective view of a split sample (dual sample) fluid collector of a fluid collection and analyte testing device in accordance with an embodiment of the present invention.
Figure 26:
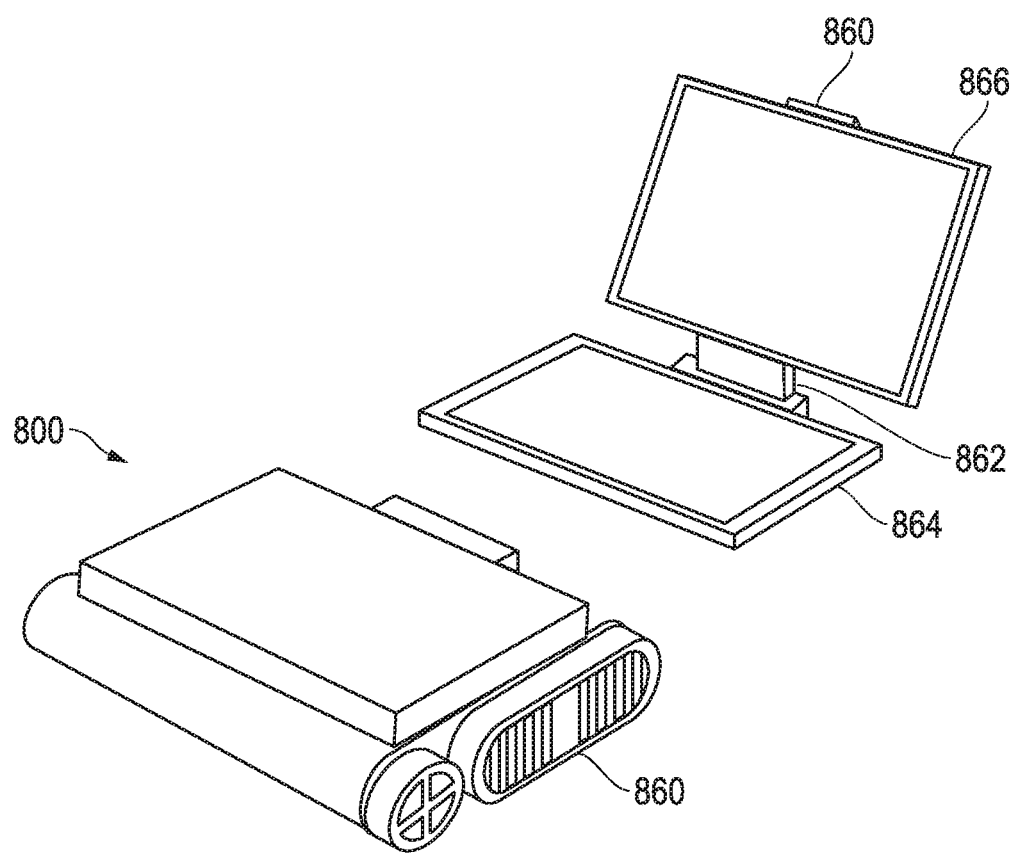
FIG. 26 depicts perspective view of a fingerprint assembly of a fluid collection and analyte testing device in accordance with an embodiment of the present invention.
Figure 27:
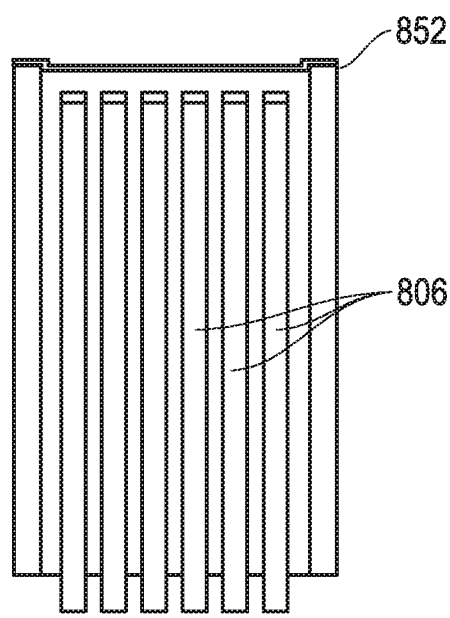
FIG. 27 depicts a front view of a dual surface test cartridge with test strips back-to-back of a fluid collection and analyte testing device in accordance with an embodiment of the present invention.
Figure 28:
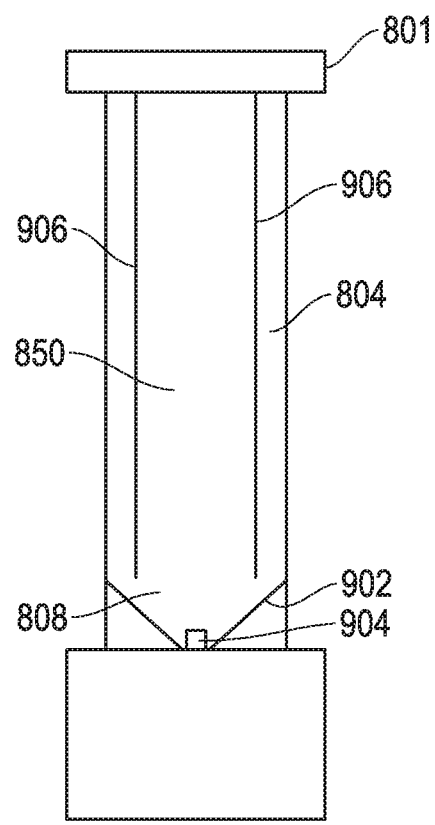
FIG. 28 depicts a cross-sectional end view of a housing of a fluid collection and analyte testing device in accordance with an embodiment of the present invention.
Figure 29:
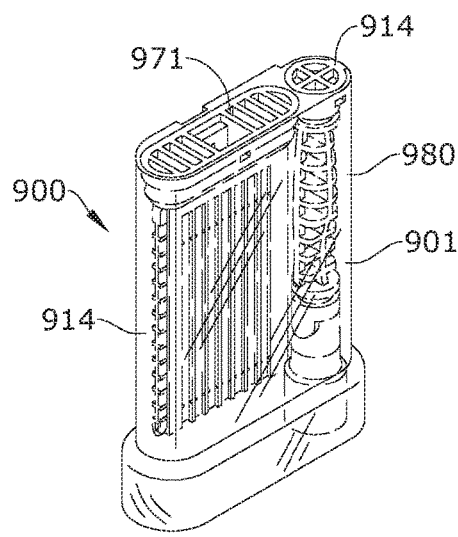
FIG. 29 depicts a front perspective view of a fluid collection and analyte testing device in accordance with an embodiment of the present invention.
Figure 30:
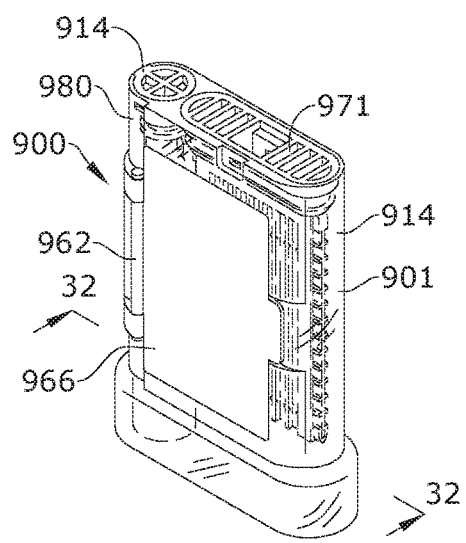
FIG. 30 depicts a rear perspective view of a fluid collection and analyte testing device in accordance with an embodiment of the present invention.
Figure 31:
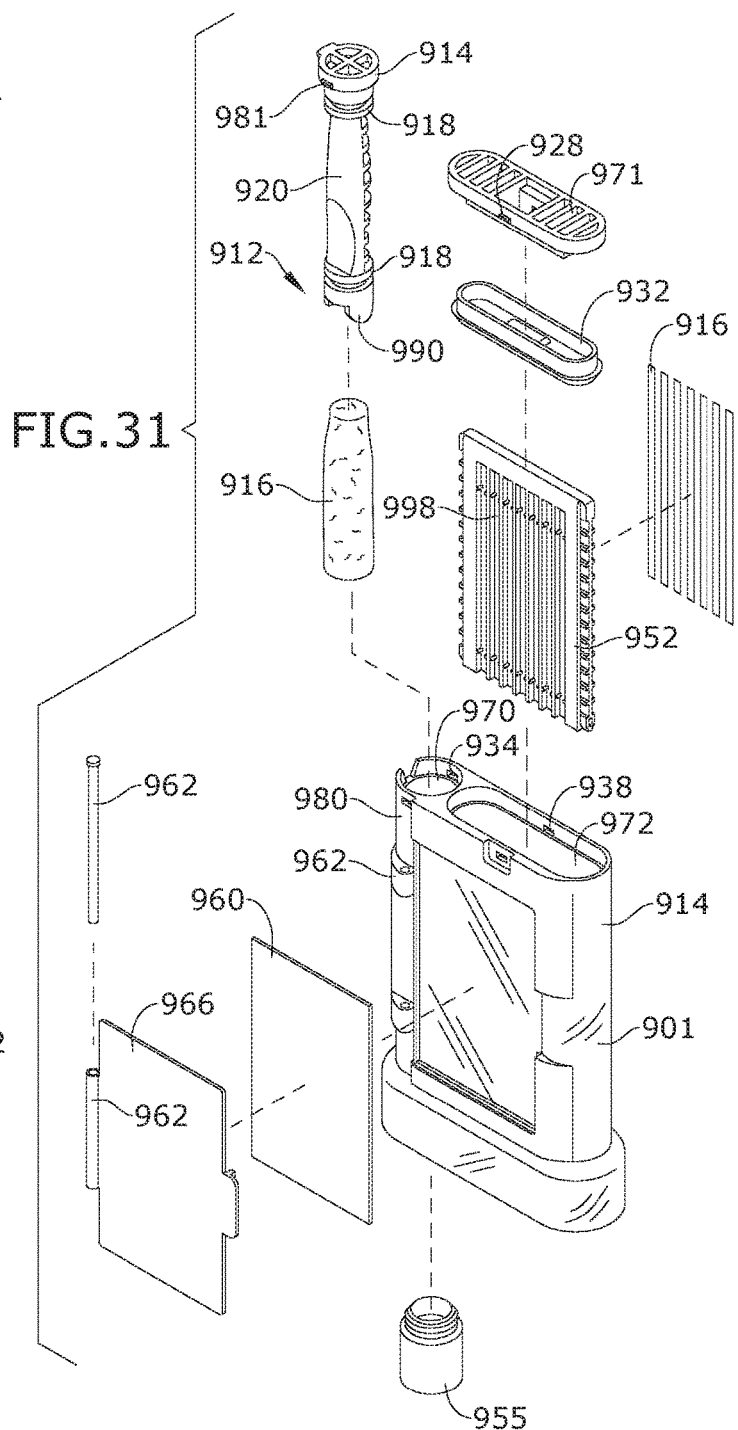
FIG. 31 depicts an exploded view of a fluid collection and analyte testing device in accordance with an embodiment of the present invention.
Figure 32:
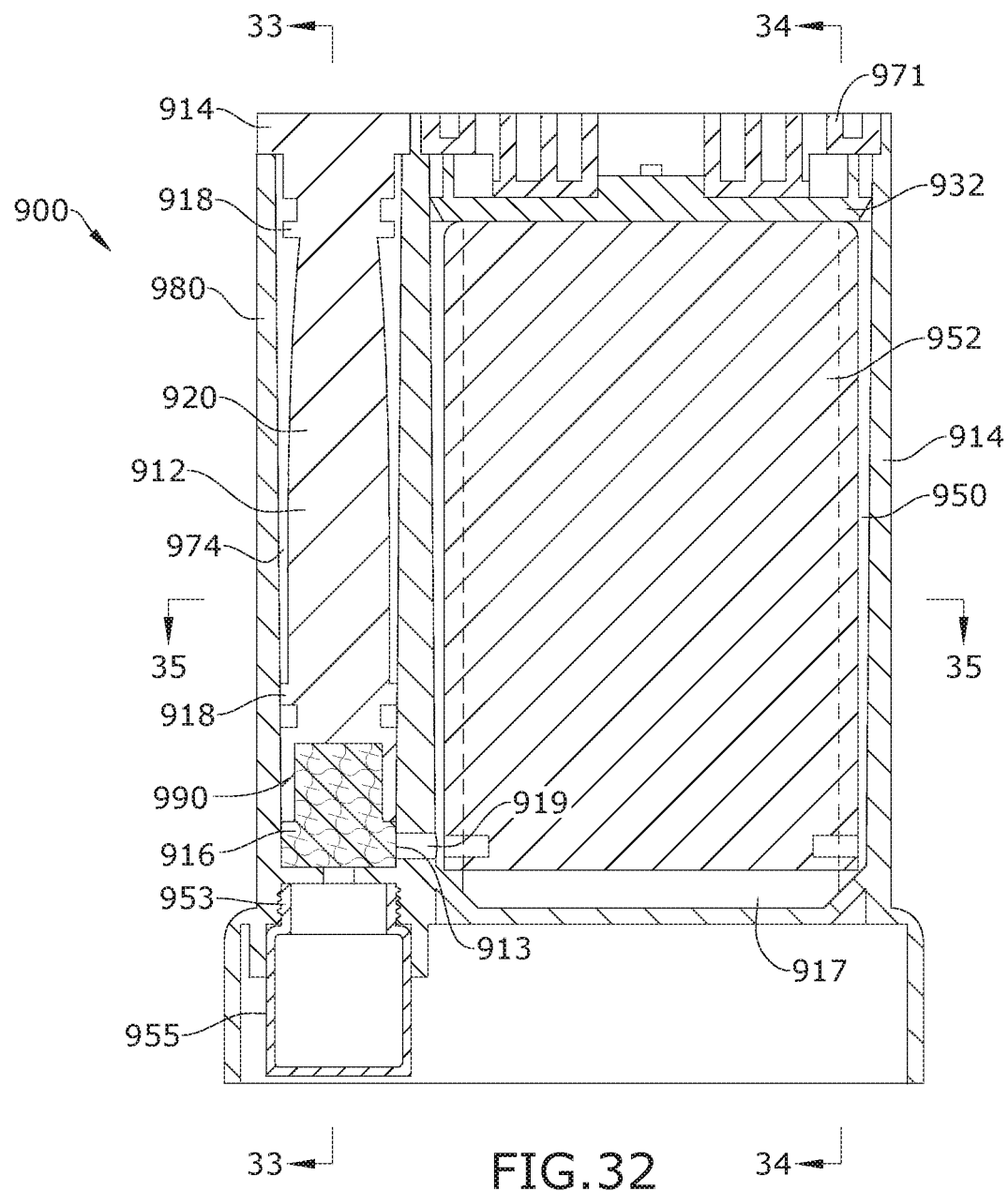
FIG. 32 depicts a cross-sectional view of the device taken along line 32-32 of FIG. 30.
Figure 36:
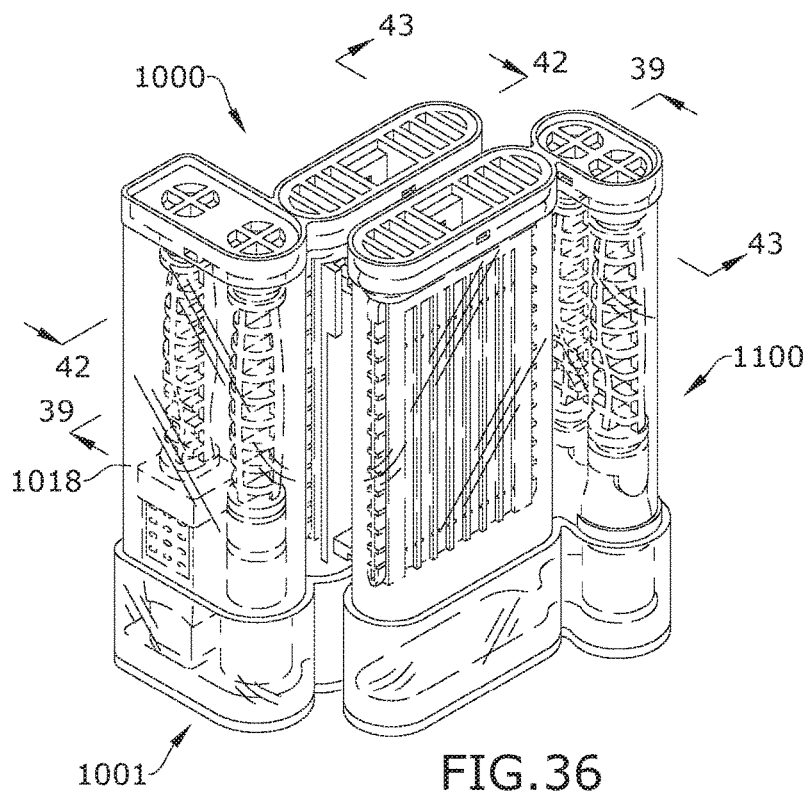
FIG. 36 depicts a perspective view of attached fluid collection and analyte testing devices in accordance with an embodiment of the present invention.
Figure 37:
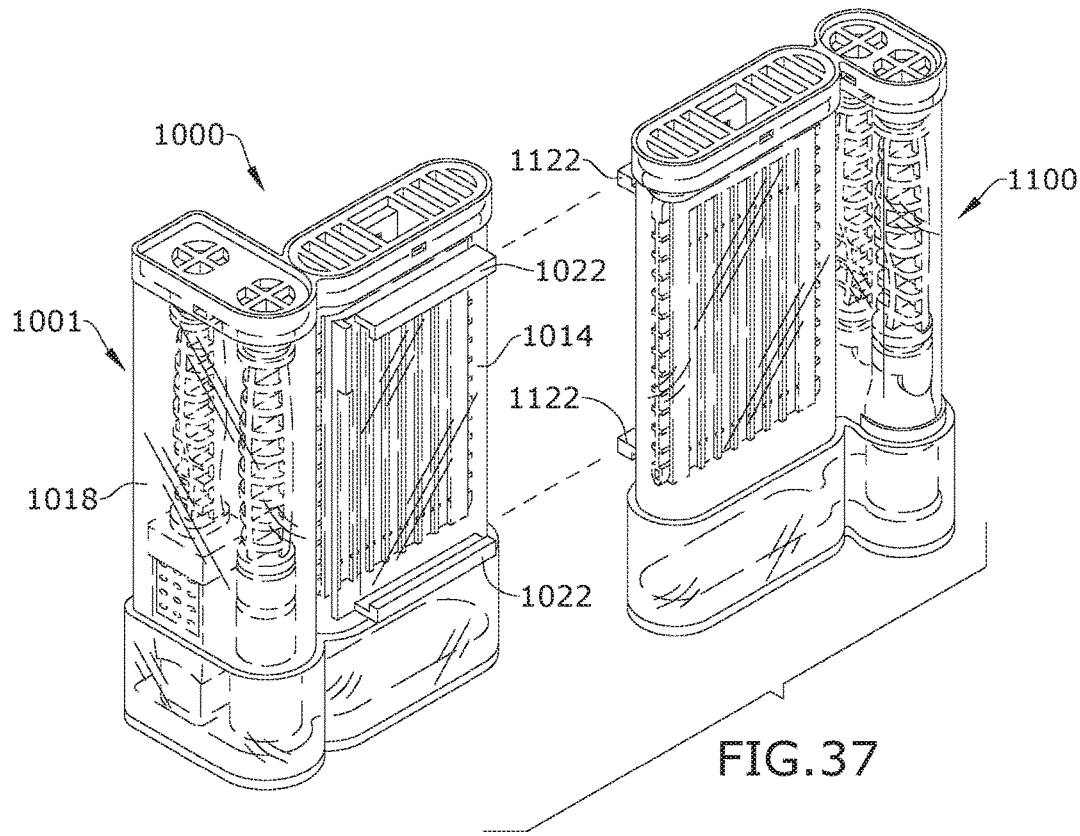
FIG. 37 depicts a perspective view of detached fluid collection and analyte testing devices in accordance with an embodiment of the present invention.
Figure 38:
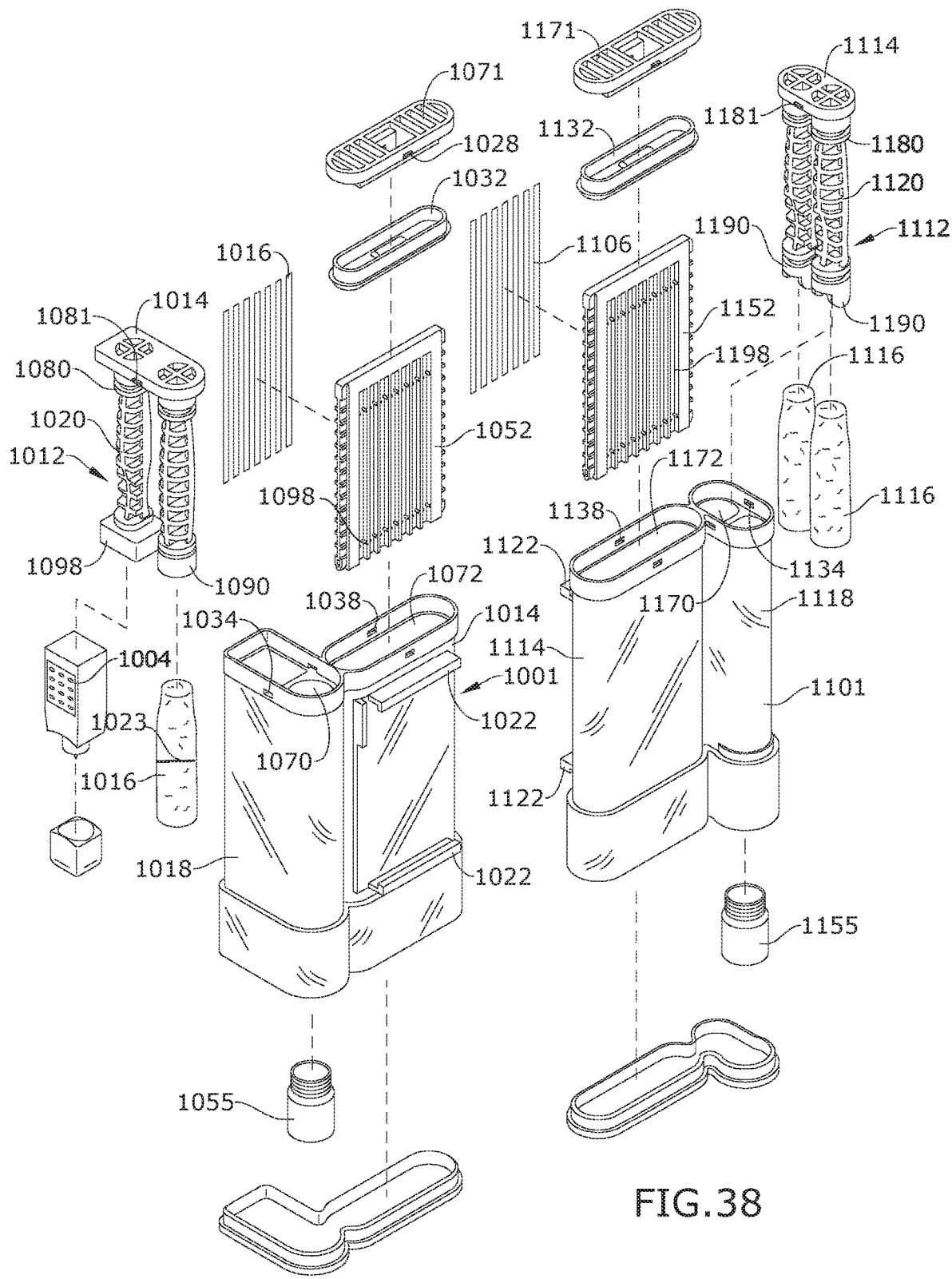
FIG. 38 depicts an exploded view of fluid collection and analyte testing devices in accordance with an embodiment of the present invention.
Figures 39, 40:
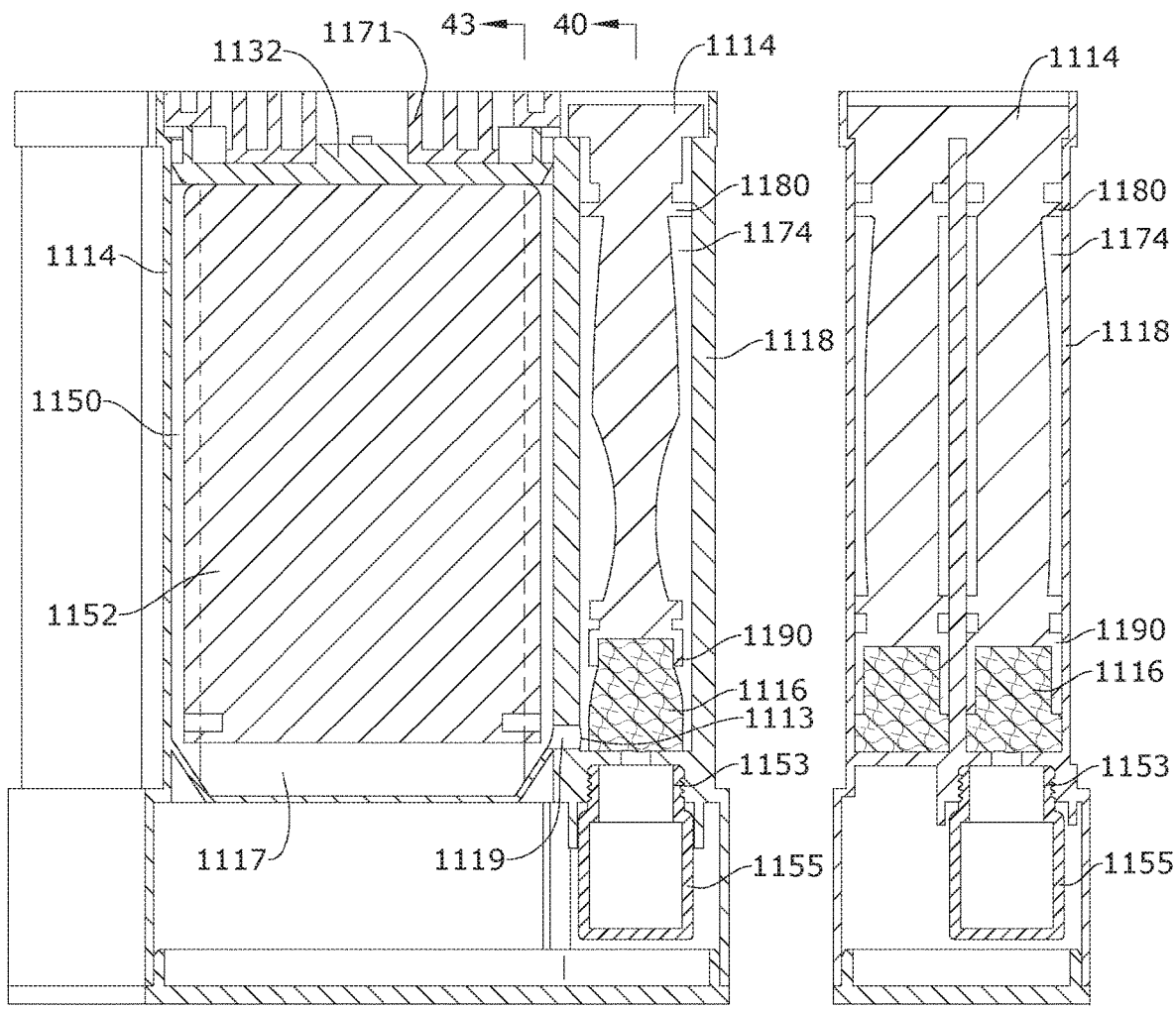
FIG. 39 depicts a cross-sectional view taken along line 39-39 of the device of FIG. 36.
FIG. 40 depicts a cross-sectional view of the device taken along line 40-40 of FIG. 39.
Figure 41:
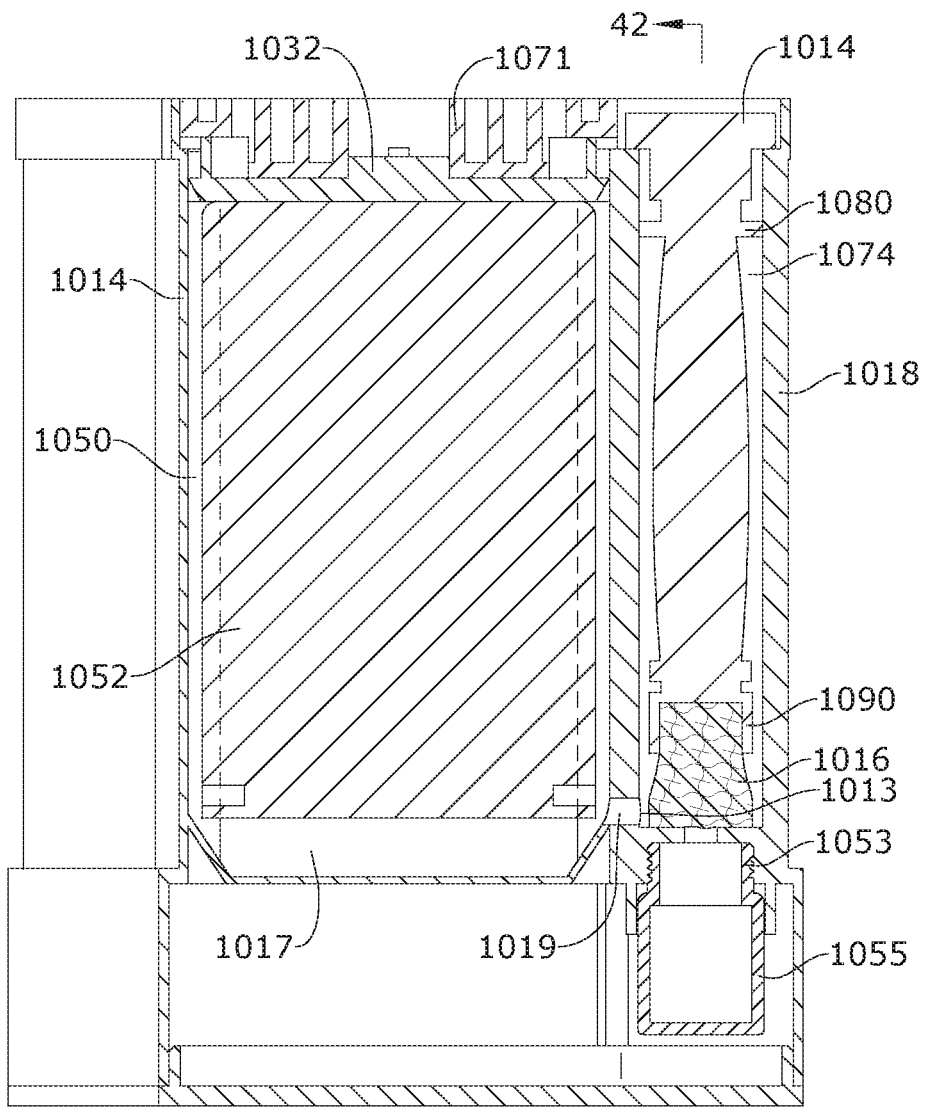
FIG. 41 depicts a cross-sectional view of the device taken along line 41-41 of FIG. 36.
Figure 44:
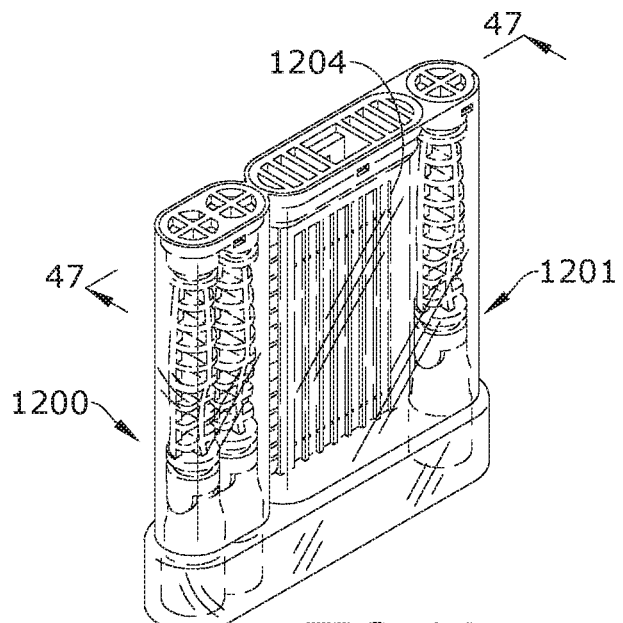
FIG. 44 depicts a front perspective view of a fluid collection and analyte testing device in accordance with an embodiment of the present invention.
Figure 45:
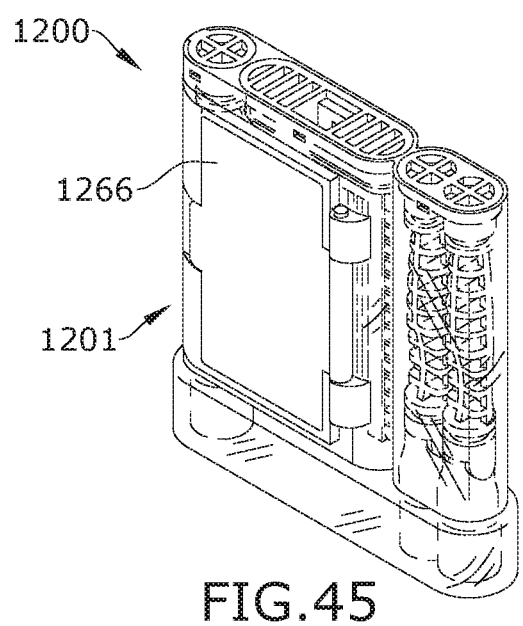
FIG. 45 depicts a rear perspective view of a fluid collection and analyte testing device in accordance with an embodiment of the present invention.
Figure 46:
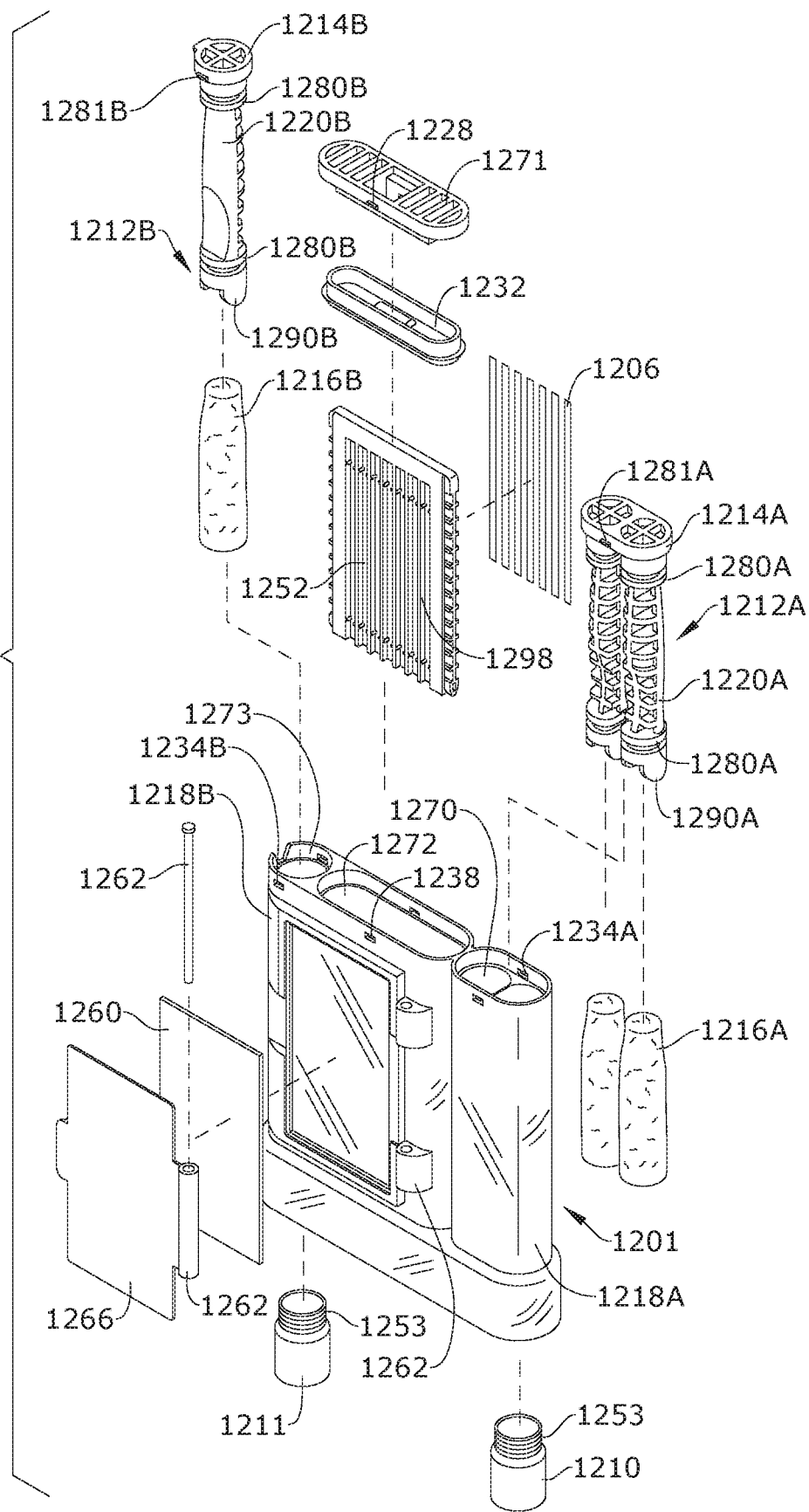
FIG. 46 depicts an exploded view of a fluid collection and analyte testing device in accordance with an embodiment of the present invention.
Figure 47:
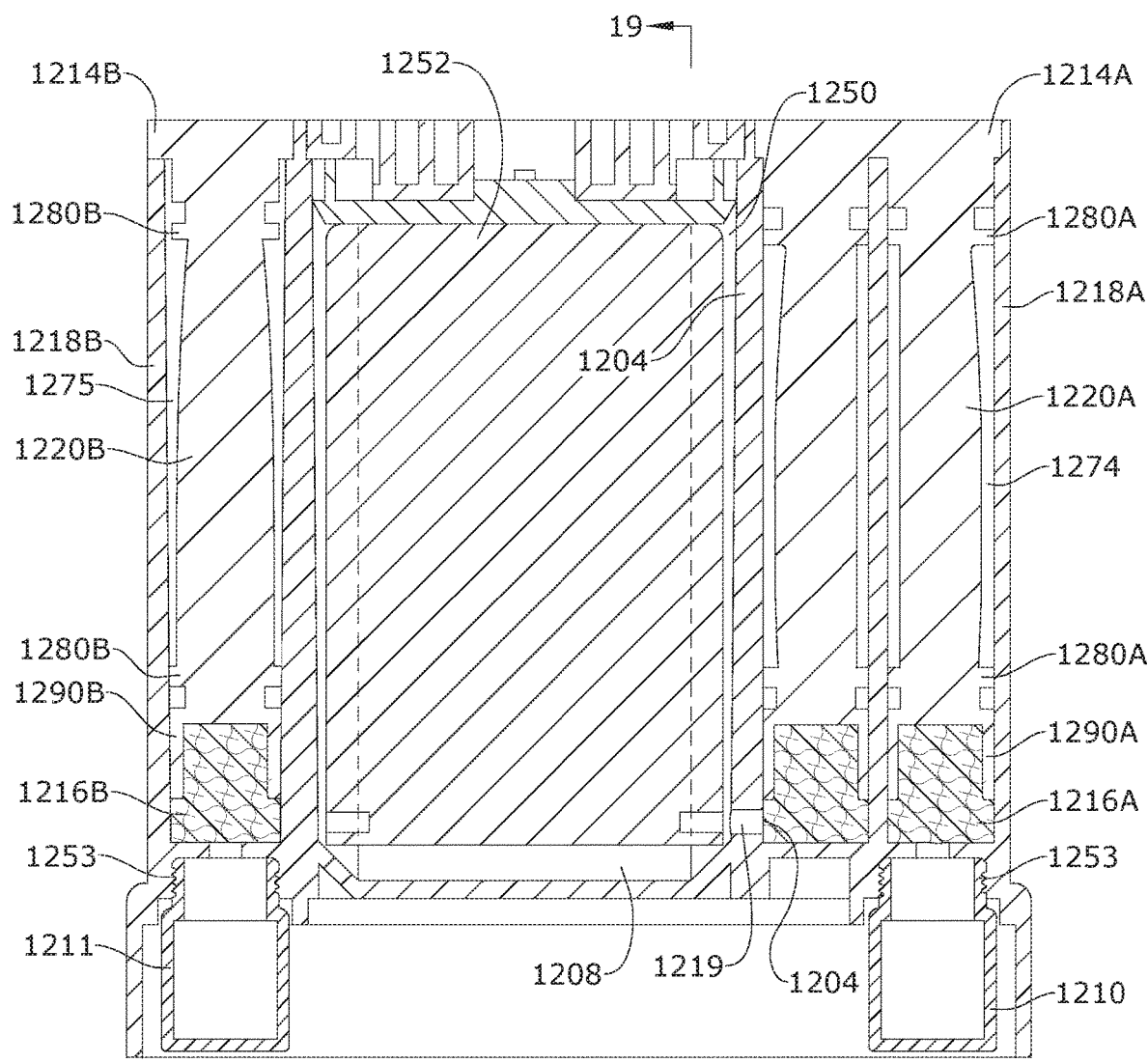
FIG. 47 depicts a cross-sectional view of the device taken along line 47-47 of FIG. 44.
Figure 48:
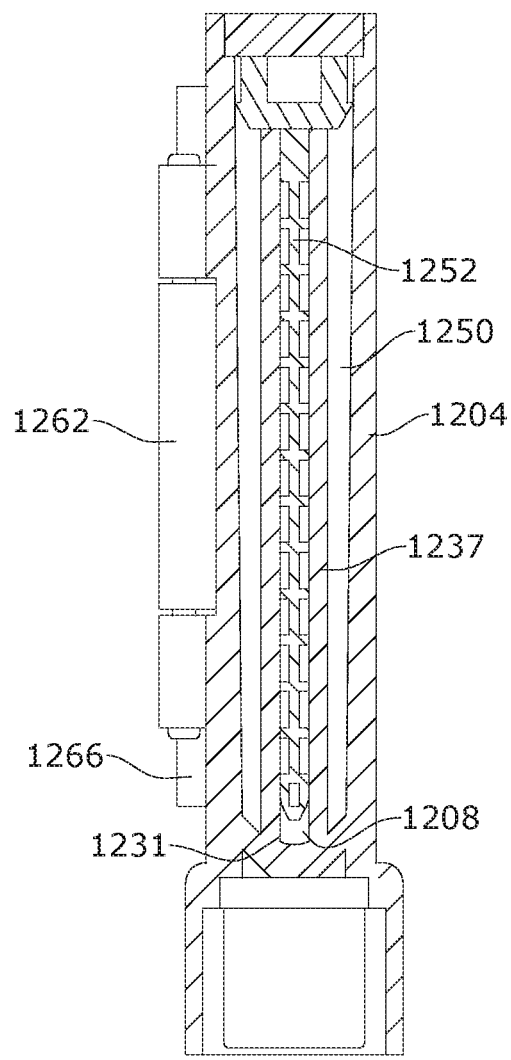
FIG. 48 depicts a cross-sectional view of the device taken along line 19-19 of FIG. 47.

Referring to FIGS. 16A and 16B, the left and right panels show exterior and cross-sectional views, respectively, of a fluid collector 500. The fluid collector 500 includes a spring 555 that is co-axial with the direction of compression of absorbent material 550, such that compression of the absorbent material 550 results in compression of the spring 555, and release of the compressive force causes the spring 555 to assist the return of the absorbent material 550 to the relaxed state, creating suction that draws the fluid sample into the absorbent material 550.

Referring to FIG. 17, a urine cup 600 able to receive a fluid collector has a lid 610 having an opening 615 leading to the interior of supporting member 620 having openings 625 through which the fluid sample can flow, and slot 627 that cooperates with the fluid collector.

Referring to FIG. 18, a fluid sample collector 700 has been inserted through the opening 615 into the interior of the supporting member 620, and a tab 762 disposed on the lower end of the fluid sample collector has engaged slot 627, whereby housing 760 is prevented from rotating relative to the urine collection cup 600. The absorbent material 750 is compressed between the compression member 745 and the lower surface 762 of the housing. When the compressive force is released, a spring 755 co-axial with absorbent material 750 assists the return of absorbent material 750 to the relaxed state, creating suction that helps draw the fluid sample into the absorbent material 750. The sample collection 700 apparatus also includes upper segment 710 having an upper surface 713 through which compressive force is delivered to the absorbent material 750, a closure member 717, a sealing member 718, and a shaft 740.

Referring to FIGS. 19-28, a fluid collection and analyte testing device according with embodiments of the invention are shown. In one embodiment, an analyte testing device 800 includes a fluid collector 812, to collect a fluid sample from a test subject, and a housing 801 to test and retain the fluid sample. The fluid collector 812 may include single or multiple collectors for the collection of the fluid sample. In one embodiment of the invention, a dual-swab split sample testing device, the fluid collector 812 includes a dual collector or a two-prong collector with prongs that are substantially identical, however, a wide variety of modifications to the prongs may be implemented without detracting from the spirit of the invention, including but not limited to, prongs of varying size, shape and materials. Each prong of the fluid collector 812 includes an upper segment 820 having an upper surface, a closure member 814, and sealing members 880; a compression member 890; and a collector 816 made from an absorbent material. A wide variety of absorbent materials capable of acquiring and storing a fluid sample may be used without detracting from the spirit of the invention, including but not limited to a swab, a sponge, and a material that dissolves subsequent to collection of the sample. In one embodiment of the invention, the absorbent material may be saturated with a saliva-producing substance to aid in the collection of the fluid sample. Additionally, the collector 816 may include a sufficiency or visual indicator to indicate when a sufficient amount of the fluid sample is present in the collector 816. U.S. Pat. No. 9,198,641 entitled "Specimen Sample Collection System" describes one prior art sufficiency or visual indicator system and is hereby incorporated by reference. The fluid collector 812 receives a fluid sample from a test subject and temporarily stores the fluid sample until it is transferred to the housing 801. In one embodiment of the invention, the fluid collector 812 receives a fluid sample from a test subject to be used in a split sample fluid testing device.

One advantage of the inventions disclosed herein is the limited amount of test material needed for testing and retention. According to one embodiment of the invention, only four hundred eighty (480) microliters are required for the successful analysis of twelve (12) test strips, forty (40) microliters for each test strip and only seven hundred (700) microliters are required from each prong. The minimum retention amount necessary is approximately the same volume as needed for the test strips. This quantity of a sample is obtainable through the fluid collector described herein. For example, forty (40) by ten (10) millimeter cylindrical collectors 816 collected a fluid, as the test sample, in amounts set forth in the tables below.

TABLE 1

Single-Prong Sample Collection Amount

| Sample | Total Fluid Amount Collected (ml) | Fluid in Chamber after Extraction (ml) | Fluid Loss (ml) | Collection Time (seconds) |
| --- | --- | --- | --- | --- |
| 1 | 1.7 | 1.23 | 0.47 | 67 |
| 2 | 1.5 | 1.13 | 0.37 | 89 |
| 3 | 1.66 | 1.31 | 0.35 | 73 |
| 4 | 1.48 | 1.11 | 0.37 | 105 |
| 5 | 1.36 | 1.04 | 0.32 | 114 |
| 6 | 1.71 | 1.29 | 0.42 | 101 |
| 7 | 1.65 | 1.33 | 0.32 | 113 |
| 8 | 1.36 | 1.03 | 0.33 | 97 |
| Average | 1.55 | 1.18 | 0.37 | 95 |

TABLE 2

Dual-Prong Sample Collection Amount

| Sample | Total Fluid Amount Collected (ml) | Fluid in 1st Chamber after Extraction (ml) | Fluid in 2nd Chamber after Extraction (ml) | Fluid Loss (ml) | Collection Time (seconds) |
| --- | --- | --- | --- | --- | --- |
| 1 | 3.67 | 1.01 | 1.34 | 1.32 | 106 |
| 2 | 3.07 | 1.07 | 1.08 | 0.92 | 128 |
| 3 | 3.23 | 1.22 | 1.10 | 0.91 | 145 |
| 4 | 2.92 | 1.17 | 0.98 | 0.77 | 183 |
| 5 | 3.10 | 1.22 | 1.19 | 0.69 | 124 |
| 6 | 2.78 | 1.14 | 1.05 | 0.59 | 152 |
| 7 | 3.11 | 1.10 | 1.10 | 0.91 | 181 |
| 8 | 2.96 | 1.12 | 1.08 | 0.76 | 133 |
| Average | 3.11 | 1.13 | 1.12 | 0.86 | 144 |

As shown in Tables 1 and 2, the fluid collector 816, according to an embodiment of the invention, on average collects an amount of fluid samples in excess of the amounts required for testing and/or retention in approximately ninety (90)-one hundred fifty (150) seconds. A wide range of collection amounts are anticipated, depending upon the testing requirements, without detracting from the spirit of the invention.

The housing 801 includes a sample receiving member 818 to receive the fluid collector 812. In one embodiment of the invention, the sample receiving member 818 includes two collection chambers 874 to receive the two-pronged fluid collector 812 through two openings 870, thus forming a split sample. The sample receiving member 818 is in fluid communication with a fluid sample retention member, such as a confirmation collection chamber 810, and a test cartridge member 804. The test cartridge member 804 includes a test cartridge chamber 850; a test cartridge 852; at least one membrane test strip 806 located on the test cartridge 852 to indicate the presence or absence of at least one analyte; and a test cartridge fluid reservoir 808 in fluid communication with the test cartridge 852 and the sample receiving member 818. In one embodiment of the invention, the housing 801 includes windows on the front, back or both sides of the housing 801 for viewing of the membrane test strip 806. A wide variety of housings 801 may be implemented without detracting from the spirit of the invention, including but not limited to forming the housing 801 from a clear material allowing the membrane test strips 806 to be viewed without a window. The test cartridge fluid reservoir 808 may be formed in a variety of shapes without detracting from the spirit of the invention, including a v-shaped chamber with a flat bottom 902 as shown in FIG. 10. The test cartridge fluid reservoir 808 with a flat bottom v-shaped chamber 902 allows the test cartridge 852 and membrane test strips 806 to fully engage the fluid sample while maintaining a small volume of the fluid sample. In one embodiment of the invention, the v-shaped chamber with a flat bottom 902 forms a volume of less than seven hundred (700) microliters. An opening 904 at the bottom of the second collection chamber 874 is in fluid connection via a channel 910 with the test cartridge fluid reservoir 808. A wide variety of connection mechanisms may be implemented to connect the second collection chamber 874 and the test cartridge fluid reservoir 808 without detracting from the spirit of the invention, including but not limited to, tubes, piping, channels molded or carved into the housing 801, or any other suitable structure.

In one embodiment of the invention, the sample receiving member 818 includes a first collection chamber 874 in fluid communication with the confirmation collection chamber 810 and a second collection chamber 874 in fluid communication with the test cartridge member 804. The first collection chamber 874 and the confirmation collection chamber 810 are not in fluid communication with any other elements or components of the housing 801, including the second collection chamber 874 and the test cartridge member 804. The second collection chamber 874 is in fluid communication with the test cartridge fluid reservoir 808, which is in fluid communication with the test cartridge 852 and the membrane test strips 806.

Once the fluid collector 812 receives a fluid sample from a test subject, the fluid collector 812 is inserted into the two collection chambers 874 in the sample receiving member 818, through two openings 870. The fluid sample is expelled by compressing the collector 816 between the compression member 890 of both prongs against the bottom surface of the lower portion of the two collection chambers 874, thereby releasing the entrapped fluid into the housing 801. The fluid sample from the test subject is delivered from the first collection chamber 874 to the confirmation collection chamber 810 and from the second collection chamber 874 to the test cartridge fluid reservoir 808. The fluid sample is only obtained a single time with the multiple or two-prong fluid collector 812 while maintaining fluid sample integrity through the collection, storage and analysis of the fluid sample with two distinct storage areas: the confirmation collection chamber 810 and the test cartridge fluid reservoir 808. Once the fluid collector 812 is secured within the housing 801, the fluid sample from the confirmation collection chamber 810 is not in fluid communication with the fluid sample in the test cartridge fluid reservoir 808. The confirmation collection chamber 810 fluid sample may be accessed by a third party as previously disclosed, typically subsequent to the testing of the fluid sample in the test cartridge fluid reservoir 808. In one embodiment of the invention, the confirmation collection chamber 810 is located below the first collection chamber 874. In another embodiment of the invention, the confirmation collection chamber is removable from the housing 801 after the fluid sample is extracted from the collector 812. The fluid collector 812 secures the fluid sample within the sample receiving member 818 with the sealing members 880 to form a seal between the fluid collector and the fluid collection chambers 874. In one embodiment, each prong of the fluid collector 812 includes sealing members 880 located near the top and bottom of the upper segment 820 to seal both of the two collection chambers 874. The sealing members 880 include sealing rings. The sealing rings may be attached at locations close to the top and bottom of the upper segment 820. Generally, the dimensions of sealing members 880, and the sealing rings 28, comport with the interior dimension of the two collection chambers 874 in order to prevent the sample from escaping through the openings 870. Additionally, the fluid collector 812 is secured by the locking closure member 814. In one embodiment of the invention, the locking closure member 814 includes at least one projection extending from the fluid collector 812 that cooperates with the at least one projection located on the inner surface of the sample receiving member 818, where such projections may include for example at least one locking tab and/or at least one annular ring. According to one embodiment of the invention, a closure member on the fluid collector 812 may form a sufficiently secure closure as to constitute means for securing the fluid collector 812 within the sample receiving member 818.

The test cartridge 852 includes slots for one or more membrane test strips 806. In one embodiment of the invention, the test cartridge 852 includes locations or slots for membrane test strips 806 on both the front and back of the test cartridge 852 in a back-to-back formation. The test cartridge 852 may include multiple locations for the membrane test strips 806 on either the front, back or both sides of the test cartridge 852. The test cartridge 852 may allow for a wide number of membrane test strips 806 to be attached to the test cartridge without detracting from the spirit of the invention, including but not limited to, six (6), twelve (12), or twenty-four (24) membrane test strips 806. A wide variety of attachment mechanism may be used to attach the membrane test strips 806 to the test cartridge 852 without detracting to the spirit of the invention, including but not limited to, slotted membrane test strip holders 898 on the test cartridge 852 and a protective sheet attached to the test cartridge 852 that covers and impedes movement of the test strip 806 from the test strip holders 898. After the membrane test strips 806 are attached to the test cartridge 852, the test cartridge 852 is inserted into the test cartridge chamber 850 through a test cartridge chamber opening 872 and is placed between test cartridge guides 906 on both ends of the test cartridge chamber 850. In one embodiment of the invention, the membrane test strips 806 extend beyond the test cartridge 852 into the test cartridge fluid reservoir 808. A test cartridge cap 802 is then inserted into the test cartridge chamber 850 to secure the test cartridge 852 within the housing 801. In one embodiment of the invention, the test cartridge cap 802 is fixedly attached to the test cartridge 852 prior to insertion into the test cartridge chamber 850 or the test cartridge cap 802 and the test cartridge 852 are formed from a continuous material. In another embodiment of the invention, the test cartridge cap 802 attaches to a top edge of the test cartridge chamber opening 872. Advantageously, different versions of the test cartridge 852 may be developed to test different combinations of analytes, thereby allowing the test administrator to select the appropriate analyte test suite at the test site. The test cartridge chamber 850, the test cartridge cap 802, or a combination of both may include a locking mechanism known to those skilled in the art to secure the test cartridge 852 within the test cartridge chamber 850, thereby preventing the removal of the test cartridge 852 from housing 801.

In one embodiment of the invention, the test strips 806 may indicate genomic or proteomic information such that certain DNA sequences or proteins may be detected that are genetic predispositions for certain diseases such as various forms of cancer, diabetes, etc.

The test cartridge 852 and test cartridge cap 802 may be made from a variety of materials without detracting from the spirit of the invention, including but not limited to, plastic, ceramic, metal, glass, wood, rubber, polymer, fiber-reinforced polymer, or any combination thereof. In one embodiment, the test cartridge 852 is formed from plastic and is approximately 70 millimeters in height, 40 millimeters in width, and 5 millimeters in thickness.

After the fluid sample has been expelled from the fluid collector 812 into the test cartridge fluid reservoir 808, the fluid sample encounters the proximal end of the membrane test strip 806 and begins to move upward towards the upper end of the membrane test strip 806 by capillary action. Each membrane test strip 806 generally indicates the presence or absence of at least one analyte. A single drug, or class of drugs, is indicated by each membrane test strip 806, including without limitation, for example, cocaine (COC), amphetamine (AMP), methamphetamine (mAMP), marijuana (THC), methadone (MTD), phencyclidine (PCP), morphine, barbiturates, benzodiazepines, or alcohol. In one embodiment, the test strips 806 may be lateral flow test strips.

In one embodiment, the test cartridge chamber 850 and/or the test cartridge fluid reservoir 808 may be attached to an electrical device that supplies an electric current to the fluid sample. The electrical current may be used to separate elements within the fluid sample prior to testing of the fluid sample.

The housing may include an immunoassay-based fingerprint acquisition pad 860 to positively identify an individual associated with the fluid collection and analyte test. In one embodiment of the invention, the second collection chamber and/or the test cartridge fluid reservoir 808 may be in fluid communication with the immunoassay-based fingerprint acquisition pad 860. The immunoassay-based fingerprint acquisition pad 860 may be removably connected to the housing 801 or fixedly attached to the housing 801. The immunoassay-based fingerprint acquisition pad 860 is enclosed by a cover 866 that is held closed by closure member 864 and pivots into the opened position on the axis defined by the hinges 862. The door 866 may be secured after the fingerprint of the test subject has been acquired, using various locking mechanisms, including without limitation a tab-and-slot arrangement, or security tape.

The immunoassay-based fingerprint acquisition pad 860 may be a stand-alone apparatus connected to the housing 801 or the immunoassay-based fingerprint acquisition pad 860 may be in fluid communication with the test cartridge fluid reservoir 808. The immunoassay-based fingerprint acquisition pad 860 in fluid communication with the test cartridge fluid reservoir 808 functions as previously disclosed.

In an embodiment of the invention, the immunoassay-based fingerprint acquisition pad 860 includes a compressible, porous reaction medium, having a control zone and a plurality of reaction zones, arranged on a porous support. The control zone includes a control reagent to identify the fluid sample donor, and each reaction zone includes a reaction reagent to determine the presence of a specific analyte in the fluid sample. The control reagent includes a member of a predetermined ligand/receptor binding pair. Similarly, each reaction reagent includes a member of a predetermined ligand/receptor binding pair. Various ligand/receptor binding pairs for use within the control and reaction zones are discussed within the '863 and '815 patents.

In an embodiment of the invention, the immunoassay-based fingerprint acquisition pad 860 is fluidly coupled to the collection chamber 874. A signal-producing agent, located on upper surface of the porous support or the lower surface of the reaction medium, mixes with the fluid sample provided to the immunoassay-based fingerprint acquisition pad 860. The production of an image or pattern which identifies the person providing the sample is accomplished by applying a fingertip to the upper surface of the reaction medium and compressing the reaction medium so that the fluid sample/signal-producing agent mixture permeates the reaction medium, and allowing the control zone ligand/receptor reaction to take place so that the members of this immunological pair bond with the signal-producing agent and produce the fingerprint image. Similarly, the presence or absence of a specific analyte in the fluid sample is indicated within each reaction zone by the reaction of each specific reaction reagent with the fluid sample/signal-producing agent mixture.

Referring to FIGS. 29-35, a fluid collection and analyte testing device according with embodiments of the invention are shown. In one embodiment, an analyte testing device 900 includes a fluid collector 912, to collect a fluid sample from a test subject, and a housing 901 to test and retain the fluid sample. The fluid collector 912 may include a single prong for the collection of the fluid sample. The prong of the fluid collector 912 includes an upper segment 920 having an upper surface, a closure member 914, and sealing members 918; a compression member 990; and a collector 916 made from an absorbent material.

A wide variety of absorbent materials capable of acquiring and storing a fluid sample may be used without detracting from the spirit of the invention, including but not limited to a swab, a sponge, and a material that dissolves subsequent to collection of the sample. In one embodiment of the invention, the absorbent material may be saturated with a saliva-producing substance to aid in the collection of the fluid sample. Additionally, the collector 916 may include a sufficiency or visual indicator to indicate when a sufficient amount of the fluid sample is present in the collector 916. U.S. Pat. No. 9,198,641 entitled "Specimen Sample Collection System" describes one prior art sufficiency or visual indicator system and is hereby incorporated by reference. The fluid collector 912 receives a fluid sample from a test subject and temporarily stores the fluid sample until it is transferred to the housing 901.

The housing 901 includes a sample receiving member 980 to receive the fluid collector 912. In one embodiment of the invention, the sample receiving member 980 includes a collection chamber 974 to receive the fluid collector 912 through an opening 970. The sample receiving member 980 is in fluid communication with a fluid sample retention member, such as a confirmation collection chamber 955, and a test cartridge member 914. The test cartridge member 914 includes a test cartridge chamber 950; a test cartridge 952; at least one membrane test strip 916 located on the test cartridge 952 to indicate the presence or absence of at least one analyte; and a test cartridge fluid reservoir 917 in fluid communication with the test cartridge 952 and the sample receiving member 980. In one embodiment of the invention, the housing 901 includes windows on the front, back or both sides of the housing 901 for viewing of the membrane test strip 916. A wide variety of housings 901 may be implemented without detracting from the spirit of the invention, including but not limited to forming the housing 901 from a clear material allowing the membrane test strips 916 to be viewed without a window.

The test cartridge fluid reservoir 917 may be formed in a variety of shapes without detracting from the spirit of the invention, including a v-shaped chamber with a flat bottom 931. The test cartridge fluid reservoir 917 with the v-shaped chamber with the flat bottom 931 allows the test cartridge 952 and membrane test strips 916 to fully engage the fluid sample while maintaining a small volume of the fluid sample. In one embodiment of the invention, the v-shaped chamber with a flat bottom 931 forms a volume of less than seven hundred (700) microliters. An opening 913 at the bottom of the collection chamber 974 is in fluid connection via a channel 919 with the test cartridge fluid reservoir 917. A wide variety of connection mechanisms may be implemented to connect the collection chamber 974 and the test cartridge fluid reservoir 917 without detracting from the spirit of the invention, including but not limited to, tubes, piping, channels molded or carved into the housing 901, or any other suitable structure.

In one embodiment of the invention, the sample receiving member 980 includes the collection chamber 974 in fluid communication with the confirmation collection chamber 955 and in fluid communication with the test cartridge member 914.

Once the fluid collector 912 receives a fluid sample from a test subject, the fluid collector 912 is inserted into the collection chamber 974 of the sample receiving member 980, through the opening 970. The fluid sample is expelled by compressing the collector 916 between the compression member 990 of the prong against the bottom surface of the lower portion of the collection chamber 974, thereby releasing the entrapped fluid into the housing 901. The fluid sample from the test subject is delivered from the collection chamber 974 to the confirmation collection chamber 955 and from the collection chamber 974 to the test cartridge fluid reservoir 917. The fluid sample is only obtained a single time with the fluid collector 912 while maintaining fluid sample integrity through the collection, storage and analysis of the fluid sample with two distinct storage areas: the confirmation collection chamber 955 and the test cartridge fluid reservoir 917. Once the fluid collector 912 is secured within the housing 901, the fluid sample from the confirmation collection chamber 955 is not in fluid communication with the fluid sample in the test cartridge fluid reservoir 917. The confirmation collection chamber 955 fluid sample may be accessed by a third party as previously disclosed, typically subsequent to the testing of the fluid sample in the test cartridge fluid reservoir 917. In one embodiment of the invention, the confirmation collection chamber 955 is located below the collection chamber 974. In another embodiment of the invention, the confirmation collection chamber 955 is removable from the housing 901 after the fluid sample is extracted from the collector 912 via a threaded connection 953.

The fluid collector 912 secures the fluid sample within the sample receiving member 980 with the sealing members 918 to form a seal between the fluid collector 912 and the fluid collection chambers 974. In one embodiment, the fluid collector 912 includes sealing members 918 located near the top and bottom of the upper segment 920 to seal both of the two collection chambers 974. The sealing members 918 may include sealing rings. The sealing rings may be attached at locations close to the top and bottom of the upper segment 920. Generally, the dimensions of sealing members 918 comport with the interior dimension of the collection chamber 974 in order to prevent the sample from escaping through the openings 970. Once the fluid collector 912 has been inserted into the sample receiving member 980, a locking mechanism 981, 934 prevents the removal of the fluid collector 912 from the sample receiving member 980. The locking mechanism 981, 934 includes locking tabs 981 laterally extending from the closure member 914 and locking slots 934 located near the top of the sample receiving members 980. When the fluid collector 912 is inserted into the sample receiving member 980, the locking tabs 981 insert into the locking slots 934, locking the fluid collector 912 within the sample receiving member 980.

The test cartridge 952 includes slots for one or more membrane test strips 916. In one embodiment of the invention, the test cartridge 952 includes locations or slots for membrane test strips 916 on both the front and back of the test cartridge 952 in a back-to-back formation. The test cartridge 952 may include multiple locations for the membrane test strips 916 on either the front, back or both sides of the test cartridge 952. The test cartridge 952 may allow for a wide number of membrane test strips 916 to be attached to the test cartridge without detracting from the spirit of the invention, including but not limited to, six (6), twelve (12), or twenty-four (24) membrane test strips 916. A wide variety of attachment mechanism may be used to attach the membrane test strips 916 to the test cartridge 952 without detracting to the spirit of the invention, including but not limited to, slotted membrane test strip holders 998 on the test cartridge 952 and a protective sheet attached to the test cartridge 952 that covers and impedes movement of the test strip 916 from the test strip holders 998. After the membrane test strips 916 are attached to the test cartridge 952, the test cartridge 952 is inserted into the test cartridge chamber 950 through a test cartridge chamber opening 972 and is placed between test cartridge guides 937 on both ends of the test cartridge chamber 950. In one embodiment of the invention, the membrane test strips 916 extend beyond the test cartridge 952 into the test cartridge fluid reservoir 917. A test cartridge cap 971 and a test cartridge seal 932 is then inserted into the test cartridge chamber 950 to secure the test cartridge 952 within the housing 901. In one embodiment of the invention, the test cartridge cap 971 is fixedly attached to the test cartridge 952 prior to insertion into the test cartridge chamber 950 or the test cartridge cap 971 and the test cartridge 952 are formed from a continuous material. In another embodiment of the invention, the test cartridge cap 971 attaches to a top edge of the test cartridge chamber opening 972. Advantageously, different versions of the test cartridge 952 may be developed to test different combinations of analytes, thereby allowing the test administrator to select the appropriate analyte test suite at the test site. The test cartridge chamber 950, the test cartridge cap 971, or a combination of both may include a locking mechanism 928, 938 to secure the test cartridge 952 within the test cartridge chamber 950, thereby preventing the removal of the test cartridge 952 from the housing 901. For example, the locking mechanism 928, 938 includes locking tabs 928 extending laterally from the test cartridge cap 971 that insert into the locking slots 938 formed on the top edge of the test cartridge chamber opening 972, thereby locking the test cartridge 952 within the test cartridge chamber 950.

In one embodiment of the invention, the test strips 916 may indicate genomic or proteomic information such that certain DNA sequences or proteins may be detected that are genetic predispositions for certain diseases such as various forms of cancer, diabetes, etc.

The test cartridge 952 and test cartridge cap 971 may be made from a variety of materials without detracting from the spirit of the invention, including but not limited to, plastic, ceramic, metal, glass, wood, rubber, polymer, fiber-reinforced polymer, or any combination thereof. In one embodiment, the test cartridge 952 is formed from plastic and is approximately 70 millimeters in height, 40 millimeters in width, and 5 millimeters in thickness.

After the fluid sample has been expelled from the fluid collector 912 into the test cartridge fluid reservoir 917, the fluid sample encounters the proximal end of the membrane test strip 916 and begins to move upward towards the upper end of the membrane test strip 916 by capillary action. Each membrane test strip 916 generally indicates the presence or absence of at least one analyte. A single drug, or class of drugs, is indicated by each membrane test strip 916, including without limitation, for example, cocaine (COC), amphetamine (AMP), methamphetamine (mAMP), marijuana (THC), methadone (MTD), phencyclidine (PCP), morphine, barbiturates, benzodiazepines, or alcohol. In one embodiment, the test strips 806 may be lateral flow test strips.

In one embodiment, the test cartridge chamber 950 and/or the test cartridge fluid reservoir 917 may be attached to an electrical device that supplies an electric current to the fluid sample. The electrical current may be used to separate elements within the fluid sample prior to testing of the fluid sample.

The housing may include an immunoassay-based fingerprint acquisition pad 960 to positively identify an individual associated with the fluid collection and analyte test. In one embodiment of the invention, the collection chamber 974 and/or the test cartridge fluid reservoir 917 may be in fluid communication with the immunoassay-based fingerprint acquisition pad 960. The immunoassay-based fingerprint acquisition pad 960 may be removably connected to the housing 901 or fixedly attached to the housing 901. The immunoassay-based fingerprint acquisition pad 960 is enclosed by a cover 966 that is held closed by closure member and pivots into the opened position on the axis defined by the hinges 962. The cover 966 may be secured after the fingerprint of the test subject has been acquired, using various locking mechanisms, including without limitation a tab-and-slot arrangement, or security tape.

The immunoassay-based fingerprint acquisition pad 960 may be a stand-alone apparatus connected to the housing 901 or the immunoassay-based fingerprint acquisition pad 960 may be in fluid communication with the test cartridge fluid reservoir 917. The immunoassay-based fingerprint acquisition pad 960 in fluid communication with the test cartridge fluid reservoir 917 functions as previously disclosed.

In an embodiment of the invention, the immunoassay-based fingerprint acquisition pad 960 includes a compressible, porous reaction medium, having a control zone and a plurality of reaction zones, arranged on a porous support. The control zone includes a control reagent to identify the fluid sample donor, and each reaction zone includes a reaction reagent to determine the presence of a specific analyte in the fluid sample. The control reagent includes a member of a predetermined ligand/receptor binding pair. Similarly, each reaction reagent includes a member of a predetermined ligand/receptor binding pair. Various ligand/receptor binding pairs for use within the control and reaction zones are discussed within the '863 and '815 patents.

In an embodiment of the invention, the immunoassay-based fingerprint acquisition pad 960 is fluidly coupled to the collection chamber 974. A signal-producing agent, located on upper surface of the porous support or the lower surface of the reaction medium, mixes with the fluid sample provided to the immunoassay-based fingerprint acquisition pad 960. The production of an image or pattern which identifies the person providing the sample is accomplished by applying a fingertip to the upper surface of the reaction medium and compressing the reaction medium so that the fluid sample/signal-producing agent mixture permeates the reaction medium and allowing the control zone ligand/receptor reaction to take place so that the members of this immunological pair bond with the signal-producing agent and produce the fingerprint image. Similarly, the presence or absence of a specific analyte in the fluid sample is indicated within each reaction zone by the reaction of each specific reaction reagent with the fluid sample/signal-producing agent mixture.

Referring to FIGS. 36-42, a fluid collection and analyte testing device according with embodiments of the invention are shown. In one embodiment, an analyte testing device 1000 includes a fluid collector 1012, to collect a fluid sample from a test subject, and a housing 1001 to test and retain the fluid sample. In one embodiment of the invention, the fluid collector 1012 is used to collect a blood sample from a patient. The fluid collector 1012 includes dual prongs including a first prong for penetrating a user's skin or oral mucosa and a second prong to collect fluid. Each prong of the fluid collector 1012 includes an upper segment 1020 having an upper surface, a closure member 1014, and sealing members 1080. The first prong further includes a lancet slot 1097 and a lancet 1004 coupled to the lancet slot 1097. The second prong further includes a compression member 1090 and a collector 1016 made from an absorbent material.

The lancet 1004 is utilized for penetrating the skin or oral mucosa of a human or animal subject at a lancing site to obtain a sample of blood or other body fluid for medical testing. The lancet 1004 includes a housing containing a drive mechanism with a drive spring, a charging mechanism for energizing the spring, and a release mechanism for releasing the drive mechanism to propel the lancet through a lancing stroke. The lancet 1004 is propelled by the drive mechanism from a retracted position within the housing to an extended position where a sharp tip portion of the lancet projects from the housing to prick the subjects skin or oral mucosa at a desired lancing site. The lancet 1004 of the present invention may include two springs, a drive spring to drive the lancet along an advancing portion of the lancet stroke toward the lancing site, and a return spring to retract the lancet along a return portion of the lancet stroke back into the housing.

The collector 1016 may include a wide variety of absorbent materials capable of acquiring and storing a fluid sample without detracting from the spirit of the invention, including but not limited to a swab, a sponge, and a material that dissolves subsequent to collection of the sample. Additionally, the collector 1016 may include a sufficiency or visual indicator 1023 to indicate when a sufficient amount of the fluid sample is present in the collector 1016. U.S. Pat. No. 9,198,641 entitled "Specimen Sample Collection System" describes one prior art sufficiency or visual indicator system and is hereby incorporated by reference. The lancet 1004 penetrates a test subject's skin, causing the test subject to bleed. The fluid collector 1016 receives a blood sample from a test subject and temporarily stores the blood sample until it is transferred to the housing 1001. In one embodiment of the invention, the fluid collector 1012 receives a blood sample from a test subject to be used in a split sample fluid.

The housing 1001 includes a sample receiving member 1018 to receive the fluid collector 1012. In one embodiment of the invention, the sample receiving member 1018 includes a collection chamber 1074 to receive the fluid collector 1012 through an opening 1070. The sample receiving member 1018 is in fluid communication with a fluid sample retention member, such as a confirmation collection chamber 1055, and a test cartridge member 1014. The test cartridge member 1014 includes a test cartridge chamber 1050; a test cartridge 1052; at least one membrane test strip 1016 located on the test cartridge 1052 to indicate the presence or absence of at least one analyte; and a test cartridge fluid reservoir 1017 in fluid communication with the test cartridge 1052 and the sample receiving member 1018. In one embodiment of the invention, the housing 1001 includes windows on the front, back or both sides of the housing 1001 for viewing of the membrane test strip 1016. A wide variety of housings 1001 may be implemented without detracting from the spirit of the invention, including but not limited to forming the housing 1001 from a clear material allowing the membrane test strips 1016 to be viewed without a window.

The test cartridge fluid reservoir 1017 may be formed in a variety of shapes without detracting from the spirit of the invention, including a v-shaped chamber with a flat bottom 1031. The test cartridge fluid reservoir 1017 with the v-shaped chamber with a flat bottom 1031 allows the test cartridge 1052 and membrane test strips 1016 to fully engage the blood sample while maintaining a small volume of the blood sample. In one embodiment of the invention, the v-shaped chamber with a flat bottom 1031 forms a volume of less than seven hundred (700) microliters. An opening 1013 at the bottom of the collection chamber 1074 is in fluid connection via a channel 1019 with the test cartridge fluid reservoir 1017. A wide variety of connection mechanisms may be implemented to connect the collection chamber 1074 and the test cartridge fluid reservoir 1017 without detracting from the spirit of the invention, including but not limited to, tubes, piping, channels molded or carved into the housing 1001, or any other suitable structure.

In one embodiment of the invention, the sample receiving member 1018 includes the collection chamber 1074 in fluid communication with the confirmation collection chamber 1055 and in fluid communication with the test cartridge member 1014.

Once the fluid collector 1012 receives a blood sample from a test subject, the fluid collector 1012 is inserted into the collection chambers 1074 in the sample receiving member 1018, through the opening 1070. The blood sample is expelled by compressing the collector 1016 between the compression member 1090 of the prong against the bottom surface of the lower portion of the collection chamber 1074, thereby releasing the entrapped blood into the housing 1001. The blood sample from the test subject is delivered from the collection chamber 1074 to the confirmation collection chamber 1055 and from the collection chamber 1074 to the test cartridge fluid reservoir 1017. The blood sample is only obtained a single time with the fluid collector 1012 while maintaining blood sample integrity through the collection, storage and analysis of the blood sample with two distinct storage areas: the confirmation collection chamber 1055 and the test cartridge fluid reservoir 1017. Once the fluid collector 1012 is secured within the housing 1001, the blood sample from the confirmation collection chamber 1055 is not in fluid communication with the blood sample in the test cartridge fluid reservoir 1017. The confirmation collection chamber 1055 blood sample may be accessed by a third party as previously disclosed, typically subsequent to the testing of the blood sample in the test cartridge fluid reservoir 1017. In one embodiment of the invention, the confirmation collection chamber 1055 is located below the collection chamber 1074. In another embodiment of the invention, the confirmation collection chamber 1055 is removable from the housing 1001 after the blood sample is extracted from the collector 1012 via a threaded connection 1053.

The fluid collector 1012 secures the blood sample within the sample receiving member 1018 with the sealing members 1080 to form a seal between the fluid collector 1012 and the fluid collection chambers 1074. In one embodiment, the fluid collector 1012 includes sealing members 1080 located near the top and bottom of the upper segment 1020 to seal both of the two collection chambers 1074. The sealing members 1080 include sealing rings. The sealing rings may be attached at locations close to the top and bottom of the upper segment 1020. Generally, the dimensions of sealing members 1080 comport with the interior dimension of the collection chamber 1074 in order to prevent the sample from escaping through the openings 1070. Once the fluid collector 1012 has been inserted into the sample receiving member 1018, a locking mechanism 1081, 1034 prevents the removal of the fluid collector 1012 from the sample receiving member 1018. The locking mechanism 1081, 1034 includes locking tabs 1081 laterally extending from the closure member 1014 and locking slots 1034 located near the top of the sample receiving members 1018. When the fluid collector 1012 is inserted into the sample receiving member 1018, the locking tabs 1081 insert into the locking slots 1034, locking the fluid collector 1012 within the sample receiving member 1018.

The test cartridge 1052 includes slots for one or more membrane test strips 1016. In one embodiment of the invention, the test cartridge 1052 includes locations or slots for membrane test strips 1016 on both the front and back of the test cartridge 1052 in a back-to-back formation. The test cartridge 1052 may include multiple locations for the membrane test strips 1016 on either the front, back or both sides of the test cartridge 1052. The test cartridge 1052 may allow for a wide number of membrane test strips 1016 to be attached to the test cartridge without detracting from the spirit of the invention, including but not limited to, six (6), twelve (12), or twenty-four (24) membrane test strips 1016. A wide variety of attachment mechanism may be used to attach the membrane test strips 1016 to the test cartridge 1052 without detracting to the spirit of the invention, including but not limited to, slotted membrane test strip holders 1098 on the test cartridge 1052 and a protective sheet attached to the test cartridge 1052 that covers and impedes movement of the test strip 1016 from the test strip holders 1098. After the membrane test strips 1016 are attached to the test cartridge 1052, the test cartridge 1052 is inserted into the test cartridge chamber 1050 through a test cartridge chamber opening 1072 and is placed between test cartridge guides 1037 on both ends of the test cartridge chamber 1050. In one embodiment of the invention, the membrane test strips 1016 extend beyond the test cartridge 1052 into the test cartridge fluid reservoir 1017. A test cartridge cap 1071 and a test cartridge seal 1032 is then inserted into the test cartridge chamber 1050 to secure the test cartridge 1052 within the housing 1001. In one embodiment of the invention, the test cartridge cap 1071 is fixedly attached to the test cartridge 1052 prior to insertion into the test cartridge chamber 1050 or the test cartridge cap 1071 and the test cartridge 1052 are formed from a continuous material. In another embodiment of the invention, the test cartridge cap 1071 attaches to a top edge of the test cartridge chamber opening 1072. Advantageously, different versions of the test cartridge 1052 may be developed to test different combinations of analytes, thereby allowing the test administrator to select the appropriate analyte test suite at the test site. The test cartridge chamber 1050, the test cartridge cap 1071, or a combination of both may include a locking mechanism 1028, 1038 to secure the test cartridge 1052 within the test cartridge chamber 1050, thereby preventing the removal of the test cartridge 1052 from housing 1001. For example, the locking mechanism 1028, 1038 includes locking tabs 1028 extending laterally from the test cartridge cap 1071 that insert into the locking slots 1038 formed on the top edge of the test cartridge chamber opening 1072, thereby locking the test cartridge 1052 within the test cartridge chamber 1050.

The test cartridge 1052 and test cartridge cap 1071 may be made from a variety of materials without detracting from the spirit of the invention, including but not limited to, plastic, ceramic, metal, glass, wood, rubber, polymer, fiber-reinforced polymer, or any combination thereof. In one embodiment, the test cartridge 1052 is formed from plastic and is approximately 70 millimeters in height, 40 millimeters in width, and 5 millimeters in thickness.

After the fluid sample has been expelled from the fluid collector 1012 into the test cartridge fluid reservoir 1017, the fluid sample encounters the proximal end of the membrane test strip 1016 and begins to move upward towards the upper end of the membrane test strip 1016 by capillary action. Each membrane test strip 1016 generally indicates the presence or absence of at least one analyte. A single drug, or class of drugs, is indicated by each membrane test strip 1016, including without limitation, for example, cocaine (COC), amphetamine (AMP), methamphetamine (mAMP), marijuana (THC), methadone (MTD), phencyclidine (PCP), morphine, barbiturates, benzodiazepines, or alcohol. In one embodiment, the test strips 806 may be lateral flow test strips. In one embodiment of the invention, the test strips 1016 may indicate genomic or proteomic information such that certain DNA sequences or proteins may be detected that are genetic predispositions for certain diseases such as various forms of cancer, diabetes, etc.

In one embodiment, the test cartridge chamber 1050 and/or the test cartridge fluid reservoir 1017 may be attached to an electrical device that supplies an electric current to the fluid sample. The electrical current may be used to separate elements within the fluid sample prior to testing of the fluid sample.

In certain embodiments, multiple fluid collection and analyte testing devices 1000, 1100 are releasably coupled together to collect and test different types of fluids of the patient. For example, the fluid collection and analyte testing device 1000 for collecting blood samples may be releasably coupled with a fluid collection and analyte testing device 1100 for collecting saliva samples or urine samples. In such embodiments, the housing 1001 of the analyte testing device 1000 includes rear connector hooks 1022 and a housing 1101 of the analyte testing device 1100 includes rear connector hooks 1122. The rear connector hooks 1022, 1122 slidably engage one another, thereby releasably coupling the analyte testing devices 1000, 1100 together. Using such embodiments allows the collection and testing of multiple types of fluid samples from a single test subject.

The analyte testing device 1100 for collecting saliva or urine includes a fluid collector 1112, to collect a fluid sample from a test subject, and a housing 1101 to test and retain the fluid sample. The fluid collector 1112 may include single or multiple collectors for the collection of the fluid sample. In one embodiment of the invention, a dual-swab split sample testing device, the fluid collector 1112 includes a dual collector or a two-prong collector with prongs that are substantially identical, however, a wide variety of modifications to the prongs may be implemented without detracting from the spirit of the invention, including but not limited to, prongs of varying size, shape and materials. Each prong of the fluid collector 1112 includes an upper segment 1120 having an upper surface, a closure member 1114, and sealing members 1180; a compression member 1190; and a collector 1116 made from an absorbent material. A wide variety of absorbent materials capable of acquiring and storing a fluid sample may be used without detracting from the spirit of the invention, including but not limited to a swab, a sponge, and a material that dissolves subsequent to collection of the sample. In one embodiment of the invention, the absorbent material may be saturated with a saliva-producing substance to aid in the collection of the fluid sample. Additionally, the collector 1116 may include a sufficiency or visual indicator to indicate when a sufficient amount of the fluid sample is present in the collector 1116. The fluid collector 1112 receives a fluid sample from a test subject and temporarily stores the fluid sample until it is transferred to the housing 1101. In one embodiment of the invention, the fluid collector 1112 receives a fluid sample from a test subject to be used in a split sample fluid testing device.

The housing 1101 includes a sample receiving member 1118 to receive the fluid collector 1112. In one embodiment of the invention, the sample receiving member 1118 includes two collection chambers 1174 to receive the two-pronged fluid collector 1112 through two openings 1170, thus forming a split sample. The sample receiving member 1118 is in fluid communication with a fluid sample retention member, such as a confirmation collection chamber 1155, and a test cartridge member 1114. The test cartridge member 1114 includes a test cartridge chamber 1150; a test cartridge 1152; at least one membrane test strip 1106 located on the test cartridge 1152 to indicate the presence or absence of at least one analyte; and a test cartridge fluid reservoir 1117 in fluid communication with the test cartridge 1152 and the sample receiving member 1118. In one embodiment of the invention, the housing 1101 includes windows on the front, back or both sides of the housing 1101 for viewing of the membrane test strip 1106. A wide variety of housings 1101 may be implemented without detracting from the spirit of the invention, including but not limited to forming the housing 1101 from a clear material allowing the membrane test strips 1106 to be viewed without a window.

The test cartridge fluid reservoir 1117 may be formed in a variety of shapes without detracting from the spirit of the invention, including a v-shaped chamber with a flat bottom 1131. The test cartridge fluid reservoir 1117 with the v-shaped chamber with a flat bottom 1131 allows the test cartridge 1152 and membrane test strips 1106 to fully engage the fluid sample while maintaining a small volume of the fluid sample. In one embodiment of the invention, the v-shaped chamber with a flat bottom 1131 forms a volume of less than seven hundred (700) microliters. An opening 1113 at the bottom of the second collection chamber 1174 is in fluid connection via a channel 1119 with the test cartridge fluid reservoir 1117. A wide variety of connection mechanisms may be implemented to connect the second collection chamber 1174 and the test cartridge fluid reservoir 1117 without detracting from the spirit of the invention, including but not limited to, tubes, piping, channels molded or carved into the housing 1101, or any other suitable structure.

In one embodiment of the invention, the sample receiving member 1118 includes a first collection chamber 1174 in fluid communication with the confirmation collection chamber 1155 and a second collection chamber 1174 in fluid communication with the test cartridge member 1114. The first collection chamber 1174 and the confirmation collection chamber 1155 are not in fluid communication with any other elements or components of the housing 1101, including the second collection chamber 1174 and the test cartridge member 1114. The second collection chamber 1174 is in fluid communication with the test cartridge fluid reservoir 1117, which is in fluid communication with the test cartridge 1152 and the membrane test strips 1106.

Once the fluid collector 1112 receives a fluid sample from a test subject, the fluid collector 1112 is inserted into the two collection chambers 1174 in the sample receiving member 1118, through two openings 1170. The fluid sample is expelled by compressing the collector 1116 between the compression member 1190 of both prongs against the bottom surface of the lower portion of the two collection chambers 1174, thereby releasing the entrapped fluid into the housing 1101. The fluid sample from the test subject is delivered from the first collection chamber 1174 to the confirmation collection chamber 1155 and from the second collection chamber 1174 to the test cartridge fluid reservoir 1117. The fluid sample is only obtained a single time with the multiple or two-prong fluid collector 1112 while maintaining fluid sample integrity through the collection, storage and analysis of the fluid sample with two distinct storage areas: the confirmation collection chamber 1155 and the test cartridge fluid reservoir 1117.

Once the fluid collector 1112 is secured within the housing 1101, the fluid sample from the confirmation collection chamber 1155 is not in fluid communication with the fluid sample in the test cartridge fluid reservoir 1117. The confirmation collection chamber 1155 fluid sample may be accessed by a third party as previously disclosed, typically subsequent to the testing of the fluid sample in the test cartridge fluid reservoir 1117. In one embodiment of the invention, the confirmation collection chamber 1155 is located below the first collection chamber 1174. In another embodiment of the invention, the confirmation collection chamber 1155 is removable from the housing 1101 after the fluid sample is extracted from the collector 1112 via a threaded connection 1153.

The fluid collector 1112 secures the fluid sample within the sample receiving member 1118 with the sealing members 1180 to form a seal between the fluid collector and the fluid collection chambers 1174. In one embodiment, each prong of the fluid collector 1112 includes sealing members 1180 located near the top and bottom of the upper segment 1120 to seal both of the two collection chambers 1174. The sealing members 1180 include sealing rings. The sealing rings may be attached at locations close to the top and bottom of the upper segment 1120. Generally, the dimensions of sealing members 1180, and the sealing rings, comport with the interior dimension of the two collection chambers 1174 in order to prevent the sample from escaping through the openings 1170. Once the fluid collector 1112 has been inserted into the sample receiving member 1118, a locking mechanism 1181, 1134 prevents the removal of the fluid collector 1112 from the sample receiving member 1118. The locking mechanism 1181, 1134 includes locking tabs 1181 laterally extending from the closure member 1114 and locking slots 1134 located near the top of the sample receiving members 1118. When the fluid collector 1112 is inserted into the sample receiving member 1118, the locking tabs 1181 insert into the locking slots 1134, locking the fluid collector 1112 within the sample receiving member 1118.

The test cartridge 1152 includes slots for one or more membrane test strips 1106. In one embodiment of the invention, the test cartridge 1152 includes locations or slots for membrane test strips 1106 on both the front and back of the test cartridge 1152 in a back-to-back formation. The test cartridge 1152 may include multiple locations for the membrane test strips 1106 on either the front, back or both sides of the test cartridge 1152. The test cartridge 1152 may allow for a wide number of membrane test strips 1106 to be attached to the test cartridge without detracting from the spirit of the invention, including but not limited to, six (6), twelve (12), or twenty-four (24) membrane test strips 1106. A wide variety of attachment mechanism may be used to attach the membrane test strips 1106 to the test cartridge 1152 without detracting to the spirit of the invention, including but not limited to, slotted membrane test strip holders 1198 on the test cartridge 1152 and a protective sheet attached to the test cartridge 1152 that covers and impedes movement of the test strip 1106 from the test strip holders 1198. After the membrane test strips 1106 are attached to the test cartridge 1152, the test cartridge 1152 is inserted into the test cartridge chamber 1150 through a test cartridge chamber opening 1172 and is placed between test cartridge guides 1137 on both ends of the test cartridge chamber 1150. In one embodiment of the invention, the membrane test strips 1106 extend beyond the test cartridge 1152 into the test cartridge fluid reservoir 1117. A test cartridge cap 1171 and a test cartridge seal 1132 are then inserted into the test cartridge chamber 1150 to secure the test cartridge 1152 within the housing 1101. In one embodiment of the invention, the test cartridge cap 1171 is fixedly attached to the test cartridge 1152 prior to insertion into the test cartridge chamber 1150 or the test cartridge cap 1171 and the test cartridge 1152 are formed from a continuous material. In another embodiment of the invention, the test cartridge cap 1171 attaches to a top edge of the test cartridge chamber opening 1172. Advantageously, different versions of the test cartridge 1152 may be developed to test different combinations of analytes, thereby allowing the test administrator to select the appropriate analyte test suite at the test site. The test cartridge chamber 1150, the test cartridge cap 1171, or a combination of both may include a locking mechanism 1128, 1138 to secure the test cartridge 1152 within the test cartridge chamber 1150, thereby preventing the removal of the test cartridge 1152 from housing 1101. For example, the locking mechanism 1128, 1138 includes locking tabs 1128 extending laterally from the test cartridge cap 1171 that insert into the locking slots 1138 formed on the top edge of the test cartridge chamber opening 1172, thereby locking the test cartridge 1152 within the test cartridge chamber 1150.

The test cartridge 1152 and test cartridge cap 1171 may be made from a variety of materials without detracting from the spirit of the invention, including but not limited to, plastic, ceramic, metal, glass, wood, rubber, polymer, fiber-reinforced polymer, or any combination thereof. In one embodiment, the test cartridge 1152 is formed from plastic and is approximately 70 millimeters in height, 40 millimeters in width, and 5 millimeters in thickness.

After the fluid sample has been expelled from the fluid collector 1112 into the test cartridge fluid reservoir 1117, the fluid sample encounters the proximal end of the membrane test strip 1106 and begins to move upward towards the upper end of the membrane test strip 1106 by capillary action. Each membrane test strip 1106 generally indicates the presence or absence of at least one analyte. A single drug, or class of drugs, is indicated by each membrane test strip 1106, including without limitation, for example, cocaine (COC), amphetamine (AMP), methamphetamine (mAMP), marijuana (THC), methadone (MTD), phencyclidine (PCP), morphine, barbiturates, benzodiazepines, or alcohol. In one embodiment, the test strips 1106 may be lateral flow test strips. In one embodiment of the invention, the test strips 1106 may indicate genomic or proteomic information such that certain DNA sequences or proteins may be detected that are genetic predispositions for certain diseases such as various forms of cancer, diabetes, etc.

In one embodiment, the test cartridge chamber 1150 and/or the test cartridge fluid reservoir 1117 may be attached to an electrical device that supplies an electric current to the fluid sample. The electrical current may be used to separate elements within the fluid sample prior to testing of the fluid sample.

Referring to FIGS. 44-48, a fluid collection and analyte testing device according with embodiments of the invention are shown. In one embodiment, an analyte testing device 1200 includes a first fluid collector 1212a and a second fluid collector 1212b, to collect a fluid sample from a test subject, and a housing 1201 to test and retain the fluid sample. The first fluid collector 1212a includes a dual collector or a two-prong collector with prongs that are substantially identical. Each prong of the first fluid collector 1212a includes an upper segment 1220a having an upper surface, a closure member 1214a, and sealing members 1280a; a compression member 1290a; and a collector 1216a made from an absorbent material. The second fluid collector 1212b includes a single-prong collector. The single prong of the second fluid collector 1212b includes an upper segment 1220b having an upper surface, a closure member 1214b, and sealing members 1280b; a compression member 1290b; and a collector 1216b made from an absorbent material.

A wide variety of absorbent materials capable of acquiring and storing a fluid sample may be used without detracting from the spirit of the invention, including but not limited to a swab, a sponge, and a material that dissolves subsequent to collection of the sample. In one embodiment of the invention, the absorbent material may be saturated with a saliva-producing substance to aid in the collection of the fluid sample. Additionally, the collectors 1216a, 1216b may include a sufficiency or visual indicator to indicate when a sufficient amount of the fluid sample is present in the collectors 1216a, 1216b. The first and second fluid collector 1212a, 1212b, receive a fluid sample from a test subject and temporarily stores the fluid sample until it is transferred to the housing 1201. In one embodiment of the invention, the first fluid collector 1212a receives a fluid sample from a test subject to be used in a split sample fluid testing device.

The housing 1201 includes a first sample receiving member 1218a disposed on a first side of the housing 1201 to receive the first fluid collector 1212a. In one embodiment of the invention, the first sample receiving member 1218a includes two collection chambers 1274 to receive the two-pronged first fluid collector 1212a through two openings 1270, thus forming a split sample. The first sample receiving member 1218a is in fluid communication with a fluid sample retention member, such as a confirmation collection chamber 1210, and a test cartridge member 1204. The test cartridge member 1204 includes a test cartridge chamber 1250; a test cartridge 1252; at least one membrane test strip 1206 located on the test cartridge 1252 to indicate the presence or absence of at least one analyte; and a test cartridge fluid reservoir 1208 in fluid communication with the test cartridge 1252 and the sample receiving member 1218. In one embodiment of the invention, the housing 1201 includes windows on the front, back or both sides of the housing 1201 for viewing of the membrane test strip 1206. A wide variety of housings 1201 may be implemented without detracting from the spirit of the invention, including but not limited to forming the housing 1201 from a clear material allowing the membrane test strips 1206 to be viewed without a window.

The test cartridge fluid reservoir 1208 may be formed in a variety of shapes without detracting from the spirit of the invention, including a v-shaped chamber with a flat bottom 1231. The test cartridge fluid reservoir 1208 with the v-shaped chamber with a flat bottom 1231 allows the test cartridge 1252 and membrane test strips 1206 to fully engage the fluid sample while maintaining a small volume of the fluid sample. In one embodiment of the invention, the v-shaped chamber with a flat bottom 1231 forms a volume of less than seven hundred (700) microliters. An opening 1204 at the bottom of the second collection chamber 1274 is in fluid connection via a channel 1219 with the test cartridge fluid reservoir 1208. A wide variety of connection mechanisms may be implemented to connect the second collection chamber 1274 and the test cartridge fluid reservoir 1208 without detracting from the spirit of the invention, including but not limited to, tubes, piping, channels molded or carved into the housing 1201, or any other suitable structure.

In one embodiment of the invention, the first sample receiving member 1218a includes a first collection chamber 1274 in fluid communication with the confirmation collection chamber 1210 and a second collection chamber 1274 in fluid communication with the test cartridge member 1204. The first collection chamber 1274 and the confirmation collection chamber 1210 are not in fluid communication with any other elements or components of the housing 1201, including the second collection chamber 1274 and the test cartridge member 1204. The second collection chamber 1274 is in fluid communication with the test cartridge fluid reservoir 1208, which is in fluid communication with the test cartridge 1252 and the membrane test strips 1206.

Once the first fluid collector 1212a receives a first fluid sample from a test subject, the first fluid collector 1212a is inserted into the two collection chambers 1274 in the first sample receiving member 1218a, through two openings 1270. The fluid sample is expelled by compressing the first collectors 1216a between the first compression members 1290a of both prongs against the bottom surface of the lower portion of the two collection chambers 1274, thereby releasing the entrapped fluid into the housing 1201. The fluid sample from the test subject is delivered from the first collection chamber 1274 to the confirmation collection chamber 1210 and from the second collection chamber 1274 to the test cartridge fluid reservoir 1208. The fluid sample is only obtained a single time with the two-prong first fluid collector 1212a while maintaining fluid sample integrity through the collection, storage and analysis of the fluid sample with two distinct storage areas: the confirmation collection chamber 1210 and the test cartridge fluid reservoir 1208.

Once the first fluid collector 1212a is secured within the housing 1201, the fluid sample from the confirmation collection chamber 1210 is not in fluid communication with the fluid sample in the test cartridge fluid reservoir 1208. The confirmation collection chamber 1210 fluid sample may be accessed by a third party as previously disclosed, typically subsequent to the testing of the fluid sample in the test cartridge fluid reservoir 1208. In one embodiment of the invention, the confirmation collection chamber 1210 is located below the first collection chamber 1274. In another embodiment of the invention, the confirmation collection chamber 1210 is removable from the housing 1201 after the fluid sample is extracted from the first fluid collector 1212a via a threaded connection 1253.

The first fluid collector 1212a secures the fluid sample within the first sample receiving member 1218a with the sealing members 1280a to form a seal between the first fluid collector 1212*a* and the fluid collection chambers 1274. In one embodiment, each prong of the first fluid collector 1212*a* includes sealing members 1280*a* located near the top and bottom of the first upper segments 1220*a* to seal both of the two collection chambers 1274. The sealing members 1280*a* include sealing rings. The sealing rings may be attached at locations close to the top and bottom of the first upper segments 1220*a*. Generally, the dimensions of sealing members 1280*a*, and the sealing rings, comport with the interior dimension of the two collection chambers 1274 in order to prevent the sample from escaping through the first openings 1270. Once the first fluid collector 1212*a* has been inserted into the first sample receiving member 1218*a*, a first locking mechanism 1281*a*, 1234*a* prevents the removal of the first fluid collector 1212*a* from the first sample receiving member 1218*a*. The first locking mechanism 1281*a*, 1234*a* includes first locking tabs 1281*a* laterally extending from the first closure member 1214*a* and first locking slots 1234*a* located near the top of the first sample receiving members 1218*a*. When the first fluid collector 1212*a* is inserted into the first sample receiving member 1218*a*, the first locking tabs 1281*a* insert into the first locking slots 1234*a*, locking the first fluid collector 1212*a* within the first sample receiving member 1218*a*.

The test cartridge 1252 includes slots for one or more membrane test strips 1206. In one embodiment of the invention, the test cartridge 1252 includes locations or slots for membrane test strips 1206 on both the front and back of the test cartridge 1252 in a back-to-back formation. The test cartridge 1252 may include multiple locations for the membrane test strips 1206 on either the front, back or both sides of the test cartridge 1252. The test cartridge 1252 may allow for a wide number of membrane test strips 1206 to be attached to the test cartridge without detracting from the spirit of the invention, including but not limited to, six (6), twelve (12), or twenty-four (24) membrane test strips 1206. A wide variety of attachment mechanism may be used to attach the membrane test strips 1206 to the test cartridge 1252 without detracting to the spirit of the invention, including but not limited to, slotted membrane test strip holders 1298 on the test cartridge 1252 and a protective sheet attached to the test cartridge 1252 that covers and impedes movement of the test strip 1206 from the test strip holders 1298. After the membrane test strips 1206 are attached to the test cartridge 1252, the test cartridge 1252 is inserted into the test cartridge chamber 1250 through a test cartridge chamber opening 1272 and is placed between test cartridge guides 1237 on both ends of the test cartridge chamber 1250. In one embodiment of the invention, the membrane test strips 1206 extend beyond the test cartridge 1252 into the test cartridge fluid reservoir 1208. A test cartridge cap 1271 and a test cartridge seal 1232 are then inserted into the test cartridge chamber 1250 to secure the test cartridge 1252 within the housing 1201. In one embodiment of the invention, the test cartridge cap 1271 is fixedly attached to the test cartridge 1252 prior to insertion into the test cartridge chamber 1250 or the test cartridge cap 1271 and the test cartridge 1252 are formed from a continuous material. In another embodiment of the invention, the test cartridge cap 1271 attaches to a top edge of the test cartridge chamber opening 1272. Advantageously, different versions of the test cartridge 1252 may be developed to test different combinations of analytes, thereby allowing the test administrator to select the appropriate analyte test suite at the test site. The test cartridge chamber 1250, the test cartridge cap 1271, or a combination of both may include a locking mechanism 1228, 1238 to secure the test cartridge 1252 within the test cartridge chamber 1250, thereby preventing the removal of the test cartridge 1252 from housing 1201. For example, the locking mechanism 1228, 1238 includes locking tabs 1228 extending laterally from the test cartridge cap 1271 that insert into the locking slots 1238 formed on the top edge of the test cartridge chamber opening 1272, thereby locking the test cartridge 1252 within the test cartridge chamber 1250.

The test cartridge 1252 and test cartridge cap 1271 may be made from a variety of materials without detracting from the spirit of the invention, including but not limited to, plastic, ceramic, metal, glass, wood, rubber, polymer, fiber-reinforced polymer, or any combination thereof. In one embodiment, the test cartridge 1252 is formed from plastic and is approximately 70 millimeters in height, 40 millimeters in width, and 5 millimeters in thickness.

After the fluid sample has been expelled from the first fluid collector 1212*a* into the test cartridge fluid reservoir 1217, the fluid sample encounters the proximal end of the membrane test strip 1206 and begins to move upward towards the upper end of the membrane test strip 1206 by capillary action. Each membrane test strip 1206 generally indicates the presence or absence of at least one analyte. A single drug, or class of drugs, is indicated by each membrane test strip 1206, including without limitation, for example, cocaine (COC), amphetamine (AMP), methamphetamine (mAMP), marijuana (THC), methadone (MTD), phencyclidine (PCP), morphine, barbiturates, benzodiazepines, or alcohol. In one embodiment, the test strips 1106 may be lateral flow test strips.

In one embodiment, the test cartridge chamber 1250 and/or the test cartridge fluid reservoir 1208 may be attached to an electrical device that supplies an electric current to the fluid sample. The electrical current may be used to separate elements within the fluid sample prior to testing of the fluid sample.

The housing 1201 includes a second sample receiving member 1218*b* disposed on a second side of the housing 1201, opposite the first side, to receive the second fluid collector 1212*b*. In one embodiment of the invention, the second sample receiving member 1218*b* includes a single collection chamber 1275 to receive the second fluid collector 1212*b* through single opening 1273. The second sample receiving member 1218*b* is in fluid communication with a fluid sample retention member, such as a sample collection chamber 1211. The single collection chamber 1275 is in fluid communication with the sample collection chamber 1211.

Once the second fluid collector 1212*b* receives a second fluid sample from a test subject, the second fluid collector 1212*b* is inserted into the single collection chambers 1275 in the second sample receiving member 1218*b*, through a single opening 1273. The fluid sample is expelled by compressing the second collectors 1216*b* between the second compression members 1290*b* of the prong against the bottom surface of the lower portion of the single collection chamber 1275, thereby releasing the entrapped fluid into the housing 1201. The fluid sample from the test subject is delivered from the single collection chamber 1275 to the sample collection chamber 1211. The sample collection chamber 1211 fluid sample may be accessed by a third party for testing of the second fluid sample. In one embodiment of the invention, the sample collection chamber 1211 is located below the single collection chamber 1275. In another embodiment of the invention, the sample collection chamber 1211 is removable from the housing 1201 after the fluid sample is extracted from the second fluid collector 1212*b* via a threaded connection 1253.

The second fluid collector 1212*b* secures the fluid sample within the second sample receiving member 1218*b* with the sealing members 1280*b* to form a seal between the second fluid collector 1212*b* and the single collection chamber 1275. The prong includes sealing members 1280*b* located near the top and bottom of the second upper segments 1220*b* to seal the prong inside of the single collection chambers 1275. The sealing members 1280*b* include sealing rings. The sealing rings may be attached at locations close to the top and bottom of the second upper segments 1220*b*. Generally, the dimensions of sealing members 1280*b*, and the sealing rings, comport with the interior dimension of the single collection chamber 1275 in order to prevent the sample from escaping through the single opening 1273. Once the second fluid collector 1212*b* has been inserted into the second sample receiving member 1218*b*, a second locking mechanism 1281*b*, 1234*b* prevents the removal of the second fluid collector 1212*b* from the second sample receiving member 1218*b*. The second locking mechanism 1281*b*, 1234*b* includes second locking tabs 1281*b* laterally extending from the second closure member 1214*b* and second locking slots 1234*b* located near the top of the second sample receiving members 1218*b*. When the second fluid collector 1212*b* is inserted into the second sample receiving member 1218*b*, the second locking tabs 1281*b* insert into the second locking slots 1234*b*, locking the second fluid collector 1212*b* within the second sample receiving member 1218*b*.

The fluid samples taken by the first fluid collector 1212*a* may be used to determine toxicology of the patient and the fluid sample taken by the second fluid collection 1212*b* may be used to detect genomic or proteomic information such that certain DNA sequences or proteins may be detected that are genetic predispositions for certain diseases such as various forms of cancer, diabetes, etc.

The housing may include an immunoassay-based fingerprint acquisition pad 1260 to positively identify an individual associated with the fluid collection and analyte test. In one embodiment of the invention, the collection chambers 1274, 1275 and/or the test cartridge fluid reservoir 1208 may be in fluid communication with the immunoassay-based fingerprint acquisition pad 1260. The immunoassay-based fingerprint acquisition pad 1260 may be removably connected to the housing 1201 or fixedly attached to the housing 1201. The immunoassay-based fingerprint acquisition pad 1260 is enclosed by a cover 1266 that is held closed by closure member and pivots into the opened position on the axis defined by the hinges 1262. The cover 1266 may be secured after the fingerprint of the test subject has been acquired, using various locking mechanisms, including without limitation a tab-and-slot arrangement, or security tape.

The immunoassay-based fingerprint acquisition pad 1260 may be a stand-alone apparatus connected to the housing 1201 or the immunoassay-based fingerprint acquisition pad 1260 may be in fluid communication with the test cartridge fluid reservoir 1208. The immunoassay-based fingerprint acquisition pad 1260 in fluid communication with the test cartridge fluid reservoir 1208 functions as previously disclosed.

In an embodiment of the invention, the immunoassay-based fingerprint acquisition pad 1260 includes a compressible, porous reaction medium, having a control zone and a plurality of reaction zones, arranged on a porous support. The control zone includes a control reagent to identify the fluid sample donor, and each reaction zone includes a reaction reagent to determine the presence of a specific analyte in the fluid sample. The control reagent includes a member of a predetermined ligand/receptor binding pair. Similarly, each reaction reagent includes a member of a predetermined ligand/receptor binding pair. Various ligand/receptor binding pairs for use within the control and reaction zones are discussed within the '863 and '815 patents.

In an embodiment of the invention, the immunoassay-based fingerprint acquisition pad 1260 is fluidly coupled to the collection chambers 1274, 1275. A signal-producing agent, located on upper surface of the porous support or the lower surface of the reaction medium, mixes with the fluid sample provided to the immunoassay-based fingerprint acquisition pad 1260. The production of an image or pattern which identifies the person providing the sample is accomplished by applying a fingertip to the upper surface of the reaction medium and compressing the reaction medium so that the fluid sample/signal-producing agent mixture permeates the reaction medium and allowing the control zone ligand/receptor reaction to take place so that the members of this immunological pair bond with the signal-producing agent and produce the fingerprint image. Similarly, the presence or absence of a specific analyte in the fluid sample is indicated within each reaction zone by the reaction of each specific reaction reagent with the fluid sample/signal-producing agent mixture.

Although the invention is described herein with reference to specific embodiments, various modifications and changes can be made without departing from the scope of the invention as set forth in the claims below. The combination of embodiments is expressly anticipated, unless the embodiments and specifically mutually exclusive. A claimed invention may include multiple embodiments as disclosed herein. Accordingly, the specification and figures are to be regarded in an illustrative rather than a restrictive sense, and all such modifications are intended to be included within the scope of the invention. Any benefits, advantages, or solutions to problems that are described herein with regard to specific embodiments are not intended to be construed as a critical, required, or essential feature or element of any or all the claims.

From time-to-time, the invention is described herein in terms of these example embodiments. Description in terms of these embodiments is provided to allow the various features and embodiments of the invention to be portrayed in the context of an exemplary application. After reading this description, it will become apparent to one of ordinary skill in the art how the invention can be implemented in different and alternative environments. Unless defined otherwise, all technical and scientific terms used herein have the same meaning as is commonly understood by one of ordinary skill in the art to which this invention belongs.

The preceding discussion is presented to enable a person skilled in the art to make and use the invention. The general principles described herein may be applied to embodiments and applications other than those detailed below without departing from the spirit and scope of the invention as defined by the appended claims. The invention is not intended to be limited to the embodiments shown, but is to be accorded the widest scope consistent with the principles and features disclosed herein.

In addition, while a particular feature of the invention may have been disclosed with respect to only one of several embodiments, such feature may be combined with one or more other features of the other embodiments as may be desired. It is therefore, contemplated that the claims will cover any such modifications or embodiments that fall within the true scope of the invention.

The various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the invention. In addition, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one", "one or more" or the like; and adjectives such as "conventional", "traditional", "normal", "standard", "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more", "at least", "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed across multiple locations.

Unless stated otherwise, terms such as "first" and "second" are used to arbitrarily distinguish between the elements such terms describe. Thus, these terms are not necessarily intended to indicate temporal or other prioritization of such elements.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the field or any related fields are intended to be within the scope of the following claims.

One skilled in the art will recognize that different embodiments may be formed in a similar manner having different characteristics depending upon need, performance, or some other criteria. It will thus be appreciated by those skilled in the art that changes could be made to the embodiments described above without departing from the broad inventive concept thereof. It is understood, therefore, that the invention disclosed herein is not limited to the particular embodiments disclosed, but it is intended to cover modifications within the spirit and scope of the present invention as defined by the appended claims.

Although this invention has been described in conjunction with specific embodiments thereof, many alternatives, modifications and variations will be apparent to those skilled in the art. Accordingly, the preferred embodiments of the invention as set forth herein are intended to be illustrative, not limiting. Various changes may be made without departing from the true spirit and full scope of the invention as set forth herein.

What is claimed is:

1. An apparatus for testing a fluid sample comprising:
   a sample receiving member having an opening for receiving a fluid sample, wherein the sample receiving member comprises a sample collection chamber;
   a fluid collector to collect the fluid sample and transfer the fluid sample into the sample receiving member, the fluid collector comprising a lancet and an absorbent material to absorb the fluid sample;
   a test cartridge member in fluid communication with the sample collection chamber; and
   a sample retention member, in fluid communication with the sample collection chamber, to retain a portion of the fluid sample.

2. The apparatus of claim 1, wherein the lancet comprises:
   a housing; and
   a sharp tip portion disposed within the housing, wherein the sharp tip portion is configured to be driven out of the housing by a drive spring and retract within the housing by a return spring.

3. The apparatus of claim 2, wherein the drive spring drives the sharp tip portion and the return spring retracts the sharp tip portion in a single stroke.

4. The apparatus of claim 1, wherein the fluid collector further comprises:

a closure member capable of sealing the opening of the sample receiving member when the fluid collector is inserted into the sample receiving member.

5. The apparatus of claim 4, wherein the closure member is capable of sealing an open end of the sample collection chamber.

6. The apparatus of claim 1, wherein the absorbent material comprises a visual indicator to indicate the presence of a predetermined amount of the fluid sample.

7. The apparatus of claim 1, wherein the fluid collector further comprises a compression member operatively associated with the absorbent material, wherein the compression member comprises a compression segment to compress the absorbent material of the fluid collector.

8. The apparatus of claim 1, further comprising a device for biometric identification.

9. The apparatus of claim 8, wherein the device for biometric identification is a fingerprint acquisition pad.

10. The apparatus of claim 1, further comprising at least one test strip disposed within the test cartridge member, wherein the at least one test strip indicates the presence or absence of at least one analyte in the fluid sample.

11. The apparatus of claim 10, wherein the test cartridge member comprises a test cartridge.

12. The apparatus of claim 11, wherein the test cartridge comprises the at least one test strip.

13. The apparatus of claim 12, wherein the test cartridge member comprises a test cartridge chamber and a test cartridge fluid reservoir in fluid communication with the sample receiving member, wherein the test cartridge is inserted into the test cartridge chamber and wherein the at least one test strip is in fluid communication with the test cartridge fluid reservoir.

14. The apparatus of claim 13, wherein the test cartridge fluid reservoir is a v-shaped chamber with a flat bottom.

15. The apparatus of claim 14, wherein the test cartridge comprises a front set of test strip slots and a back set of test strip slots.

16. The apparatus of claim 15, wherein the at least one test strip is a plurality of test strips inserted into the front and back sets of test strip slots and wherein the plurality of test strips are in fluid communication with the test cartridge fluid reservoir.

17. The apparatus of claim 11, wherein the test cartridge member comprises a cap to secure the test cartridge.

* * * * *